United States Patent
Rothkopf et al.

(10) Patent No.: US 10,942,491 B2
(45) Date of Patent: Mar. 9, 2021

(54) WEARABLE ELECTRONIC DEVICE

(71) Applicant: Apple Inc., Cupertino, CA (US)

(72) Inventors: Fletcher R. Rothkopf, Los Altos, CA (US); Jonathan Ive, San Francisco, CA (US); Julian Hoenig, San Francisco, CA (US); Rico Zorkendorfer, San Francisco, CA (US)

(73) Assignee: APPLE INC., Cupertino, CA (US)

(*) Notice: Subject to any disclaimer, the term of this patent is extended or adjusted under 35 U.S.C. 154(b) by 0 days.

(21) Appl. No.: 16/826,130

(22) Filed: Mar. 20, 2020

(65) Prior Publication Data

US 2020/0233380 A1 Jul. 23, 2020

Related U.S. Application Data

(63) Continuation of application No. 15/261,917, filed on Sep. 10, 2016, now Pat. No. 10,627,783, and a
(Continued)

(51) Int. Cl.
*G04G 17/02* (2006.01)
*A61B 5/0295* (2006.01)
(Continued)

(52) U.S. Cl.
CPC .......... *G04G 17/02* (2013.01); *A61B 5/0205* (2013.01); *A61B 5/0261* (2013.01);
(Continued)

(58) Field of Classification Search
None
See application file for complete search history.

(56) References Cited

U.S. PATENT DOCUMENTS 2,237,860 A 4/1941 Bolle
2,288,215 A 6/1942 Taubert et al.
(Continued)

FOREIGN PATENT DOCUMENTS

CH 1888928 1/1937
CN 1302740 9/2001
(Continued)

OTHER PUBLICATIONS

Author Unknown, "Desirable Android Wear smartwatch from LG," Gulf News, Dubai, 3 pages, Jan. 30, 2015.
(Continued)

*Primary Examiner* — Brian T Gedeon
(74) *Attorney, Agent, or Firm* — Brownstein Hyatt Farber Schreck, LLP

(57) ABSTRACT

A consumer product that is a portable and, in some cases, a wearable electronic device. The wearable electronic device may have functionalities including: keeping time; monitoring a user's physiological signals and providing health-related information based on those signals; communicating with other electronic devices or services; visually depicting data on a display; gather data form one or more sensors that may be used to initiate, control, or modify operations of the device; determine a location of a touch on a surface of the device and/or an amount of force exerted on the device, and use either or both as input.

19 Claims, 26 Drawing Sheets

Related U.S. Application Data continuation of application No. 15/261,912, filed on Sep. 10, 2016, now Pat. No. 10,620,591, and a continuation of application No. 15/261,914, filed on Sep. 10, 2016, now Pat. No. 10,613,485, and a continuation of application No. 14/842,617, filed on Sep. 1, 2015, now Pat. No. 10,599,101.

(60) Provisional application No. 62/044,974, filed on Sep. 2, 2014.

(51) Int. Cl.

| | |
|---|---|
| *G06F 1/16* | (2006.01) |
| *G06F 3/01* | (2006.01) |
| *G04G 21/02* | (2010.01) |
| *G04B 39/02* | (2006.01) |
| *A61B 5/00* | (2006.01) |
| *A61B 5/1455* | (2006.01) |
| *A61B 5/0205* | (2006.01) |
| *A61B 5/026* | (2006.01) |
| *G04B 3/04* | (2006.01) |
| *G04G 13/00* | (2006.01) |
| *A61B 5/024* | (2006.01) |
| *A61B 5/08* | (2006.01) |

(52) U.S. Cl.
CPC ........ *A61B 5/0295* (2013.01); *A61B 5/14551* (2013.01); *A61B 5/681* (2013.01); *G04B 39/02* (2013.01); *G04G 21/025* (2013.01); *G06F 1/163* (2013.01); *G06F 1/169* (2013.01); *G06F 1/1643* (2013.01); *G06F 3/015* (2013.01); *G06F 3/016* (2013.01); *A61B 5/02427* (2013.01); *A61B 5/02438* (2013.01); *A61B 5/0816* (2013.01); *A61B 5/14552* (2013.01); *G04B 3/04* (2013.01); *G04G 13/00* (2013.01)

(56) References Cited

U.S. PATENT DOCUMENTS

| | | | |
|---|---|---|---|
| 2,497,935 A | 2/1950 | Feurer | |
| 2,771,734 A | 11/1956 | Morf | |
| 2,788,236 A | 4/1957 | Kafowi | |
| 2,797,592 A | 7/1957 | Marrapese | |
| 3,040,514 A | 6/1962 | Dinstman | |
| 3,056,030 A | 9/1962 | Kelchner | |
| 3,130,539 A | 4/1964 | Davis | |
| 3,355,873 A | 12/1967 | Morf | |
| 3,362,154 A | 1/1968 | Perret | |
| 3,410,247 A | 11/1968 | Dronberger | |
| 3,495,398 A | 2/1970 | Widmer et al. | |
| 3,577,876 A | 5/1971 | Spadini | |
| 3,621,649 A | 11/1971 | Vulcan et al. | |
| 3,662,618 A | 5/1972 | Kroll et al. | |
| 3,733,803 A | 5/1973 | Hiraga | |
| 4,007,347 A | 2/1977 | Haber | |
| 4,031,341 A | 6/1977 | Wuthrich et al. | |
| 4,037,068 A | 7/1977 | Gaynor | |
| 4,077,200 A | 3/1978 | Schneider | |
| 4,133,404 A | 1/1979 | Griffin | |
| 4,170,104 A | 10/1979 | Yamagata | |
| 4,258,096 A | 3/1981 | Lamarche | |
| 4,287,400 A | 9/1981 | Kitik | |
| 4,289,400 A | 9/1981 | Kubola et al. | |
| 4,311,026 A | 1/1982 | Ochoa | |
| 4,311,990 A | 1/1982 | Burke | |
| 4,324,956 A | 4/1982 | Sakakino et al. | |
| 4,345,119 A | 8/1982 | Latasiewicz | |
| 4,364,674 A | 12/1982 | Tesch | |
| 4,379,642 A | 4/1983 | Meyrat | |
| 4,395,134 A | 7/1983 | Luce | |
| 4,396,298 A | 8/1983 | Ripley | |
| 4,417,824 A | 11/1983 | Paterson et al. | |
| 4,448,199 A * | 5/1984 | Schmid | A61B 5/02438 600/393 |
| 4,520,306 A | 5/1985 | Kirby | |
| 4,581,509 A | 4/1986 | Sanford et al. | |
| 4,600,316 A | 7/1986 | Besson | |
| 4,617,461 A | 10/1986 | Subbarao et al. | |
| 4,634,861 A | 1/1987 | Ching et al. | |
| 4,641,026 A | 2/1987 | Garcia, Jr. | |
| 4,670,737 A | 6/1987 | Rifling | |
| 4,766,642 A | 8/1988 | Gaffney et al. | |
| 4,783,772 A | 11/1988 | Umemoto et al. | |
| 4,884,073 A | 11/1989 | Souloumiac | |
| 4,914,831 A | 4/1990 | Kanezashi et al. | |
| 4,922,070 A | 5/1990 | Dorkinski | |
| 4,931,794 A | 6/1990 | Haag | |
| 4,952,799 A | 8/1990 | Loewen | |
| 4,980,685 A | 12/1990 | Souloumiac et al. | |
| 4,987,299 A | 1/1991 | Kobayashi et al. | |
| 5,034,602 A | 7/1991 | Garcia et al. | |
| 5,177,355 A | 1/1993 | Branan | |
| 5,214,278 A | 5/1993 | Banda | |
| 5,258,592 A | 11/1993 | Nishikawa et al. | |
| 5,288,993 A | 2/1994 | Bidiville et al. | |
| 5,347,123 A | 9/1994 | Jackson et al. | |
| 5,383,166 A | 1/1995 | Gallay | |
| 5,471,054 A | 11/1995 | Watanabe | |
| 5,477,508 A | 12/1995 | Will | |
| 5,509,174 A | 4/1996 | Worrell | |
| 5,559,761 A | 9/1996 | Frenkel et al. | |
| 5,572,314 A | 11/1996 | Hyman et al. | |
| 5,583,560 A | 12/1996 | Florin et al. | |
| 5,631,881 A | 5/1997 | Pessey et al. | |
| 5,726,645 A | 3/1998 | Kamon et al. | |
| 5,748,111 A | 5/1998 | Bates | |
| 5,825,353 A | 10/1998 | Will | |
| 5,841,050 A | 11/1998 | Clift et al. | |
| 5,847,335 A | 12/1998 | Sugahara et al. | |
| 5,867,082 A | 2/1999 | Van Zeeland | |
| 5,943,233 A | 8/1999 | Ebina | |
| 5,953,001 A | 9/1999 | Challener et al. | |
| 5,960,366 A | 9/1999 | Duwaer et al. | |
| 5,963,332 A | 10/1999 | Feldman et al. | |
| 5,999,168 A | 12/1999 | Rosenberg et al. | |
| 6,069,567 A | 5/2000 | Zawilski | |
| 6,128,006 A | 10/2000 | Rosenberg et al. | |
| 6,134,189 A | 10/2000 | Carrard | |
| 6,154,201 A | 11/2000 | Levin et al. | |
| 6,175,679 B1 | 1/2001 | Veligdan et al. | |
| 6,203,190 B1 | 3/2001 | Stotz | |
| 6,241,684 B1 | 6/2001 | Amano | |
| 6,246,050 B1 | 6/2001 | Tullis et al. | |
| 6,252,825 B1 | 6/2001 | Perotto | |
| 6,304,247 B1 | 10/2001 | Black | |
| 6,355,891 B1 | 3/2002 | Ikunami | |
| 6,361,502 B1 | 3/2002 | Puolakanaho et al. | |
| 6,377,239 B1 | 4/2002 | Isikawa | |
| 6,392,640 B1 | 5/2002 | Will | |
| 6,396,006 B1 | 5/2002 | Yokoji et al. | |
| 6,422,740 B1 | 7/2002 | Leuenberger | |
| 6,477,117 B1 | 11/2002 | Narayanaswami et al. | |
| 6,502,982 B1 | 1/2003 | Bach et al. | |
| 6,525,278 B2 | 2/2003 | Villain et al. | |
| 6,556,222 B1 | 4/2003 | Narayanaswami | |
| 6,575,618 B1 | 6/2003 | Inoue et al. | |
| 6,587,400 B1 | 7/2003 | Line | |
| 6,636,197 B1 | 10/2003 | Goldenberg et al. | |
| 6,646,635 B2 | 11/2003 | Pogatetz et al. | |
| 6,661,438 B1 | 11/2003 | Shiraishi et al. | |
| 6,672,758 B2 | 1/2004 | Ehrsam et al. | |
| 6,794,992 B1 | 9/2004 | Rogers | |
| 6,809,275 B1 | 10/2004 | Cheng et al. | |
| 6,834,430 B2 | 12/2004 | Worrell | |
| 6,846,998 B2 | 1/2005 | Hasumi et al. | |
| 6,882,596 B2 | 4/2005 | Guanter | |
| 6,888,076 B2 | 5/2005 | Hetherington | |
| 6,896,403 B1 | 5/2005 | Gau | |
| 6,909,378 B1 | 6/2005 | Lambrechts et al. | |

(56) References Cited

U.S. PATENT DOCUMENTS

| | | |
|---|---|---|
| 6,914,551 B2 | 7/2005 | Vidal |
| 6,961,099 B2 | 11/2005 | Takano et al. |
| 6,963,039 B1 | 11/2005 | Weng et al. |
| 6,967,903 B2 | 11/2005 | Guanter |
| 6,977,868 B2 | 12/2005 | Brewer et al. |
| 6,982,930 B1 | 1/2006 | Hung |
| 6,985,107 B2 | 1/2006 | Anson |
| 6,987,568 B2 | 1/2006 | Dana |
| 6,998,553 B2 | 2/2006 | Hisamune et al. |
| 7,016,263 B2 | 3/2006 | Gueissaz et al. |
| 7,021,442 B2 | 4/2006 | Borgerson |
| 7,031,228 B2 | 4/2006 | Born et al. |
| 7,034,237 B2 | 4/2006 | Ferri et al. |
| 7,081,905 B1 | 7/2006 | Raghunath et al. |
| 7,102,626 B2 | 9/2006 | Denny, III |
| 7,111,365 B1 | 9/2006 | Howie, Jr. |
| 7,113,450 B2 | 9/2006 | Plancon et al. |
| 7,119,289 B2 | 10/2006 | Lacroix |
| 7,135,673 B2 | 11/2006 | Saint Clair |
| 7,167,083 B2 | 1/2007 | Giles |
| 7,244,927 B2 | 7/2007 | Huynh |
| 7,255,473 B2 | 8/2007 | Hiranuma et al. |
| 7,265,336 B2 | 9/2007 | Hataguchi et al. |
| 7,274,303 B2 | 9/2007 | Dresti et al. |
| 7,285,738 B2 | 10/2007 | Lavigne et al. |
| 7,286,063 B2 | 10/2007 | Gauthey |
| 7,292,741 B2 | 11/2007 | Ishiyama et al. |
| 7,358,481 B2 | 4/2008 | Yeoh et al. |
| 7,369,308 B2 | 5/2008 | Tsuruta et al. |
| 7,371,745 B2 | 5/2008 | Ebright et al. |
| 7,385,874 B2 | 6/2008 | Vuilleumier |
| 7,404,667 B2 | 7/2008 | Born et al. |
| 7,465,917 B2 | 12/2008 | Chin et al. |
| 7,468,036 B1 | 12/2008 | Rulkov et al. |
| 7,506,269 B2 | 3/2009 | Lang et al. |
| 7,520,664 B2 | 4/2009 | Wai |
| 7,528,824 B2 | 5/2009 | Kong |
| 7,545,367 B2 | 6/2009 | Sunda et al. |
| 7,591,582 B2 | 9/2009 | Hiranuma et al. |
| 7,593,755 B2 | 9/2009 | Colando et al. |
| 7,605,846 B2 | 10/2009 | Watanabe |
| 7,634,263 B2 | 12/2009 | Louch et al. |
| 7,646,677 B2 | 1/2010 | Nakamura |
| 7,655,874 B2 | 2/2010 | Akieda |
| 7,682,070 B2 | 3/2010 | Burton |
| 7,708,457 B2 | 5/2010 | Girardin |
| 7,710,456 B2 | 5/2010 | Koshiba et al. |
| 7,732,724 B2 | 6/2010 | Otani et al. |
| 7,761,246 B2 | 7/2010 | Matsui |
| 7,763,819 B2 | 7/2010 | Leda et al. |
| 7,772,507 B2 | 8/2010 | Orr |
| 7,778,115 B2 | 8/2010 | Ruchonnet |
| 7,781,726 B2 | 8/2010 | Matsui et al. |
| RE41,637 E | 9/2010 | O'Hara et al. |
| 7,791,588 B2 | 9/2010 | Tierling et al. |
| 7,791,597 B2 | 9/2010 | Silverstein et al. |
| 7,822,469 B2 | 10/2010 | Lo |
| 7,856,255 B2 | 12/2010 | Tsuchiya et al. |
| 7,858,583 B2 | 12/2010 | Schmidt et al. |
| 7,865,324 B2 | 1/2011 | Lindberg |
| 7,894,957 B2 | 2/2011 | Carlson |
| 7,946,758 B2 | 5/2011 | Mooring |
| 8,063,892 B2 | 11/2011 | Shahoian et al. |
| 8,138,488 B2 | 3/2012 | Grot |
| 8,143,981 B2 | 3/2012 | Washizu et al. |
| 8,167,126 B2 | 5/2012 | Stiehl |
| 8,169,402 B2 | 5/2012 | Shahoian et al. |
| 8,188,989 B2 | 5/2012 | Levin et al. |
| 8,195,313 B1 | 6/2012 | Fadell et al. |
| 8,229,535 B2 | 7/2012 | Mensinger et al. |
| 8,248,815 B2 | 8/2012 | Yang et al. |
| 8,263,886 B2 | 9/2012 | Lin et al. |
| 8,263,889 B2 | 9/2012 | Takahashi et al. |
| 8,275,327 B2 | 9/2012 | Yi et al. |
| 8,294,670 B2 | 10/2012 | Griffin et al. |
| 8,312,495 B2 | 11/2012 | Vanderhoff |
| 8,318,340 B2 | 11/2012 | Stimits |
| 8,368,677 B2 | 2/2013 | Yamamoto |
| 8,371,745 B2 | 2/2013 | Manni |
| 8,373,661 B2 | 2/2013 | Lan et al. |
| 8,410,971 B2 | 4/2013 | Friedlander |
| 8,432,368 B2 | 4/2013 | Momeyer et al. |
| 8,439,559 B2 | 5/2013 | Luk et al. |
| 8,441,450 B2 | 5/2013 | Degner et al. |
| 8,446,713 B2 | 5/2013 | Lai |
| 8,456,430 B2 | 6/2013 | Oliver et al. |
| 8,477,118 B2 | 7/2013 | Lan et al. |
| 8,493,190 B2 | 7/2013 | Periquet et al. |
| 8,508,511 B2 | 8/2013 | Tanaka et al. |
| 8,525,777 B2 | 9/2013 | Stavely et al. |
| 8,562,489 B2 | 10/2013 | Burton et al. |
| 8,568,313 B2 | 10/2013 | Sadhu |
| 8,576,044 B2 | 11/2013 | Chapman |
| 8,593,598 B2 | 11/2013 | Chen et al. |
| 8,607,662 B2 | 12/2013 | Huang |
| 8,614,881 B2 | 12/2013 | Yoo |
| 8,666,682 B2 | 3/2014 | Lavigne et al. |
| 8,677,285 B2 | 3/2014 | Tsern et al. |
| 8,704,787 B2 | 4/2014 | Yamamoto |
| 8,711,093 B2 | 4/2014 | Ong et al. |
| 8,724,087 B2 | 5/2014 | Van De Kerkhof et al. |
| 8,730,167 B2 | 5/2014 | Ming et al. |
| 8,743,088 B2 | 6/2014 | Watanabe |
| 8,783,944 B2 | 7/2014 | Doi |
| 8,797,153 B2 | 8/2014 | Vanhelle et al. |
| 8,804,993 B2 | 8/2014 | Shukla et al. |
| 8,816,962 B2 | 8/2014 | Obermeyer et al. |
| 8,824,245 B2 | 9/2014 | Lau et al. |
| 8,847,741 B2 | 9/2014 | Birnbaum et al. |
| 8,859,971 B2 | 10/2014 | Weber |
| 8,860,674 B2 | 10/2014 | Lee et al. |
| 8,863,219 B2 | 10/2014 | Brown et al. |
| D717,679 S | 11/2014 | Anderssen |
| 8,878,657 B2 | 11/2014 | Periquet et al. |
| 8,885,856 B2 | 11/2014 | Sacha |
| 8,895,911 B2 | 11/2014 | Takahashi |
| 8,905,631 B2 | 12/2014 | Sakurazawa et al. |
| 8,908,477 B2 | 12/2014 | Peters |
| 8,920,022 B2 | 12/2014 | Ishida et al. |
| 8,922,399 B2 | 12/2014 | Bajaj et al. |
| 8,928,452 B2 | 1/2015 | Kim et al. |
| 8,954,135 B2 | 2/2015 | Yuen et al. |
| 8,975,543 B2 | 3/2015 | Hakemeyer |
| 8,994,827 B2 | 3/2015 | Mistry et al. |
| 9,001,625 B2 | 4/2015 | Essery et al. |
| 9,024,733 B2 | 5/2015 | Wouters |
| 9,028,134 B2 | 5/2015 | Koshoji et al. |
| 9,030,446 B2 | 5/2015 | Mistry et al. |
| 9,034,666 B2 | 5/2015 | Vaganov et al. |
| 9,039,614 B2 | 5/2015 | Yuen et al. |
| 9,041,663 B2 | 5/2015 | Westerman |
| 9,042,971 B2 | 5/2015 | Brumback et al. |
| 9,049,998 B2 | 6/2015 | Brumback et al. |
| 9,052,696 B2 | 6/2015 | Breuillot et al. |
| 9,086,717 B2 | 7/2015 | Meerovitsch |
| 9,086,738 B2 | 7/2015 | Leung et al. |
| 9,100,493 B1 | 8/2015 | Zhou |
| 9,101,184 B2 | 8/2015 | Wilson |
| 9,105,413 B2 | 8/2015 | Hiranuma et al. |
| 9,123,483 B2 | 9/2015 | Ferri et al. |
| 9,134,807 B2 | 9/2015 | Shaw et al. |
| 9,141,087 B2 | 9/2015 | Brown et al. |
| 9,176,577 B2 | 11/2015 | Jangaard et al. |
| 9,176,598 B2 | 11/2015 | Sweetser et al. |
| 9,202,372 B2 | 12/2015 | Reams et al. |
| 9,213,409 B2 | 12/2015 | Redelsheimer et al. |
| 9,223,296 B2 | 12/2015 | Yang et al. |
| 9,241,635 B2 | 1/2016 | Yuen et al. |
| 9,244,438 B2 | 1/2016 | Hoover et al. |
| 9,256,209 B2 | 2/2016 | Yang et al. |
| 9,277,156 B2 | 3/2016 | Bennett et al. |
| 9,350,850 B2 | 5/2016 | Pope et al. |
| 9,386,932 B2 | 7/2016 | Chatterjee et al. |
| 9,426,275 B2 | 8/2016 | Eim et al. |

(56) References Cited

U.S. PATENT DOCUMENTS

| | | |
|---|---|---|
| 9,430,042 B2 | 8/2016 | Levin |
| 9,437,357 B2 | 9/2016 | Furuki et al. |
| 9,449,770 B2 | 9/2016 | Sanford et al. |
| 9,501,044 B2 | 11/2016 | Jackson et al. |
| 9,520,100 B2 | 12/2016 | Houjou et al. |
| 9,532,723 B2 | 1/2017 | Kim |
| 9,542,016 B2 | 1/2017 | Armstrong-Muntner |
| 9,545,541 B2 | 1/2017 | Aragones et al. |
| 9,552,023 B2 | 1/2017 | Joo et al. |
| 9,599,964 B2 | 3/2017 | Gracia |
| 9,607,505 B2 | 3/2017 | Rothkopf et al. |
| 9,620,312 B2 | 4/2017 | Ely et al. |
| 9,627,163 B2 | 4/2017 | Ely |
| 9,632,318 B2 | 4/2017 | Goto et al. |
| 9,638,587 B2 | 5/2017 | Marquas et al. |
| 9,651,922 B2 | 5/2017 | Hysek et al. |
| 9,659,482 B2 | 5/2017 | Yang et al. |
| 9,680,831 B2 | 6/2017 | Jooste et al. |
| 9,709,956 B1 | 7/2017 | Ely et al. |
| 9,753,436 B2 | 9/2017 | Ely et al. |
| D800,172 S | 10/2017 | Akana |
| 9,800,717 B2 | 10/2017 | Ma et al. |
| 9,836,025 B2 | 12/2017 | Ely et al. |
| 9,873,711 B2 | 1/2018 | Hoover et al. |
| 9,874,945 B2 | 1/2018 | Fukumoto |
| 9,886,006 B2 | 2/2018 | Ely et al. |
| 9,891,590 B2 | 2/2018 | Shim et al. |
| 9,891,651 B2 | 2/2018 | Jackson et al. |
| 9,898,032 B2 | 2/2018 | Hafez et al. |
| 9,927,902 B2 | 3/2018 | Burr et al. |
| 9,939,923 B2 | 4/2018 | Sharma |
| 9,946,297 B2 | 4/2018 | Nazzaro et al. |
| 9,952,558 B2 | 4/2018 | Ely |
| 9,952,682 B2 | 4/2018 | Zhang et al. |
| 9,971,305 B2 | 5/2018 | Ely et al. |
| 9,971,405 B2 | 5/2018 | Holenarsipur et al. |
| 9,979,426 B2 | 5/2018 | Na et al. |
| 10,001,817 B2 | 6/2018 | Zambetti et al. |
| 10,012,550 B2 | 7/2018 | Yang |
| 10,018,966 B2 | 7/2018 | Ely et al. |
| 10,019,097 B2 | 7/2018 | Ely et al. |
| 10,037,006 B2 | 7/2018 | Ely |
| 10,048,802 B2 | 8/2018 | Shedletsky |
| 10,061,399 B2 | 8/2018 | Bushnell et al. |
| 10,092,203 B2 | 10/2018 | Mirov |
| 10,114,342 B2 | 10/2018 | Kim et al. |
| 10,145,711 B2 | 12/2018 | Boonsom et al. |
| 10,175,652 B2 | 1/2019 | Ely et al. |
| 10,209,148 B2 | 2/2019 | Lyon et al. |
| 10,216,147 B2 | 2/2019 | Ely et al. |
| 10,222,756 B2 | 3/2019 | Ely et al. |
| 10,222,909 B2 | 3/2019 | Shedletsky et al. |
| 10,234,828 B2 | 3/2019 | Ely et al. |
| 10,241,593 B2 | 3/2019 | Chen |
| 10,296,125 B2 | 5/2019 | Ely et al. |
| 10,331,081 B2 | 6/2019 | Ely et al. |
| 10,331,082 B2 | 6/2019 | Ely et al. |
| 10,353,487 B2 | 7/2019 | Chung et al. |
| 10,379,629 B2 | 8/2019 | Bushnell et al. |
| 10,474,194 B1 | 11/2019 | Eli et al. |
| 10,509,486 B2 | 12/2019 | Bushnell et al. |
| 10,551,798 B1 | 2/2020 | Bushnell et al. |
| 10,599,101 B2 | 3/2020 | Rothkopf et al. |
| 2003/0174590 A1 | 9/2003 | Arikawa et al. |
| 2004/0047244 A1 | 3/2004 | Iino et al. |
| 2004/0082414 A1 | 4/2004 | Knox |
| 2004/0130971 A1 | 7/2004 | Ecoffet et al. |
| 2004/0264301 A1 | 12/2004 | Howard et al. |
| 2005/0075558 A1 | 4/2005 | Vecerina et al. |
| 2005/0088417 A1 | 4/2005 | Mulligan |
| 2006/0250377 A1 | 11/2006 | Zadesky et al. |
| 2007/0013775 A1 | 1/2007 | Shin |
| 2007/0050054 A1 | 3/2007 | Sambandam Guruparan et al. |
| 2007/0182708 A1 | 8/2007 | Poupyrev et al. |
| 2007/0211042 A1 | 9/2007 | Kim et al. |
| 2007/0222756 A1 | 9/2007 | Wu et al. |
| 2007/0229671 A1 | 10/2007 | Takeshita et al. |
| 2007/0247421 A1 | 10/2007 | Orsley et al. |
| 2008/0130914 A1 | 6/2008 | Cho |
| 2009/0051649 A1 | 2/2009 | Rondel |
| 2009/0073119 A1 | 3/2009 | Le et al. |
| 2009/0122656 A1 | 5/2009 | Bonnet et al. |
| 2009/0146975 A1 | 6/2009 | Chang |
| 2009/0152452 A1 | 6/2009 | Lee et al. |
| 2009/0217207 A1 | 8/2009 | Kagermeier et al. |
| 2009/0285443 A1 | 11/2009 | Camp et al. |
| 2009/0312051 A1 | 12/2009 | Hansson et al. |
| 2010/0033430 A1 | 2/2010 | Kakutani et al. |
| 2010/0053468 A1 | 3/2010 | Havrill |
| 2010/0081375 A1 | 4/2010 | Rosenblatt et al. |
| 2010/0149099 A1 | 6/2010 | Elias |
| 2011/0007468 A1 | 1/2011 | Burton et al. |
| 2011/0090148 A1 | 4/2011 | Li et al. |
| 2011/0158057 A1 | 6/2011 | Brewer et al. |
| 2011/0242064 A1 | 10/2011 | Ono et al. |
| 2011/0270358 A1 | 11/2011 | Davis et al. |
| 2012/0067711 A1 | 3/2012 | Yang |
| 2012/0068857 A1 | 3/2012 | Rothkopf et al. |
| 2012/0075082 A1 | 3/2012 | Rothkopf et al. |
| 2012/0112859 A1 | 5/2012 | Park et al. |
| 2012/0113044 A1 | 5/2012 | Strazisar et al. |
| 2012/0206248 A1 | 8/2012 | Biggs |
| 2012/0272784 A1 | 11/2012 | Bailey et al. |
| 2013/0037396 A1 | 2/2013 | Yu |
| 2013/0087443 A1 | 4/2013 | Kikuchi |
| 2013/0191220 A1 | 7/2013 | Dent et al. |
| 2013/0235704 A1 | 9/2013 | Grinberg |
| 2013/0261405 A1 | 10/2013 | Lee et al. |
| 2013/0335196 A1 | 12/2013 | Zhang et al. |
| 2014/0009397 A1 | 1/2014 | Gillespie |
| 2014/0045547 A1 | 2/2014 | Singamsetty et al. |
| 2014/0071098 A1 | 3/2014 | You |
| 2014/0073486 A1 | 3/2014 | Ahmed et al. |
| 2014/0132516 A1 | 5/2014 | Tsai et al. |
| 2014/0139486 A1* | 5/2014 | Mistry .................... G06F 3/011 345/175 |
| 2014/0197936 A1 | 7/2014 | Biggs et al. |
| 2014/0275852 A1* | 9/2014 | Hong .................... A61B 5/0002 600/301 |
| 2014/0340318 A1 | 11/2014 | Stringer et al. |
| 2014/0347289 A1 | 11/2014 | Suh et al. |
| 2014/0368442 A1 | 12/2014 | Vahtola |
| 2014/0375579 A1 | 12/2014 | Fujiwara |
| 2015/0049059 A1 | 2/2015 | Zadesky et al. |
| 2015/0098309 A1 | 4/2015 | Adams et al. |
| 2015/0124415 A1 | 5/2015 | Goyal et al. |
| 2015/0186609 A1 | 7/2015 | Utter, II |
| 2015/0221460 A1 | 8/2015 | Teplitxky et al. |
| 2015/0320346 A1 | 11/2015 | Chen |
| 2015/0338642 A1 | 11/2015 | Sanford |
| 2015/0366098 A1 | 12/2015 | Lapetina et al. |
| 2016/0018846 A1 | 1/2016 | Zenoff |
| 2016/0054813 A1 | 2/2016 | Shediwy et al. |
| 2016/0058375 A1 | 3/2016 | Rothkopf et al. |
| 2016/0061636 A1 | 3/2016 | Gowreesunker et al. |
| 2016/0062623 A1 | 3/2016 | Howard et al. |
| 2016/0069713 A1 | 3/2016 | Ruh et al. |
| 2016/0109861 A1 | 4/2016 | Kim et al. |
| 2016/0116306 A1 | 4/2016 | Ferri et al. |
| 2016/0147432 A1 | 5/2016 | Shi et al. |
| 2016/0170598 A1 | 6/2016 | Zambetti et al. |
| 2016/0170608 A1 | 6/2016 | Zambetti et al. |
| 2016/0170624 A1 | 6/2016 | Zambetti et al. |
| 2016/0241688 A1 | 8/2016 | Vossoughi et al. |
| 2016/0253487 A1 | 9/2016 | Sarkar et al. |
| 2016/0306446 A1 | 10/2016 | Chung et al. |
| 2016/0320583 A1 | 11/2016 | Hall, Jr. |
| 2016/0327911 A1 | 11/2016 | Eim et al. |
| 2016/0338642 A1 | 11/2016 | Parara et al. |
| 2016/0378069 A1 | 12/2016 | Rothkopf et al. |
| 2016/0378070 A1 | 12/2016 | Rothkopf et al. |
| 2016/0378071 A1 | 12/2016 | Rothkopf et al. |
| 2017/0011210 A1 | 1/2017 | Cheong et al. |
| 2017/0027461 A1 | 2/2017 | Shin et al. |

(56) References Cited

U.S. PATENT DOCUMENTS

| | | | |
|---|---|---|---|
| 2017/0031449 A1 | 2/2017 | Karsten et al. |
| 2017/0045958 A1 | 2/2017 | Battlogg et al. |
| 2017/0061863 A1 | 3/2017 | Eguchi |
| 2017/0069443 A1 | 3/2017 | Wang et al. |
| 2017/0069444 A1 | 3/2017 | Wang et al. |
| 2017/0069447 A1 | 3/2017 | Wang et al. |
| 2017/0090599 A1 | 3/2017 | Kuboyama |
| 2017/0104902 A1 | 4/2017 | Kim et al. |
| 2017/0139489 A1 | 5/2017 | Chen et al. |
| 2017/0216519 A1 | 8/2017 | Vouillamoz |
| 2017/0216668 A1 | 8/2017 | Burton et al. |
| 2017/0238138 A1 | 8/2017 | Aminzade |
| 2017/0251561 A1 | 8/2017 | Fleck et al. |
| 2017/0269715 A1 | 9/2017 | Kim et al. |
| 2017/0285404 A1 | 10/2017 | Kubota et al. |
| 2017/0301314 A1 | 10/2017 | Kim et al. |
| 2017/0307414 A1 | 10/2017 | Ferri et al. |
| 2017/0331869 A1 | 11/2017 | Bendahan et al. |
| 2017/0357465 A1 | 12/2017 | Dzeryn et al. |
| 2018/0136686 A1 | 5/2018 | Jackson et al. |
| 2018/0196517 A1 | 7/2018 | Tan et al. |
| 2018/0225701 A1 | 8/2018 | Han |
| 2018/0235491 A1 | 8/2018 | Bayley et al. |
| 2018/0239306 A1 | 8/2018 | Ely |
| 2018/0364815 A1 | 12/2018 | Moussette et al. |
| 2019/0017846 A1 | 1/2019 | Boonsom et al. |
| 2019/0072902 A1 | 3/2019 | Ely et al. |
| 2019/0072911 A1 | 3/2019 | Ely et al. |
| 2019/0163324 A1 | 5/2019 | Shedletsky |
| 2019/0250754 A1 | 8/2019 | Ely et al. |
| 2019/0278232 A1 | 9/2019 | Ely et al. |
| 2019/0294117 A1 | 9/2019 | Ely et al. |
| 2019/0391539 A1 | 12/2019 | Perkins et al. |
| 2020/0041962 A1 | 2/2020 | Beyhs |
| 2020/0064774 A1 | 2/2020 | Ely et al. |
| 2020/0064779 A1 | 2/2020 | Pandya et al. |
| 2020/0073339 A1 | 3/2020 | Roach et al. |
| 2020/0110473 A1 | 4/2020 | Bushnell et al. |
| 2020/0159172 A1 | 5/2020 | Bushnell et al. |

FOREIGN PATENT DOCUMENTS

| | | |
|---|---|---|
| CN | 1445627 | 10/2003 |
| CN | 1504843 | 6/2004 |
| CN | 1601408 | 3/2005 |
| CN | 1624427 | 6/2005 |
| CN | 1792295 | 6/2006 |
| CN | 1825224 | 8/2006 |
| CN | 101035148 | 9/2007 |
| CN | 101201587 | 6/2008 |
| CN | 201081979 | 7/2008 |
| CN | 201262741 | 6/2009 |
| CN | 101750958 | 6/2010 |
| CN | 201638168 | 11/2010 |
| CN | 101923314 | 12/2010 |
| CN | 102216959 | 10/2011 |
| CN | 202008579 | 10/2011 |
| CN | 102590925 | 7/2012 |
| CN | 102890443 | 1/2013 |
| CN | 202710937 | 1/2013 |
| CN | 103177891 | 6/2013 |
| CN | 103191557 | 7/2013 |
| CN | 103253067 | 8/2013 |
| CN | 103645804 | 3/2014 |
| CN | 203564224 | 4/2014 |
| CN | 103852090 | 6/2014 |
| CN | 203630524 | 6/2014 |
| CN | 103956006 | 7/2014 |
| CN | 203693601 | 7/2014 |
| CN | 203705837 | 7/2014 |
| CN | 203732900 | 7/2014 |
| CN | 103995456 | 8/2014 |
| CN | 104020660 | 9/2014 |
| CN | 203941395 | 11/2014 |
| CN | 104777987 | 4/2015 |
| CN | 104685794 | 6/2015 |
| CN | 204479929 | 7/2015 |
| CN | 204496177 | 7/2015 |
| CN | 104880937 | 9/2015 |
| CN | 104898406 | 9/2015 |
| CN | 204650147 | 9/2015 |
| CN | 105022947 | 11/2015 |
| CN | 105096979 | 11/2015 |
| CN | 105339871 | 2/2016 |
| CN | 105547146 | 5/2016 |
| CN | 105556433 | 5/2016 |
| CN | 105683876 | 6/2016 |
| CN | 105955519 | 9/2016 |
| CN | 205645648 | 10/2016 |
| CN | 205721636 | 11/2016 |
| CN | 205750744 | 11/2016 |
| CN | 106236051 | 12/2016 |
| CN | 206209589 | 5/2017 |
| CN | 107111342 | 8/2017 |
| CN | 107122088 | 9/2017 |
| CN | 107966895 | 4/2018 |
| DE | 3706194 | 9/1988 |
| DE | 102008023651 | 11/2009 |
| DE | 102016215087 | 3/2017 |
| EP | 0556155 | 8/1993 |
| EP | 1345095 | 9/2003 |
| EP | 1519452 | 3/2005 |
| EP | 1669724 | 6/2006 |
| EP | 1832969 | 9/2007 |
| EP | 2375295 | 10/2011 |
| EP | 2720129 | 4/2014 |
| EP | 2884239 | 6/2015 |
| FR | 2030093 | 10/1970 |
| FR | 2801402 | 5/2001 |
| GB | 2433211 | 6/2007 |
| JP | S52151058 | 12/1977 |
| JP | S52164551 | 12/1977 |
| JP | S53093067 | 8/1978 |
| JP | S54087779 | 6/1979 |
| JP | S5708582 | 1/1982 |
| JP | S5734457 | 2/1982 |
| JP | S60103936 | 6/1985 |
| JP | S60103937 | 6/1985 |
| JP | H02285214 | 11/1990 |
| JP | H04093719 | 3/1992 |
| JP | H04157319 | 5/1992 |
| JP | H05203465 | 8/1993 |
| JP | H05312595 | 11/1993 |
| JP | H06050927 | 12/1994 |
| JP | H06331761 | 12/1994 |
| JP | H06347293 | 12/1994 |
| JP | H07116141 | 5/1995 |
| JP | H10161811 | 6/1998 |
| JP | H11121210 | 4/1999 |
| JP | H11191508 | 7/1999 |
| JP | 2000316824 | 11/2000 |
| JP | 2000337892 | 12/2000 |
| JP | 2001084934 | 3/2001 |
| JP | 2001167651 | 6/2001 |
| JP | 2001202178 | 7/2001 |
| JP | 2001524206 | 11/2001 |
| JP | 2002165768 | 6/2002 |
| JP | 2003050668 | 2/2003 |
| JP | 2003151410 | 5/2003 |
| JP | 2003331693 | 11/2003 |
| JP | 2004184396 | 7/2004 |
| JP | 2005017011 | 1/2005 |
| JP | 2005063200 | 3/2005 |
| JP | 2005099023 | 4/2005 |
| JP | 2005108630 | 4/2005 |
| JP | 2006164275 | 6/2006 |
| JP | 2007101380 | 4/2007 |
| JP | 2007149620 | 6/2007 |
| JP | 2007248176 | 9/2007 |
| JP | 2007311153 | 11/2007 |
| JP | 2008053980 | 3/2008 |
| JP | 2008122124 | 5/2008 |
| JP | 2008122377 | 5/2008 |
| JP | 2008170436 | 7/2008 |

(56) References Cited

FOREIGN PATENT DOCUMENTS

| | | |
|---|---|---|
| JP | 2008235226 | 10/2008 |
| JP | 2009009382 | 1/2009 |
| JP | 2009070657 | 4/2009 |
| JP | 2009519737 | 5/2009 |
| JP | 2009540399 | 11/2009 |
| JP | 2010032545 | 2/2010 |
| JP | 2010515153 | 5/2010 |
| JP | 2010165001 | 7/2010 |
| JP | 2010186572 | 8/2010 |
| JP | 2010243344 | 10/2010 |
| JP | 2010244797 | 10/2010 |
| JP | 2011021929 | 2/2011 |
| JP | 2011165468 | 8/2011 |
| JP | 2011221659 | 11/2011 |
| JP | 2013057516 | 3/2013 |
| JP | 2013079961 | 5/2013 |
| JP | 2013524189 | 6/2013 |
| JP | 3190075 | 4/2014 |
| JP | 5477393 | 4/2014 |
| JP | 2014512556 | 5/2014 |
| JP | 2014174031 | 9/2014 |
| JP | 2018510451 | 4/2018 |
| KR | 20010030477 | 4/2001 |
| KR | 200278568 | 3/2002 |
| KR | 20070011685 | 1/2007 |
| KR | 20070014247 | 2/2007 |
| KR | 100754674 | 9/2007 |
| KR | 20080045397 | 5/2008 |
| KR | 2020100007563 | 7/2010 |
| KR | 20110011393 | 2/2011 |
| KR | 20110012784 | 2/2011 |
| KR | 20110113368 | 10/2011 |
| KR | 20130036038 | 4/2013 |
| KR | 20130131873 | 12/2013 |
| KR | 20140051391 | 4/2014 |
| KR | 20140104388 | 8/2014 |
| KR | 20160017070 | 2/2016 |
| KR | 20160048967 | 5/2016 |
| NL | 1040225 | 11/2014 |
| RO | 0129033 | 11/2013 |
| TW | 200633681 | 10/2006 |
| WO | WO2001/022038 | 3/2001 |
| WO | WO2001/069567 | 9/2001 |
| WO | WO2003032538 | 4/2003 |
| WO | WO2010/058376 | 5/2010 |
| WO | WO2012/083380 | 6/2012 |
| WO | WO2012/094805 | 7/2012 |
| WO | WO2014/018118 | 1/2014 |
| WO | WO2014/200766 | 12/2014 |
| WO | WO2015/147756 | 10/2015 |
| WO | WO2016080669 | 5/2016 |
| WO | WO2016/104922 | 6/2016 |
| WO | WO2016/155761 | 10/2016 |
| WO | WO2016196171 | 12/2016 |
| WO | WO2016208835 | 12/2016 |
| WO | WO2017/013278 | 1/2017 |

OTHER PUBLICATIONS

Author Unknown, "Fossil Q ups smartwatch game with handsome design and build," Business Mirror, Makati City, Philippines, 3 pages, Dec. 20, 2016.
Author Unknown, "How Vesag Helps Kids Women and Visitors," http://www.sooperarticles.com/health-fitness-articles/children-health-articles/how-vesag-helps-kids-women-visitors-218542.html, 2 pages, at least as early as May 20, 2015.
Author Unknown, "mHealth," http://mhealth.vesag.com/?m=201012, 7 pages, Dec. 23, 2010.
Author Unknown, "mHealth Summit 2010," http://www.virtualpressoffice.com/eventsSubmenu.do?page=exhibitorPage&showId=1551&companyId=5394, 5 pages, Nov. 18, 2010.
Author Unknown, "MyKronoz ZeTime: World's Most Funded Hybrid Smartwatch Raised over $3M on Kickstarter, Running until Apr. 27," Business Wire, New York, New York, 3 pages, Apr. 21, 2017.
Author Unknown, "RedEye mini Plug-in Universal Remote Adapter for iPhone, iPod touch and iPad," Amazon.com, 4 pages, date unknown.
Author Unknown, "Re iPhone Universal Remote Control—Infrared Remote Control Accessory for iPhone and iPod touch," http://www.amazon.com/iPhone-Universal-Remote-Control-Accessory/dp/tech-data/B0038Z4 . . . , 2 pages., at least as early as Jul. 15, 2010.
Author Unknown, "Vesag Wrist Watch for Dementia Care from VYZIN," http://vyasa-kaaranam-ketkadey.blogspot.com/2011/03/vesag-wrist-watch-for-dementia-care.html, 2 pages, Mar. 31, 2011.
Author Unknown, Vyzin Electronics Private Limited launches "Vesag Watch," http://www.virtualpressoffice.com/showJointPage.do?page=jp&showId=1544, 5 pages, Jan. 6, 2011.
Author Unknown, "Vyzin Unveiled Personal Emergency Response System (PERS) with Remote Health Monitoring That Can Be Used for Entire Family," http://www.24-7pressrelease.com/press-release/vyzin-unveiled-personal-emergency-response-system-pers-with-remote-health-monitoring-that-can-be-used-for-entire-family-219317.php, 2 pages, Jun. 17, 2011.
Author Unknown, "DeskThorityNet, Optical Switch Keyboards," http://deskthority.net/keyboards-f2/optical-switch-keyboards-t1474.html, 22 pages, Jul. 11, 2015.
Epstein et al., "Economical, High-Performance Optical Encoders," Hewlett-Packard Journal, pp. 99-106, Oct. 1988. [text only version].
GreyB, "Google Watch: Convert your arm into a keyboard," http://www.whatafuture.com/2014/02/28/goog le-smartwatch/#sthash.Yk35cDXK.dpbs, 3 pages, Feb. 28, 2014.
IBM, "Additional Functionality Added to Cell Phone via "Learning" Function Button," www.ip.com, 2 pages, Feb. 21, 2007.
Kim, Joseph, "2010 mHealth Summit Emerges as Major One-Stop U.S. Venue for Mobile Health," http://www.medicineandtechnology.com/2010/08/2010-mhealth-summit-emerges-as-major.html, 3 pages, Aug. 26, 2010.
Krishnan et al., "A Miniature Surface Mount Reflective Optical Shaft Encoder," Hewlett-Packard Journal, Article 8, pp. 1-6, Dec. 1996.
Rick, "How VESAG Helps Health Conscious Citizens," http://sensetekgroup.com/2010/11/29/wireless-health-monitoring-system/, 2 pages, Nov. 29, 2010.
Sadhu, Rajendra, "How VESAG Helps People Who Want to 'Be There'?," http://ezinearticles.com/?How-Vesag-Helps-People-Who-Want-to-Be-There?&id-5423873, 1 page, Nov. 22, 2010.
Sadhu, Rajendra, "Mobile Innovation Helps Dementia and Alzheimer's Patients," http://www.itnewsafrica.com/2010/11/mobile-innovation-helps-dementia-andalzheimer%E2%80%99s-patients/, 3 pages, Nov. 22, 2010.
Sherr, Sol, "Input Devices," p. 55, Mar. 1988.
Tran et al., "Universal Programmable Remote Control/Telephone," www.ip.com, 2 pages, May 1, 1992.
U.S. Appl. No. 16/840,336, filed Apr. 4, 2020, pending.
U.S. Appl. No. 16/872,600, filed May 12, 2020, pending.
U.S. Appl. No. 16/890,880, filed Jun. 2, 2020, pending; and.
U.S. Appl. No. 16/912,981, filed Jun. 26, 2020.

* cited by examiner

WEARABLE ELECTRONIC DEVICE

CROSS-REFERENCE TO RELATED APPLICATIONS

This application is a continuation patent application of U.S. patent application Ser. No. 15/261,912, filed Sep. 10, 2016, and titled "Wearable Electronic Device," U.S. patent U.S. patent application Ser. No. 15/261,917, filed Sep. 10, 2016, and titled "Wearable Electronic Device," and U.S. patent application Ser. No. 14/842,617, filed Sep. 1, 2015, and titled "Wearable Electronic Device," which is a non-provisional patent application of and claims the benefit of U.S. Provisional Patent Application No. 62/044,974, filed Sep. 2, 2014, and titled "Wearable Electronic Device and Associated Methods of Use and Manufacture," the disclosures of which are hereby incorporated herein by reference in their entireties.

FIELD

The following disclosure generally relates to an electronic device, and more specifically to a wearable electronic device having a range of features, including touch input, force input, an interchangeable attachment system, health monitoring functionality, wireless power charging, wireless authentication and transaction functionality, and other features and functionality.

BACKGROUND

Portable electronic devices have become increasingly popular, and the features and functionality provided by portable electronic devices continue to expand to meet the needs and expectations of many consumers. However, some traditional portable electronic devices, particularly wearable electronic devices, may have relatively limited functionality or are only able to perform a specialized set of functions or tasks. For example, some traditional electronic wristwatches may be configured to perform a relatively limited set of functions, including displaying time, date, and performing basic timing functions. The embodiments described herein are directed to a wearable electronic device that provides a wide range of functionality, as compared to some traditional wearable electronic devices.

SUMMARY

The embodiments included herein are directed to a consumer product, which may include a portable or wearable electronic device that is configured to provide an expansive feature set integrated or incorporated into a compact form factor. In some aspects of the present disclosure, a consumer product may integrate or combine multiple subsystems into a single device to provide a wide range of functionality, including biometric sensing, touch-based user input, near-field communications, and other desirable features. In some aspects, multiple subsystems are integrated into the relatively compact space of a wrist-worn device.

Some example embodiments are directed to wearable electronic device having a housing that includes a flat bottom portion, a top portion defining a cavity, and a curved side portion that extends from the bottom portion to the top portion. A band may be attached to the housing and configured to secure the wearable electronic device to a user. A display may be at least partially disposed within the cavity and may have a viewable area. The device may also include a cover disposed above the display and including a flat middle portion larger than the viewable area of the display, a curved edge portion surrounding the flat middle portion and coinciding with the curved side portion along a perimeter of the cavity to form a continuous contoured surface.

In some embodiments, the continuous contoured surface is tangent with the flat bottom portion of the housing at a first end of the contour. The continuous contoured surface may also be tangent with the flat middle portion of the cover at a second end of the contour. In some embodiments, the continuous contoured surface has a constant radius.

In some embodiments, the cavity has a rectangular shape. The curved edge portion of the housing may have four sides that surround the cavity, each side is orthogonal to two adjacent sides. Each side may be connected to an adjacent side by a rounded corner. In some embodiments, the rounded corners have a curvature that corresponds to a curvature of the continuous contoured surface formed by the curved edge portion of the cover and the curved side portion of the housing.

Some embodiments include a crown module that is positioned at least partially within an aperture formed within the curved side portion of the housing. The crown module may include an outer surface configured to receive a rotary user input. The crown module may be offset with respect to a centerline of the housing between the top portion and the flat bottom portion. The offset may be toward the top portion of the housing. The crown module may include a dial having a portion that is higher than an interface between the cover and the housing.

In some example embodiments, a port is formed in the curved side portion of the housing. An acoustic module may be disposed within the housing and configured to produce an audio output through the port. The acoustic module may include an acoustic element and an acoustic cavity that acoustically couples the acoustic element to the port. The port may include an orifice that is offset with respect to the acoustic cavity to prevent the direct ingress of liquid into the acoustic module.

In some embodiments, the device includes a gasket positioned between the housing and the cover. The housing may also include a ledge formed along a perimeter of the cavity. The gasket may be positioned along the ledge that is formed along the perimeter of the cavity. The gasket, the cover, and the housing may be configured to cooperate to form a substantially water-proof seal.

In some example embodiments, the device includes a biosensor module that is disposed in an opening formed in the flat bottom portion of the housing. The biosensor module may include a chassis positioned in the opening of the housing and defining an array of windows. An array of light sources may be attached to the chassis and configured to emit light into the user through the array of windows. The biosensor module may also include an optically transparent rear cover disposed over the chassis and over the array of windows and operative to pass light emitted from the array of light sources into the user. In some embodiments, the rear cover has a convex outer contour.

Some example embodiments are directed to an electronic device having a housing comprising a bottom portion defining an opening and a band attached to the housing and configured to secure the electronic device to a user. A biosensor module may be disposed within the opening of the housing. A rear cover may be disposed over the biosensor module and may include an edge protruding outwardly from the bottom portion of the housing and an outer surface having a convex curved contour. In some embodiments, the outer surface of the rear cover defines one or more windows that provide operational access to one or more optical components of the biosensor module. The one or more windows may have a curvature that matches the convex curved contour of the outer surface.

In some embodiments, the biosensor module includes an array of light sources that are configured to emit light into a body of the user. The biosensor module may also include a photodetector configured to receive light produced by a light source of the array of light sources that is reflected from the body and produce a sensor signal. In some cases, the biosensor module is removably coupled to the housing.

In some embodiments, the device also includes a processing unit configured to compute a health metric associated with the user based on the sensor signal. The device may also include a display disposed within the housing and configured to display the health metric.

Some example embodiments are directed to a wearable electronic device, having a housing including a top portion, a cavity formed within the top portion, and a curved side portion that surrounds the cavity. The device may also include a transparent cover disposed over the cavity of the housing and may include a flat middle portion at a center of the transparent cover, a curved outer portion that emanates from and surrounds the flat middle portion and extends outwardly to an edge of the transparent cover, and a mask positioned relative to an internal surface of the transparent cover. The mask may have an outer boundary located proximate to the edge of the transparent cover and an inner boundary located within the curved outer portion of the transparent cover.

In some embodiments, the device includes a display disposed below the transparent cover. A perimeter portion of a viewable area of the display may be disposed below the mask. The device may also include an antenna having a shape that corresponds to a shape of the cavity formed within the housing. The antenna may be disposed in a groove formed in the internal surface of the transparent cover. The groove may be formed between the outer boundary and the inner boundary of the mask. In some embodiments, the cover is formed from a sapphire material. The antenna may be configured to facilitate wireless communication between the wearable electronic device and an external device.

Some example embodiments are directed to an electronic device having a housing including a first end, a second end opposite the first end, a first side extending between the first and second ends, and a second side opposite to the first side and extending between the first and second ends. The first end may define a first groove extending between the first and second sides and may be configured to receive a first lug portion of a first band. The second end may define a second groove extending between the first and second sides and may be configured to receive a second lug portion of a second band. The first and second grooves may have an inwardly curved concave shape with an undercut feature that retains the first and second lug portions. In some embodiments, the first groove extends through a solid portion of the housing to form a continuous interior shape.

In some embodiments, the device includes a display at least partially disposed within a cavity of the housing. A cover may be disposed above the display and at least a portion of the first groove is disposed below the cover. The first and second grooves may be formed at an angle with respect to a centerline of the housing. The first and second grooves may be angled upward toward a top of the housing and inward toward the center of the housing. The first and second grooves may cross the centerline of the housing.

Some example embodiments are directed to a wearable electronic device including a housing and a band attached to the housing and configured to secure the wearable electronic device to a user. A crown may be disposed relative to the housing and configured to receive a rotational input. An encoder may be operatively coupled to the crown and configured to produce an encoder output that corresponds to the rotational input. A speaker module may be disposed within the housing and configured to produce an audio output that corresponds to the encoder output. A haptic device may be disposed within the housing and configured to produce a haptic output that corresponds to the encoder output. In some embodiments, the haptic output is synchronized with the audio output. The crown may be further configured to translate along an axis and actuate a tactile switch.

In some embodiments, the device also includes a display element within the housing. The device may be configured to display a list of items on the display element and scroll the list of items in response to the encoder output. The device may also be configured to synchronize the audio and haptic outputs with the scrolling of the list of items. In some embodiments, the crown is further configured to translate along an axis and actuate a tactile switch. The crown may be operative to select an item of the list of items when the tactile switch is actuated.

Some example embodiments are directed to a wearable electronic device having a housing that includes a bottom portion and an aperture formed in the bottom portion. A band may be attached to the housing and configured to secure the wearable electronic device to a user. A biosensor module may be disposed in the aperture of the housing. The biosensor module may include an array of light sources configured to emit light into a body of the user, and a photodetector configured to receive light produced by a light source of the array of light sources that is reflected from the body and produce a sensor signal. The device may also include a processing unit that is configured to compute a health metric associated with the user based on the sensor signal. A display may be disposed within the housing and configured to display the health metric.

In some embodiments, the array of light sources and the photodetector are configured to function as multiple photoplethysmography (PPG) sensors. Each PPG sensor may be configured to be used to compute a separate health metric. In some embodiments, a first light source of the array of light sources includes a green LED adapted to detect blood perfusion in the body. A second light source of the array of light sources may include an infrared LED adapted to detect water content of the body. The health metric may include one or more of: a heart rate, a respiration rate, a blood oxygenation level, and a blood volume estimate.

In some embodiments, the device also includes at least one pair of electrodes disposed on an exterior surface of the housing. The at least one pair of electrodes may be configured to produce a signal when the at least one pair of electrodes is in contact with the body. In some case, the signal is used to compute an additional health metric that includes one or more of: a heart function, a body fat estimate, and a body fat estimate.

Some example embodiments are directed to a wearable electronic device including a housing and a band attached to the housing and configured to secure the wearable electronic device to a user. The device may also include an array of light emitting diodes (LEDs) disposed within the housing, the array of LEDs being configured to emit light. A photodetector may be disposed within the housing and configured to receive light produced by an LED of the array of LEDs that is reflected from a body of the user and produce a first sensor signal in response to the received light. The device may also include at least one pair of electrodes disposed on an exterior surface of the wearable electronic device. The electrodes may be configured to produce a second sensor signal when the electrodes are in contact with a respective portion of the body. The device may also include a processing unit that is configured to compute one or more health metrics based on the first and second sensor signals. The device may also include a display disposed at least partially within the housing and configured to display the one or more health metrics.

Some example embodiments are directed to a wearable electronic device including a housing and a band attached to the housing and configured to secure the wearable electronic device to a user. A cover may be disposed relative to the housing and a display may be attached to a lower surface of the cover. A force sensor may be positioned between the cover and the housing and attaching the cover to the housing. The force sensor may be configured to detect the force of a touch on the cover. The force sensor may also form a barrier to prevent ingress of liquid into the wearable electronic device. In some embodiments, an antenna may be disposed relative to the cover and external from the housing. The antenna may be configured to facilitate wireless communication with an external device.

In some example embodiments, a wearable electronic device may include a housing and a band attached to the housing and configured to secure the wearable electronic device to a user. A display element may be positioned within the housing and a rechargeable battery may be disposed within the housing and operatively coupled to the display element. The device may also include a receive coil within the housing configured to inductively couple with an external transmit coil. A power conditioning circuit may be configured to recharge the rechargeable battery using power received by the receive coil. The power conditioning circuit may be configured to provide power to the display element. The device may also include a first alignment magnet positioned within the receive coil and configured to align the device with respect to a second alignment magnet positioned within the external transmit coil.

Some example embodiments are directed to a wearable electronic device that includes a housing and a band attached to the housing and configured to secure the wearable electronic device to a user. A cover may be positioned relative to the housing and a display may be disposed within the housing and below the cover. A force sensor may be disposed within the housing and configured to detect a force of a touch on the cover. A touch sensor may be disposed between the display and the cover. The touch sensor may be configured to detect a location of the touch on the cover. In some embodiments, the force sensor is disposed along a perimeter of the display. The device may also include a processing unit and memory disposed within the housing. The processing unit may be configured to interpret a touch gesture on a surface of the cover using a force output from the force sensor and a touch output from the touch sensor.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
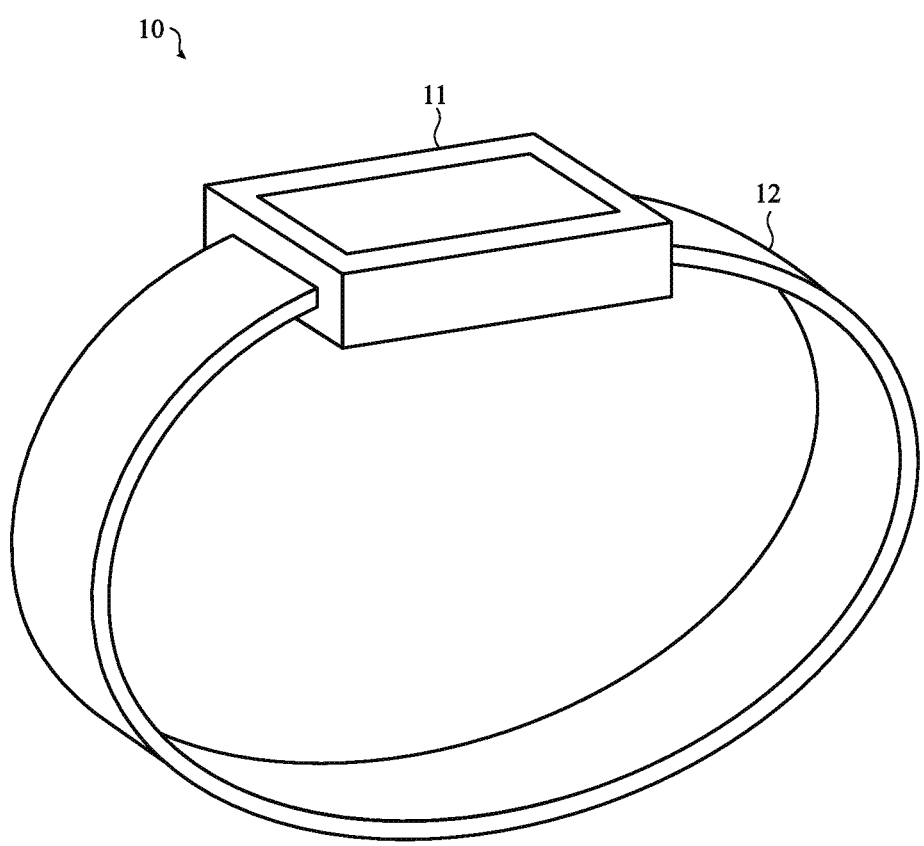
FIG. 1 depicts an example wearable electronic device having a device body and band.

Provided herein are descriptions and examples of a consumer product, which may include a portable electronic device, a wearable electronic device, or other type of device. By way of example and not by way of limitation, the consumer product may be an electronic device, a mechanical device, or an electromechanical device. Specific example devices include mobile phones, personal digital assistants, music players, timekeeping devices, health monitoring devices, tablet computers, laptop computers, glasses (electronic or otherwise), portable storage devices, and the like.

In one particular embodiment, the consumer product is a portable and, more specifically, a wearable consumer product. A wearable consumer product is one that can be worn by or otherwise secured to a user. For example, the consumer product may be a wearable electronic device including, but not limited to, a wearable computer, a wearable watch, a wearable communication device, a wearable media player, a wearable health monitoring device, and the like. A wearable consumer product may be worn by a user in a variety of ways. In some examples, the consumer product is a wrist-worn product and may include a band that can be wrapped around a user's wrist to secure the consumer product to the user's body. The device may include one or more other types of attachments including, for example, an armband, lanyard, waistband, chest strap, and the like.

Some aspects of the disclosure are directed to a wearable electronic device having improved functionality and/or versatility as compared to some traditional wearable devices. For example, some aspects of the disclosure are directed to a consumer product, such as a portable electronic device, having an expansive feature set integrated or incorporated into a compact form factor. In some aspects of the present disclosure, a consumer product may integrate or combine multiple subsystems into a single device to provide a wide range of functionality, including biometric sensing, touch-based user input, near-field communications, and other desirable features. In some aspects, multiple subsystems are integrated into the relatively compact space of a wrist-worn device. Some aspects of the following disclosure are directed to the integration of a variety of subsystems or modules to provide functionality that may not be possible using some traditional device platforms. In some cases, the configuration and/or functionality provided by the various subsystems may be configurable by the end user, the manufacturer, and/or a vendor of the device. Example subsystems or modules of a consumer product and their respective functions are described below with respect to FIGS. 2 and 3.

Some aspects of the disclosure are directed to a consumer product that is configured to communicate wirelessly with any of a number of other devices, such as a mobile phone, computer, tablet computing devices, personal media players, televisions, networked home appliances, networked home controls, electronic systems in vehicles, and so on. Through wireless communication with other devices, the consumer product may transmit and/or receive various notifications, messages, or other information between devices. The wireless communication may also facilitate the relay of alerts or other device outputs to notify the user of an event or action. In some aspects, the consumer product may communicate wirelessly with any of a number of electronic accessories, including headset devices, portable speaker devices, portable microphone devices, display screens, and so on. An example communication system is described below with respect to FIG. 4 and with respect to other examples provided herein.

In some aspects, the consumer product may include a system of interchangeable components used to attach or secure the consumer product to the user. The system of interchangeable components may include a set of interchangeable bands or attachment devices that are configured to connect or attach to a receiving feature on the body of the product. The receiving feature may be standardized within the system of interchangeable components and allow multiple types of bands or attachment devices to be used with the same housing or body. The system of interchangeable components may also allow for an interchange between different bodies, which may include different types of electronic devices or other consumer products. Each body of the different devices or products may have a similar receiving feature that is standardized within the system of interchangeable components. An example system of interchangeable components is described below with respect to FIG. 5 and with respect to other examples provided herein.

Some aspects of the present disclosure are directed to a consumer product that includes a body that includes a case or housing used to protect as well as support the internal components of the product in their assembled position. The housing may enclose and support various components, including, for example, integrated circuits, subsystems, modules, and other internal components of the device. In some aspects, the housing forms a water-resistant or waterproof barrier and also provides structural rigidity necessary to protect internal components. The housing may be formed as a single piece, which may enhance the structural rigidity, water impermeability, and manufacturability of the housing. An example housing and example internal components for a consumer product are provided below with respect to FIGS. 6-8 and with respect to other examples provided herein.

In some aspects, the consumer product includes a force sensor that is configured to detect and measure the magnitude of a force or pressure on a surface of the product. In some implementations, the force sensor includes a capacitive-based sensor that is configured to estimate the force based on a deflection or movement between capacitive plates that is caused by and correlates to the amount of force caused by a touch. In some implementations, the force sensor is a resistance- or charge-based sensor that is configured to estimate the force based on the deflection of a sheet or film that is positioned relative to the touch-sensitive surface of the product. In some implementations, the output from the force sensor is combined with the output from a touch sensor, which may be self-capacitive or mutually capacitive, or a combination of the two. Example force and touch sensors are described below with respect to FIGS. 9-15B and with respect to other examples provided herein.

In some aspects, the consumer product includes one or more biosensors. The biosensors may include optical and/or electronic biometric sensors that may be used to compute one or more health metrics. Example health metrics include, without limitation, a heart rate, a respiration rate, blood oxygenation level, a blood volume estimate, blood pressure, or a combination thereof. In some embodiments, the biosensors include an electrical sensor that may be used to measure electrocardiographic (ECG) characteristics, galvanic skin resistance, and other electrical properties of the user's body. An example consumer product having multiple biosensors is described below with respect to FIG. 16 and with respect to other examples herein.

In some aspects, the consumer product is configured to perform wireless communication with an external device. In some implementations, the wireless communication may include a Near Field Communication (NFC) interface. The NFC interface may be used to identify the device and initiate a secure data connection, which may be used to authorize transactions, purchases, or conduct other forms of e-commerce. An example consumer product having wireless communications with an external device is described in more detail below with respect to FIG. 17 and with respect to other examples herein.

In some aspects, the consumer product is configured to recharge an internal battery using a wireless charging system. In some implementations, the consumer product includes one or more receiving inductive coils that are configured to cooperate with one or more transmitting inductive coils that are located in a charging dock or other external device. The wireless charging system may allow the transfer of power and/or wireless communications with the consumer product without the use of an external port or terminal connection. An example consumer product having wireless charging capabilities is described in more detail below with respect to FIGS. 18-19 and with respect to other examples herein.

In some aspects, the consumer product includes one or more acoustic modules that are configured to function as a speaker and/or a microphone for the product. The speaker and/or microphone may include features that enhance the water/liquid resistance or impermeability of the consumer product. The consumer product may also include a haptic module or actuator that is configured to produce a haptic output that may be perceived by the user. In some implementations, the output of an acoustic module, such as a speaker, and the haptic module may be used to provide feedback or an alert to the user. In some cases, an acoustic module and the haptic module provide feedback to the user and may be coordinated with a user input, such as user-interface selecting, user-interface scrolling, or other user input command. An example acoustic module is described below with respect to FIG. 20 and an example haptic module is described below with respect to FIGS. 22A-B.

In some aspects, the consumer product includes a dial or crown that is coupled to an encoder or other rotary sensor for detecting a rotary input. In some implementations, the output from the optical encoder is used to drive an aspect of a user interface or control other functionality of the product. Additionally, the dial or crown may include a tactile switch that can be actuated by pressing inward on the dial or crown. An example consumer product having a crown is described below with respect to FIGS. 23-24B and with respect to other examples herein.

The description that follows includes sample devices, components, modules, systems, methods, and apparatuses that embody various elements of the present disclosure. However, it should be understood that various elements of the described disclosure may be combined and/or practiced in a variety of forms in addition to those described herein. In particular, the modules and components are described in a particular combination with respect to some examples provided below. However other combinations are possible, which may be achieved by adding, removing, and/or re-arranging modules to obtain a device or system having the desired characteristics.

FIG. 1 depicts a wearable consumer product 10. For example, the consumer product 10 may be a wearable electronic device. In one example, the consumer product 10 may be a wearable multifunctional electronic device including multiple functionalities such as time keeping, health monitoring, sports monitoring, medical monitoring, communications, navigation, computing operations, and/or the like. The functionalities may include but are not limited to: keeping time; monitoring a user's physiological signals and providing health-related information based on those signals; communicating (in a wired or wireless fashion) with other electronic devices or services, which may be different types of devices having different functionalities; providing alerts to a user, which may include audio, haptic, visual and/or other sensory output, any or all of which may be synchronized with one another; visually depicting data on a display; gathering data form one or more sensors that may be used to initiate, control, or modify operations of the device; determining a location of a touch on a surface of the device and/or an amount of force exerted on the device, and using either or both as input; accepting voice input to control one or more functions; accepting tactile input to control one or more functions; capturing and transmitting images; and so on. These and other functions and features will be described in more detail herein.

The wearable consumer product 10 can take a variety of forms. In one example, the consumer product 10 may be a wrist-worn electronic device. The device may include a variety of types of form factors including, wristbands, armbands, bracelets, jewelry, and/or the like.

In the illustrated embodiment, the consumer product 10 includes a device body 11. The device body 11 may include a housing that carries, encloses and supports both externally and internally various components (including, for example. integrated circuit chips and other circuitry) to provide computing and functional operations for the consumer product 10. The components may be disposed on the outside of the housing, partially within the housing, through the housing, completely inside the housing, and the like. The housing may, for example, include a cavity for retaining components internally, holes or windows for providing access to internal components, and various features for attaching other components. The housing may also be configured to form a water-resistant or water-proof enclosure for the body 11. For example, the housing may be formed from as a single unitary body and the openings in the unitary body may be configured to cooperate with other components to form a water-resistant or water-proof barrier.

Examples of components that may be contained in the device body 11 include processing units, memory, display, sensors, biosensors, speakers, microphones, haptic actuators, batteries, and so on. In some cases, the device body 11 may take on a small form factor. In cases such as these, the components may be packaged and/or in order to provide the most functionality in the smallest space. The components may also be configured to take up a minimal amount of space, which may facilitate the device body 11 having a small form factor. Additionally, the integration and assembly of the various components may be configured to enhance the reliability of the consumer product 10.

The construction of the housing of the device body 11 may be widely varied. For example, housing may be formed from a variety of materials including plastic, rubber, wood, silicone, glass, ceramics, fiber composites, metal or metal alloys, (e.g., stainless steel, aluminum), precious metals (e.g., gold, silver), or other suitable materials, or a combination of these materials.

Also in the illustrated embodiment, the wearable electronic device includes a band 12 or strap or other means for attaching to a user. The band 12 may, for example, be configured to attach to the body and provide a loop for securing to the wrist of the user. The band 12 may be integral with the housing or it may be a separate part. If integral, the band 12 may be a continuation of the housing. In some cases, the integral band may be formed from the same material as the housing. If the band 12 is separate, the band may be fixed or releasably coupled to the housing. In both cases, the band 12 may be formed from similar or different materials as the housing. In most cases, the band 12 is formed from a flexible material such that it can conform to a user's body. Furthermore, the band 12 itself may be a single integral part or it may include attachment ends that provide an open and closed configuration. The attachment ends may, for example, be manifested as a clasp or other similar attachment mechanism or device. This particular configuration allows a user to open the band 12 for placement on the arm and close the band 12 in order to secure the band and body to the arm. The band 12 may be widely varied. By way of example, they may be formed from rubber, silicone, leather, metal, mesh, links and/or the like.

Figure 2:
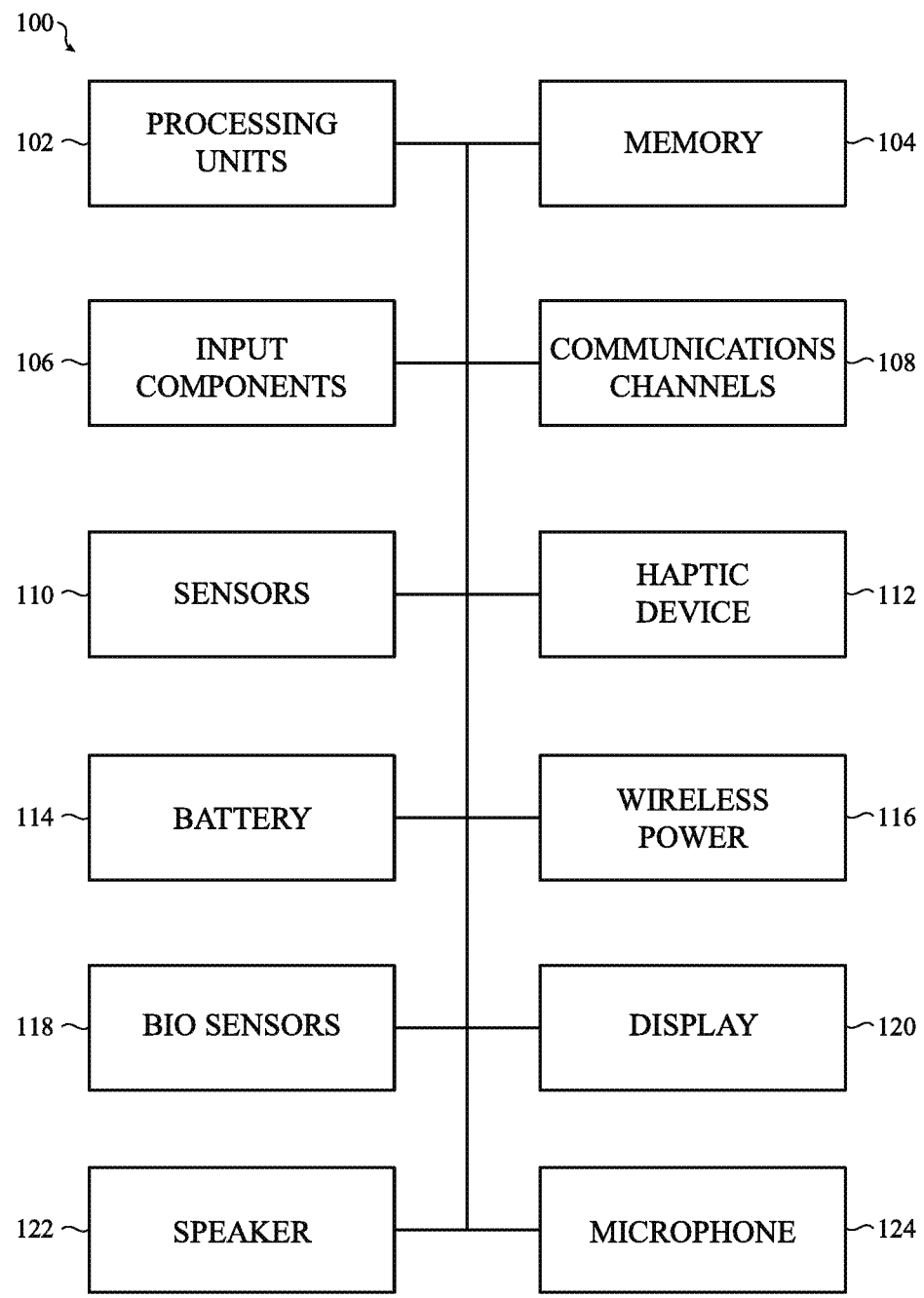
FIG. 2 depicts an example schematic diagram of a wearable electronic device.

FIG. 2 depicts an example schematic diagram of a wearable electronic device. By way of example, device 100 of FIG. 2 may correspond to the consumer product 10 shown in FIG. 1. To the extent that multiple functionalities, operations, and structures are disclosed as being part of, incorporated into, or performed by device 100, it should be understood that various embodiments may omit any or all such described functionalities, operations, and structures. Thus, different embodiments of the device 100 may have some, none, or all of the various capabilities, apparatuses, physical features, modes, and operating parameters discussed herein.

As shown in FIG. 2, the device 100 includes one or more processing units 102 that are configured to access a memory 104 having instructions stored thereon. The instructions or computer programs may be configured to perform one or more of the operations or functions described with respect to the device 100. For example, the instructions may be configured to control or coordinate the operation of a display 120, one or more input/output components 106, one or more communication channels 108, one or more sensors 110, a speaker 122, a microphone 124 and/or one or more haptic feedback devices 112.

The processing units 102 of FIG. 2 may be implemented as any electronic device capable of processing, receiving, or transmitting data or instructions. For example, the processing units 102 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

The memory 104 can store electronic data that can be used by the device 100. For example, a memory can store electrical data or content such as, for example, audio and video files, documents and applications, device settings and user preferences, timing and control signals or data for the various modules, data structures or databases, and so on. The memory 104 can be configured as any type of memory. By way of example only, the memory can be implemented as random access memory, read-only memory, Flash memory, removable memory, or other types of storage elements, or combinations of such devices.

In the schematic diagram of FIG. 2, the one or more input components 106 are represented as a single item within the schematic diagram. However, input components 106 may represent a number of different input components, including buttons, switches, and dials for accepting user input, and so on. More specifically, the input components 106 may correspond to the buttons, dials, crowns or other devices for receiving input. Generally, the input components 106 are configured to translate a user-provided input into a signal or instructions that may be accessed using instructions executed on the processing units 102. In the present example, the input components 106 may include the hardware configured to receive the user input (e.g., button, switch, crown, and encoder) which is operatively coupled to circuitry and firmware used to generate signals or data that are able to be accessed using processor instructions. Each input component 106 may include specialized circuitry for generating signals or data and, additionally or alternatively, circuitry and firmware for generating signals or data may be shared between multiple input components 106. In some cases, the input components 106 produce user-provided feedback for application-specific input that corresponds to a prompt or user interface object presented on display 120. For example, the crown (item 642 of FIG. 6) may be used to receive rotational input from the user, which may be translated into an instruction to scroll a list or object presented on the display 120. The input components 106 may also produce user input for system-level operations. For example the input components 106 may be configured to interact directly with hardware or firmware being executed on the device 100 for system-level operations, including, without limitation, power on, power off, sleep, awake, and do-not-disturb operations.

As shown in FIG. 2, the device 100 may also include one or more acoustic elements, including a speaker 122 and a microphone 124. The speaker 122 may include drive electronics or circuitry and may be configured to produce an audible sound or acoustic signal in response to a command or input. Similarly, the microphone 124 may also include drive electronics or circuitry and is configured to receive an audible sound or acoustic signal in response to a command or input. The speaker 122 and the microphone 124 may be acoustically coupled to respective ports or openings in the housing that allow acoustic energy to pass, but may prevent the ingress of liquid and other debris. As shown in FIG. 2, the speaker 122 and microphone 124 are also operatively coupled to the processing units 102, which may control the operation of the speaker 122 and microphone 124. In some cases, the processing units 102 are configured to operate the speaker 122 to produce an acoustic output that corresponds to an application or system-level operation being performed on the device 100. In some cases, the speaker 122 is operatively coupled to other modules, including, for example, input components 106, such as a crown or button. In some implementations, the device 100 is configured to produce an audible output that corresponds to the operation of the crown or buttons using the speaker 122. The microphone 124 may be configured to produce an output or signal in response to an acoustic stimulus. For example, the microphone 124 may be operatively coupled to the memory 104 and may be configured to record audio input, including human speech, music, or other sounds. In some cases, the microphone 124 may be configured to receive voice signals, which may be interpreted as voice commands by the processing units 102.

The one or more communication channels 108 may include one or more wireless interface(s) that are adapted to provide communication between the processing unit(s) 102 and an external device. In general, the one or more communication channels 108 may be configured to transmit and receive data and/or signals that may be interpreted by instructions executed on the processing units 102. In some cases, the external device is part of an external communication network that is configured to exchange data with wireless devices. Generally, the wireless interface may include, without limitation, radio frequency, optical, acoustic, and/or magnetic signals and may be configured to operate over a wireless interface or protocol. Example wireless interfaces include radio frequency cellular interfaces, fiber optic interfaces, acoustic interfaces, Bluetooth interfaces, infrared interfaces, USB interfaces, Wi-Fi interfaces, TCP/IP interfaces, network communications interfaces, or any conventional communication interfaces.

In some implementations, the one or more communications channels 108 may include a dedicated wireless communication channel between the device 100 and another user device, such as a mobile phone, tablet, computer, or the like. In some cases, output, including audio sounds or visual display elements, are transmitted directly to the other user device for output to the user. For example, an audible alert or visual warning may be transmitted to a user's mobile phone for output on that device. Similarly, the one or more communications channels 108 may be configured to receive user input provided on another user device. In one example, the user may control one or more operations on the device 100 using a user interface on an external mobile phone, table, computer, or the like.

Additionally, as described in more detail below with respect to FIG. 17, the communications channels 108 may include a Near Field Communication (NFC) interface. The NFC interface may be used to identify the device and initiate a secure data connection, which may be used to authorize transactions, purchases, or conduct other forms of e-commerce.

As shown in FIG. 2, the device 100 also includes one or more sensors 110 represented as a single item within the schematic diagram. However, the sensors 110 may represent a number of different sensors, including devices and components that are configured to detect environmental conditions and/or other aspects of the operating environment. Example sensors 110 include an ambient light sensor (ALS), proximity sensor, temperature sensor, barometric pressure sensor, moisture sensor, and the like. Thus, the sensors 110 may also be used to compute an ambient temperature, air pressure, and/or water ingress into the device. In some embodiments, the sensors 110 may include one or more motion sensors for detecting movement and acceleration of the device 100. The one or more motion sensors may include one or more of the following: an accelerometer, a gyroscope, a tilt sensor, or other type of inertial measurement device.

The device 100 also includes one or more biosensors 118 and may include optical and/or electronic biometric sensors that may be used to compute one or more health metrics. As described in more detail below with respect to FIG. 16, one or more of the biosensors 118 may include a light source and a photodetector to form a photoplethysmography (PPG) sensor. The optical (e.g., PPG) sensor or sensors may be used to compute various health metrics including, without limitation, a heart rate, a respiration rate, blood oxygenation level, a blood volume estimate, blood pressure, or a combination thereof. One or more of the biosensors 118 may also be configured to perform an electrical measurement using one or more electrodes. The electrical sensor(s) may be used to measure electrocardiographic (ECG) characteristics, galvanic skin resistance, and other electrical properties of the user's body. Additionally or alternatively, one or more of the biosensors 118 may be configured to measure body temperature, exposure to UV radiation, and other health-related information.

The device 100 may also include one or more haptic devices 112. The haptic device 112 may include one or more of a variety of haptic technologies such as, but not necessarily limited to, rotational haptic devices, linear actuators, piezoelectric devices, vibration elements, and so on. In general, the haptic device 112 may be configured to provide punctuated and distinct feedback to a user of the device. More particularly, the haptic device 112 may be adapted to produce a knock or tap sensation and/or a vibration sensation. As shown in FIG. 2, the haptic device 112 may be operatively coupled to the processing unit 102 and memory 104. In some embodiments, the haptic device 112 may be directly controlled by the processing unit 102. In some embodiments, the haptic device 112 may be controlled, at least in part, by the operation of an input component 106, including, for example, a button, dial, crown, or the like. The operation of the haptic device 112 may also be paired or linked to the operation of one or more other output devices, including, for example, the display 120 or the speaker 122.

As shown in FIG. 2, the device 100 may include a battery 114 that is used to store and provide power to the other components of the device 100. The battery 114 may be a rechargeable power supply that is configured to provide power to the device 100 while it is being worn by the user. The device 100 may also be configured to recharge the battery 114 using a wireless charging system. Accordingly, in some cases, the device may include a wireless power module 116 that may be configured to receive power from an external device or dock. The wireless power module 116 may be configured to deliver power to components of the device, including the battery 114. The wireless power module 116 and an external charging station or dock may also be configured to transmit data between the device and a base or host device. In some cases, the wireless power module 116 may interface with the wireless charging station or dock to provide an authentication routine that is able to identify specific hardware, firmware, or software on the device in order to facilitate device maintenance or product updates. A more detailed description of an example wireless charging station is provided below with respect to FIGS. 18-19.

The device 100 may include a variety of other components, including for example, a camera or camera modules. The camera may be configured to capture an image of a scene or subject located within a field of view of the camera. The image may be stored in a digital file in accordance with any one of a number of digital formats. In some embodiments, the device 100 includes a camera, which includes an image sensor formed from a charge-coupled device (CCD) and/or a complementary metal-oxide-semiconductor (CMOS) device. The camera may also include one or more optical components disposed relative to the image sensor, including, for example, a lens, an filter, a shutter, and so on.

Figure 3:
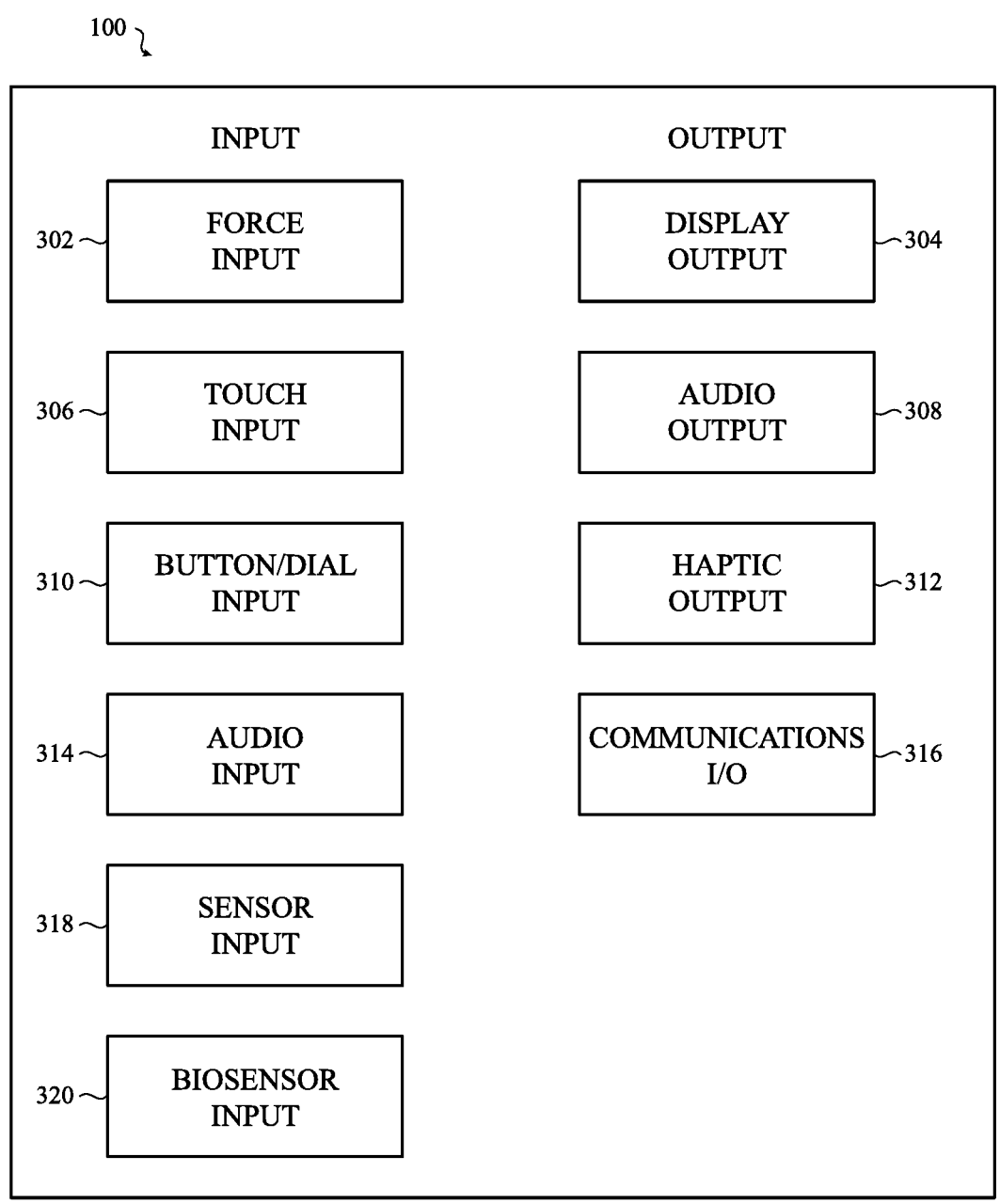
FIG. 3 depicts an example functional diagram for a wearable electronic device.

FIG. 3 depicts functional elements of the device 100, in accordance with some embodiments. In particular, FIG. 3 depicts the inputs that may be received and outputs that may be produced on an example device 100. By way of example, the device 100 may correspond to the devices shown in FIGS. 1 and 2. As shown in FIG. 3, the device 100 may include a force input 302 that may be produced using a force sensor that is configured to detect and measure the magnitude of a force of a touch on a surface of the device. The force input 302 may include a non-binary output that is generated in response to a touch. For example, the force input 302 may include a range of values or analog value that corresponds to the amount of force exerted on a surface of the device. Additionally or alternatively, the force input 302 may include binary (e.g., on, off) output in response to the force of a touch. The force input 302 may be used to control various aspects of the device. For example, the force input 302 may be used to control an aspect, such as a cursor or item selection on a user interface presented on the display of the device. The force input 302 may also be used to control the audio output 308, haptic output 312, and other functionality of the device. The force input 302 may also be used to distinguish between different types of input from the user. For example, a light touch from the user may be interpreted as a scroll command and used to index or scroll through a list of items on the display. A harder touch from the user may be interpreted as a selection or confirmation of an item on the display. In some embodiments, the force input 302 is used to distinguish an intentional touch from the user from an incidental or accidental touch that may be ignored.

As shown in FIG. 3, the device 100 may also include a touch input 306 that may be produced using a touch sensor that is configured to detect and measure the location of a touch on a surface of the device. In some implementations, the touch sensor is a capacitive-based touch sensor that is disposed relative to the display or display stack of the device. The touch sensor may be a separate non-integrated sensor relative to the force sensor. In alternative embodiments, the touch sensor may also be physically and/or logically integrated with the force sensor to produce a combined output. The touch input 306 may be used to control various aspects of the device. For example, the touch input 306 may be used to control an aspect of the user interface presented on the display of the device. The touch input 306 may also be used to control the audio output 308, haptic output 312, and other functionality of the device.

In some cases, the logical integration of the force input 302 and the touch input 306 enhances the versatility or adaptability of device 100 by enabling a more sophisticated user interface than is currently available on some traditional wearable devices. In particular, the force input 302 and the touch input 306 may be combined to interpret a wider range of gestures and input commands than may be possible using, for example, only a touch input. For example, the force input 302 may provide a magnitude of a force of a touch, which may be used to distinguish between two touch input commands that have a similar location or gesture path. An improved touch interface using both force input 302 and touch input 306 may be particularly advantageous when interpreting touch commands on a relatively small area surface, such as a display screen or cover glass of a wearable electronic device.

As shown in FIG. 3, the device 100 may also include a button/dial input 310 that may be produced using an input device that is configured to receive input from the user. As described previously, the device 100 may include one or more buttons disposed on or near an external surface of the housing and are configured to receive input from a user. The device may also include a dial or crown that is configured to accept rotational input from the user. As described in more detail below with respect to FIGS. 24A-B, the dial or crown may also include a push feature that is adapted to accept input from the user.

The device 100 may also accept audio input 314 using a microphone or other acoustic sensing device. The audio input 314 may be adapted to accept input from the user, including voice commands and other audio signal input. The audio input 314 may also be adapted to detect and measure ambient audio conditions that may be used to adjust the volume of the audio output 308 or operation of the haptic output 312. The audio input 314 may also be used to record an audio stream or voice message in accordance with an audio recording application or software program.

As shown in FIG. 3, the device 100 may include a display output 304 in accordance with some embodiments. The display output 304 includes visual or graphical output that may be produced using the display element of the device. In some embodiments, the display output 304 includes a graphical user interface produced using an operating system or software application executed on one or more processing units of the device. In one example, the display output 304 includes a graphical depiction that resembles a watch face or other timekeeping device. In other examples, the display output 304 includes a graphical interface for an e-mail, text messaging, or other communication-oriented program. The display output 304 may also present visual information that corresponds to one of the other functional aspects of the device 100. For example, the display output 304 may include information that corresponds to the biosensor input 320, sensor input 318, force input 302, touch input 306, and others.

As shown in FIG. 3 the device 100 may include an audio output 308 that may be produced with a speaker or acoustic module. The audio output 308 may include sounds or audio signals that are associated with the operation of the device. For example, the audio output 308 may correspond to the operation of an input device to provide audio feedback to the user. For example the audio output 308 may correspond to an input received in the form of a force input 302, touch input 306, and/or button/dial input 310. In some cases, the audio output 308 may also include a portion of an auditory alert that may be produced alone or combined with a haptic output 312 and/or display output 304 of the device 100.

The device 100 may also include a sensor input 318 produced using one or more sensors that may be configured to monitor and detect various environmental conditions. For example, the sensor input 318 may include signals or data produced using an ambient light sensor, proximity sensor, temperature sensor, barometric pressure sensor, or other sensor for monitoring environmental conditions surrounding or near the device. In general, the sensor input 318 may be used to adapt the functionality of the device 100 to conform to the one or more environmental conditions. For example, the brightness of the display output 304, the volume of the audio output 308, and/or the operation of the input to the device 100 may be based on the sensor input 318.

In some embodiments, the sensor input 318 includes input produced by one or more motion sensors. The motion sensors may include one or more of the following: an accelerometer, a gyroscope, a tilt sensor, or other type of inertial measurement device. A sensor input 318 produced using one or more motion sensors may be used to monitor and detect changes in motion of the device 100. Changes in linear and angular motion may be used to determine or estimate an orientation of the device relative to a known location or fixed datum. The sensor input 318 produced from the one or more motion sensors may also be used to track the movement of the user. The movement of the user may be used to facilitate navigation or map-guided functionality of the device. Additionally, input related to the gross movement of the user can be used as a pedometer or activity meter, which may be stored and tracked over time to determine health metrics or other health-related information. Additionally, in some embodiments, sensor input 318 from the one or more motion sensors may be used to identify motion gestures. For example, the motion sensors can be used to detect an arm raise or the position of a user's body (within a predetermined confidence level of certainty).

The device 100 may also include a biosensor input 320 produced using one or more biosensors or biosensor modules that are configured to monitor physiological and/or health conditions of a user. As discussed above with respect to FIG. 2, the device may include one or more optical sensors for measuring heart rate, blood pressure, oxygen saturation, or a combination thereof. The device may also include one or more sensors having electrical contacts that are disposed to contact the user's body. The sensors may be configured to measure electrocardiographic (ECG) characteristics, galvanic skin resistance, and other electrical properties of the user's body. Additionally or alternatively, sensors may be configured to measure body temperature, exposure to UV radiation, and other health related information. The biosensor input 320 may be combined with other aspects of the device to provide heath-monitoring functionality. For example, the biosensor input 320 may be used to compute data that is presented using the display output 304. The operation of the biosensor input 320 may also be controlled using the force input 302, touch input 306, or other user input 310 to provide an interactive health monitoring function or application.

As shown in FIG. 3, the device may include a haptic output 312 that may be produced using one or more haptic devices that are configured to provide haptic feedback to the user. In particular, the haptic output 312 may be produced using one or more electromechanical subassemblies that are configured to induce motion or vibration in the device, which may be perceived or sensed by the user. In some cases, the haptic actuator or device is tuned to operate based on a resonance or near resonance with respect to the device, which may enhance haptic output. In some cases, the haptic actuator or device is configured to operate based on a resonance or near resonance with respect to some components of the device, such as the band or clasp of the device.

In some embodiments, the haptic output 312 may correspond to the operation of one or more other modules or subsystems. For example, the haptic output 312 may include a vibration or haptic feedback that corresponds to an audio alert or visual alert or signal produced by the acoustic module or display, respectively. Additionally or alternatively, the haptic output 312 may be operated in conjunction with an input from the user. The haptic output 312 may include haptic or force feedback that confirms that the user input was or is being received. By way of example, a haptic output 312 may include a click or vibration when the crown of the device is turned or a button is depressed. The haptic output 312 may also be coordinated with other functionality of the device including, for example, message transmission operations, power management operations, force sensor operations, biosensor operations, to provide a notification, to provide an alert, and others.

As shown in FIG. 3, the device 100 may also include communications input/output (I/O) 316, which may facilitate communication with an external device or system. The communications I/O 316 may be produced using one or more wireless interfaces, including radio frequency cellular interfaces, fiber optic interfaces, acoustic interfaces, Bluetooth interfaces, Near Field Communication interfaces, infrared interfaces, USB interfaces, Wi-Fi interfaces, TCP/IP interfaces, network communications interfaces, or any conventional communication interfaces. In some cases, the communications I/O 316 may include signals and data received from an external device that has been paired or is otherwise in electronic communication with the device 100. The external data included in the communications I/O 316 may include, for example, message data associated with an electronic communication, notification data associated with an event, and/or data related to audio or visual content. The communications I/O 316 may also include an authorization or identification of external devices in communication with the device 100 or users associated with one or more external devices. Similarly, the communications I/O 316 may be used to output various forms of data or signals to one or more devices or systems that are external to the device 100. For example, the communications I/O 316 may include data or computations that are produced using the biosensor input 320 and/or the sensor input 318.

Figure 4:
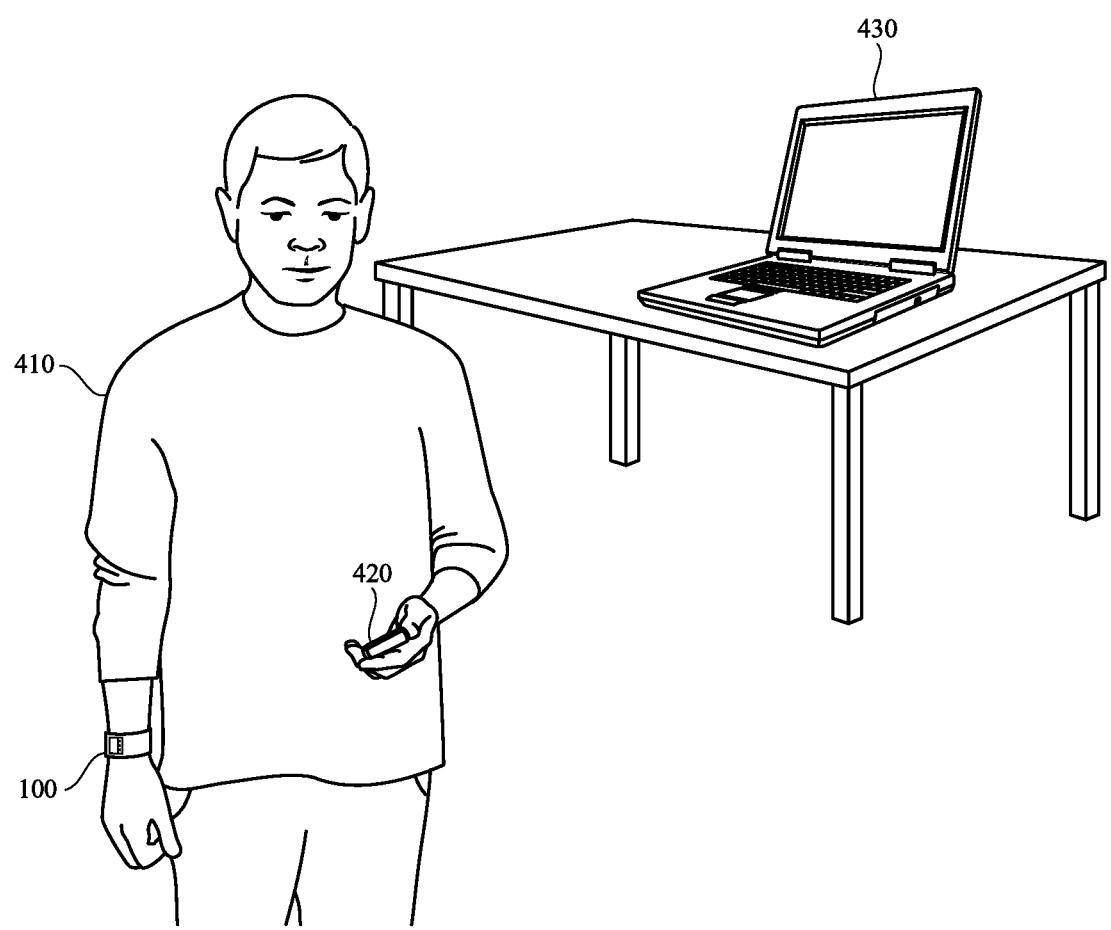
FIG. 4 depicts an example wearable electronic device as part of a system of devices.

FIG. 4 depicts an example wearable electronic device 100 as part of a system of devices. By way of example, the wearable electronic device 100 of FIG. 4 may correspond to the devices shown in any of the previous figures. Generally, the wearable electronic device 100 may communicate wirelessly with any of a number of other devices, such as mobile phone 420, computer 430, tablet computing devices, personal media players, televisions, networked home appliances, networked home controls, electronic systems in vehicles, and so on. Additionally, the wearable electronic device 100 may communicate wirelessly with any of a number of electronic accessories, including headset devices, portable speaker devices, portable microphone devices, display screens, and so on. Communication may be through a wired or wireless connection, including any technology mentioned herein.

In some embodiments the wearable electronic device 100 may accept a variety of bands, straps, or other retention mechanisms (collectively, "bands"). These bands may be removably connected to the electronic device by a feature formed into the band or band assembly that is accepted in a recess or other aperture within the device and locks thereto. An example band interface is described in more detail below with respect to FIGS. 25A-C.

In general, a user may change combinations of bands and electronic devices, thereby permitting mixing and matching of the two categories. It should be appreciated that devices having other forms and/or functions may include similar recesses and may releasably mate with a lug and/or band incorporating a lug. In this fashion, a system of bands and devices may be envisioned, each of which is compatible with another. A single band may be used to connect to devices, as one further example; in such embodiments the band may include electrical interconnections that permit the two devices to transmit signals to one another and thereby interact with one another.

Insofar as the electronic device 100 may connect either physically or through a data communication link with other computing devices, the combination of devices and bands may be thought of as an ecosystem having multiple parts that interact with one another, may intelligently communicate with one another, may share functionality and/or may substitute for one another in terms of operations, output, input and the like. Examples of devices existing in such an ecosystem follow, but are illustrative rather that limiting.

As one example, a number of electronic devices 100, 420, 430 may each have identical or similar attachment structures that permit them to share a band or connector. A user may thus change the interconnected band and device(s) with respect to one another, permitting a number of different physical connections between different ecosystem components. In some embodiments, a band that serves to retain an electronic device only may be swapped for bands having additional functionalities, such as transmitting data between devices connected to the band, adding functionality to a connected device that the device lacks, providing additional power to a connected device, and so on. Further, different bands may look different, so that the appearance of the electronic device(s) in combination with a band(s) may change by changing the band(s) and/or device(s) with respect to one another.

As another example, electronic devices 100, 420, 430 may communicate with one another as part of the overall ecosystem. Data may be passed from one device 420 to another 100. This may be useful if the user 410 is wearing one electronic device 100 but is not near another device 430 that wishes to notify the user or interact with the user in some fashion. Continuing the example, the computer 430 may transmit a reminder or message to the wearable device 100 to gain the user's attention. As another example, the computer 430 (or any other electronic device in the ecosystem) may transmit a state of an application or even the device itself to the wearable device 100. Thus, for example, if an application operating on the computer needs the user's attention, it may be gained through an alert issued by the wearable device.

Data communication between devices in an ecosystem may also permit the devices to share functionality. As one non-limiting example, electronic devices may share sensor data with one another to permit one device access to data it normally would not have, from a sensor it does not physically incorporate. Thus, any given device 100, 420, 430 may draw on the abilities of other devices in the ecosystem to provide an enhanced and relatively seamless experience for a user 410.

Figure 5:
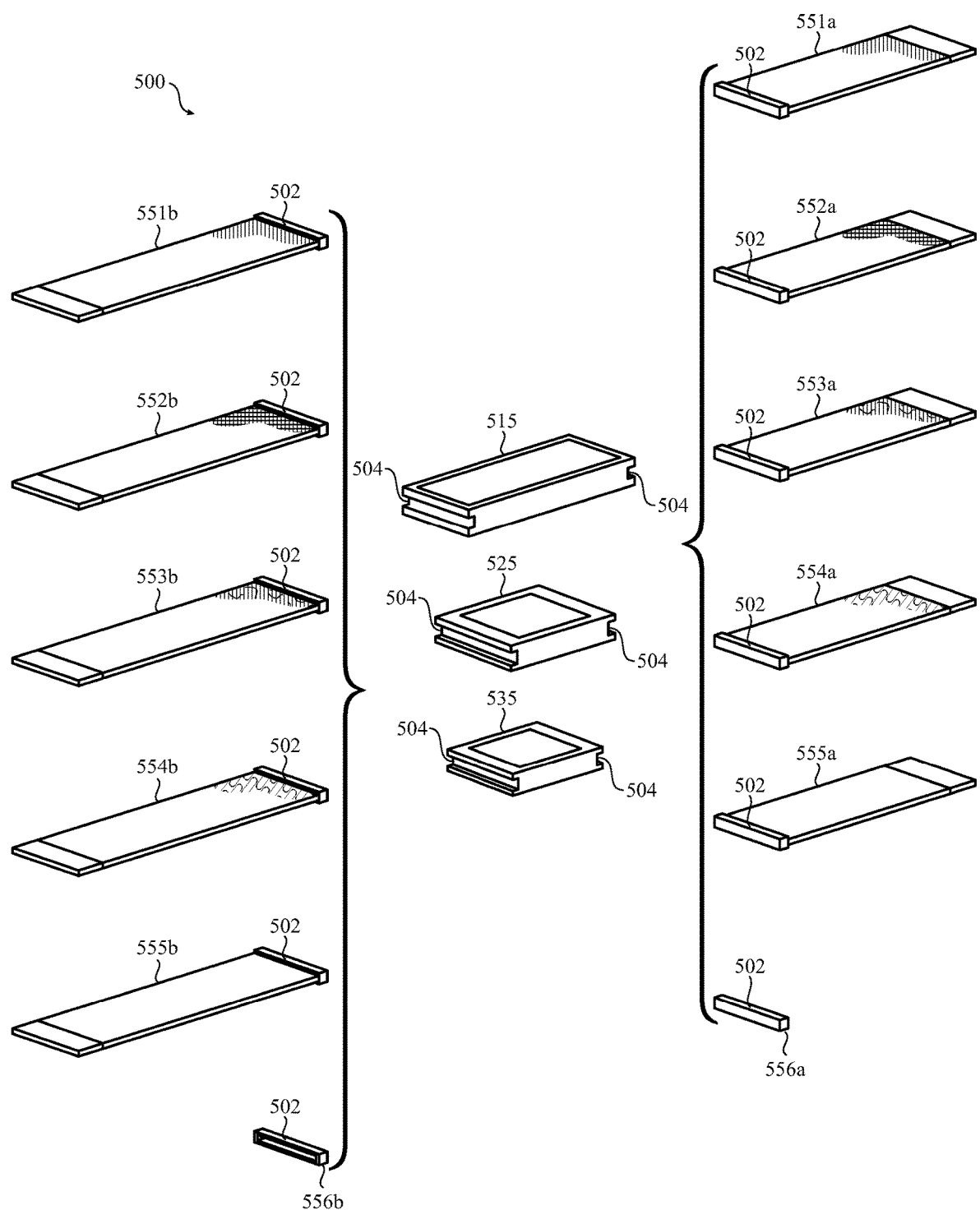
FIG. 5 depicts a system of interchangeable components for a wearable device.

FIG. 5 depicts a system 500 of interchangeable components for a wearable device. By way of example, one or more of the devices of FIG. 5 may correspond to the devices shown in any of the previous figures. FIG. 5 depicts a system 500 including a variety of interchangeable components, including multiple device bodies 515, 525, 535 that are configured to connect via a standard interface to any one of a number of different bands 551a-b, 552a-b, 553a-b, 554a-b, and 555a-b. In addition, each of the three devices may be configured to connect via a standard interface to another type of non-band component, such as a lug 556a-b, non-band component, or other device.

As shown in FIG. 5, the system 500 may include a body or device that is adapted to attach to one or more bands, straps, or other similar component that may be used to attach the device to the body of a user. In some embodiments, the device may be interchangeable or interchanged to provide a different set of functions or features. In some embodiments, the bands or attachment components may be interchangeable or interchanged to provide desired functionality or features.

In the example depicted in FIG. 5, each of the devices includes at least one receiving feature 504 that is configured to interconnect with a corresponding feature 502 that is attached to or integrally formed with the end of each of the bands or other mating parts. In some embodiments, receiving feature 504 includes a channel or groove that is formed in one end of the device body. The mating feature 502 of a respective band or component may be configured to slidably engage with the receiving feature 504 of a respective device body to attach the band or component. An example receiving feature is described in more detail below with respect to FIGS. 25A-C. In some embodiments, the receiving feature 504 and the mating feature 502 are standardized in the system 500 and, thus, any of the bands (551a-b, 552a-b, 553a-b, 554a-b, and 555a-b) can be interchangeably used with any of the device bodies 515, 525, 535.

With respect to FIG. 5, each of the bands may be formed from a different material or using a different construction. In the present example, bands 551a-b may be formed from a textile material that may be constructed from a pattern of thread or fiber material. The textile material may include a variety of materials, including natural fibers, synthetic fibers, metallic fibers, and so on. The bands 552a-b may be formed from a woven material and may be constructed from an array of warp fibers or threads interwoven with one or more weft fibers or threads. Similarly, the warp and weft fibers may include a variety of materials, including natural fibers, synthetic fibers, metallic fibers, and so on. The bands 553a-b may be formed from leather material 553a-b. In one example, the bands 553a-b are formed from a sheet or strip of cowhide; however, the bands 553a-b may also be formed from one of any number of types of animal hide. The leather material 553a-b may also include a synthetic leather material, such as vinyl or plastic. The bands 554a-b may be formed from a metallic mesh or link construction. For example the bands 554a-b may be formed from a Milanese mesh or other similar type of construction. The bands 555a-b may be formed from a silicone or other elastomer material.

In some cases, the band is a composite construction including various materials, which may be selected based on the end use or application. In some embodiments, a first band strap, or a first portion of the first band strap, may be made up of a first material and a second band strap, or a second portion of the second band strap, may be made from a second, different material. The band may also be made up of a plurality of links and, as such, the band may be resizable by, for example, adding or removing links. Example bands and band constructions are provided below in Section 12.

In the system 500, an interchangeable band may allow for individual customization of the device or to better adapt the device for a range of uses or applications. In some instances, the type of band that is selected and installed can facilitate a particular user activity. For example, band 551a-b may be formed from a textile material and include a durable clasp that may be particularly well suited for exercise or outdoor activities. Alternatively, as discussed above the band 554a-b may be formed from a metallic material and include a thin or low-profile clasp that may be well suited for more formal or fashion-focused activities.

In some embodiments, the band may be coupled to a separate component having the mating feature 502. The band may be coupled using pins, holes, adhesives, screws, and so on. In yet other embodiments, the band may be co-molded or overmolded with at least a portion of the component having the mating feature 502. In some embodiments, the band is coupled to the component via a pin that allows the straps to rotate with respect to the component. The pin may be formed integrally with or disposed in a loop formed in the end of the band.

In the example system 500, each of the bands is shown as having a generic band clasp. However, the type of band clasp that is used may vary between embodiments. On example band clasp may include a first band strap having a buckle or tang assembly which is configured to interface with a second band strap having a series of apertures or holes formed with the strap. Additionally or alternatively, the bands may include a magnetic clasp having one or more magnetic elements on a first band strap that is configured to mate to one or more magnetic or ferromagnetic elements on a second band strap.

As shown in FIG. 5, the system may include multiple device bodies 515, 525, 535 that may vary in size, shape, and composition. The device body 515, 525, 535 may include one or more of the embodiments described herein and may include, but is not limited to a wearable computer, a wearable watch, a wearable communication device, a wearable media player, a wearable health monitoring device, and/or the like. In particular, the device body may correspond to the device body described with respect to device body 610 of device 100 (shown in FIG. 6).

1. Example Wearable Electronic Device

Figure 6:
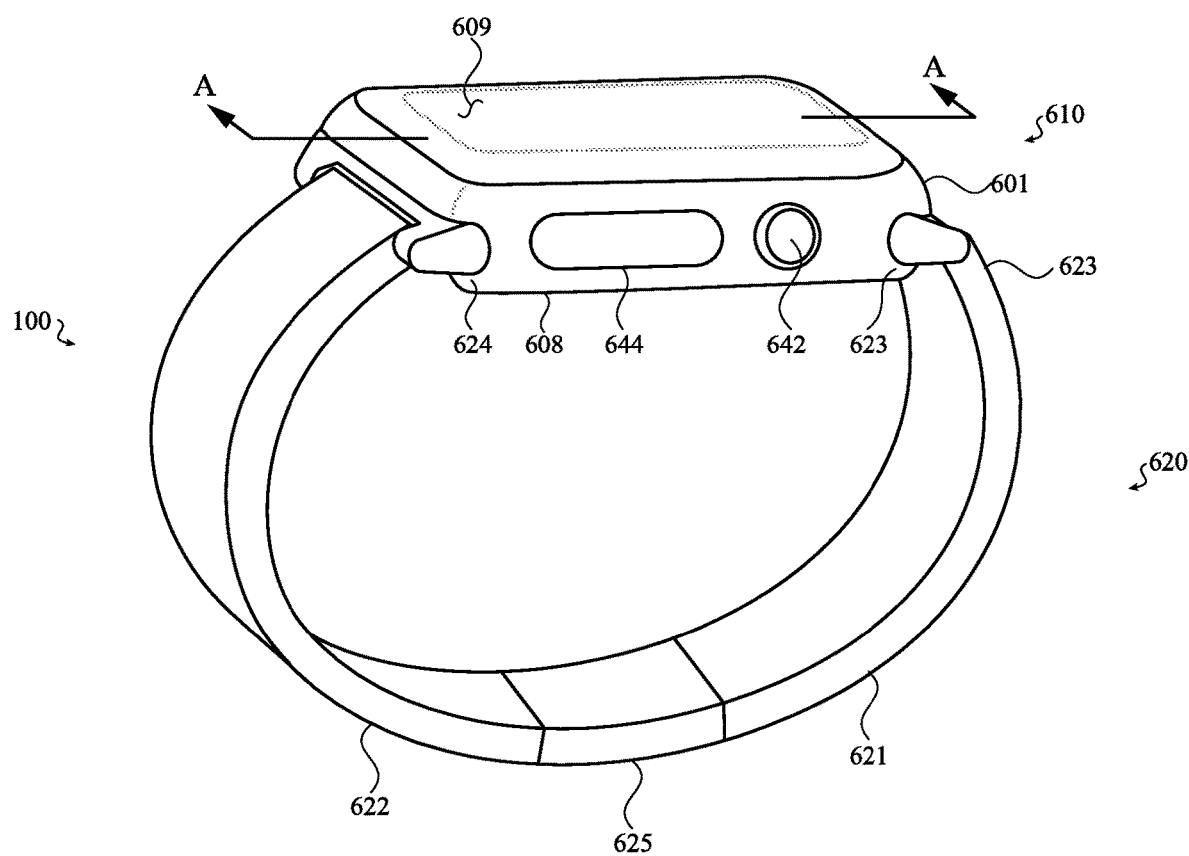
FIG. 6 depicts an example wearable electronic device having a device body and band.

FIG. 6 depicts an example wearable electronic device, which may include various aspects of the device(s) described above. In some embodiments, multiple modules or subsystems are physically and operationally integrated together to provide particular functionality or device features. In particular, the interaction between the subsystems, or the subsystems themselves, may be configurable by the user, manufacturer, or vendor to adapt the device to produce certain functionality. Some example combinations and interactions between the various modules and subsystems are expressly provided in the present description. However, the combinations and interactions provided herein are merely illustrative in nature and are not intended to be limiting on the scope of the disclosure.

FIG. 6 depicts an example configuration of a wearable electronic device 100. In particular, FIG. 6 depicts an electronic wearable device 100 including a device body 610 that may be configured to be attached to the wrist of a user using a band assembly 620. This configuration may also be referred to herein as a wearable device, a device, an electronic wristwatch, or an electronic watch. While these terms may be used with respect to certain embodiments, the functionality provided by the example electronic wearable device 100 may be substantially greater than or vary with respect to many traditional electronic watches or timekeeping devices.

In the present example, the exterior surface of the device body 610 is defined, in part, by the exterior surface of the housing 601 and the exterior surface of the cover 609. In the example depicted in FIG. 6, the device body 610 is substantially rectangular with round or curved side portions. The outer surfaces of the cover 609 and the housing 601 coincide at a joint interface and cooperate to form a continuous contoured surface. The continuous contoured surface may have a constant radius and may be tangent to a flat middle portion of the cover 609 and/or a flat bottom portion of the housing 601. In some embodiments, the cover 609 has substantially the same shape as a flat bottom portion and at least a portion of the curved side portions of the housing 601. A more complete description of the geometry of the cover 609 and the housing 601 is provided below with respect to FIGS. 7 and 8.

In the example of FIG. 6, the device 100 includes a display (item 120 of FIG. 2) that is disposed at least partially within an opening or cavity defined within a top portion of the housing 601 of the device body 610. The display may be formed from a liquid crystal display (LCD), organic light emitting diode (OLED) display, organic electroluminescence (OEL) display, or other type of display device. The display may be used to present visual information to the user and may be operated in accordance with one or more display modes or the software applications being executed on the device 100. By way of example, the display may be configured to present the current time and date similar to a traditional watch or timepiece. The display may also present a variety of other visual information that may correspond to or be produced using one of the other modules in the device 100. For example, the display may be configured to display one of a variety of notification messages, which may be generated based on data received from the one or more sensors, the wireless communication system, or other subsystem of the device 100. The display may also be configured to present visual information or data that is based on the output of one or more sensor outputs. The display may also provide status or information related to a wireless charging process or battery power. The display may also present visual output or information related to media being produced using a speaker or acoustic module of the device 100. Accordingly, a variety of other types of visual output or information may be presented using the display.

Figure 21A:
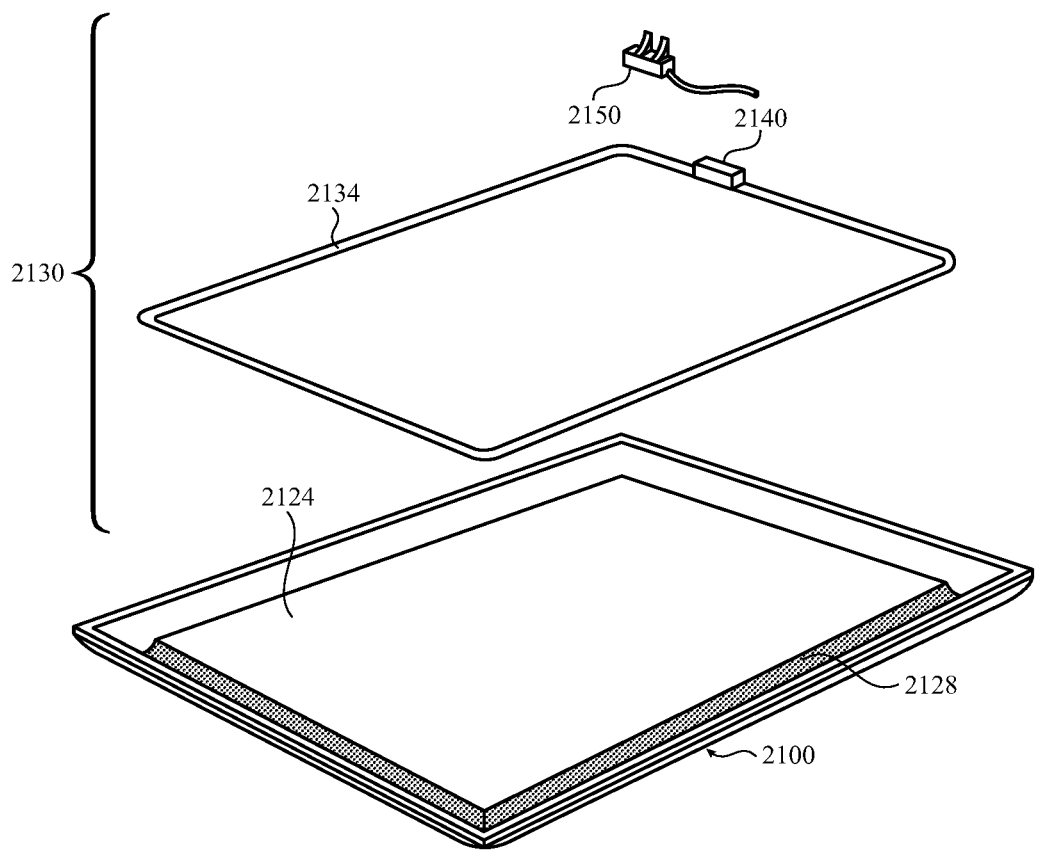
FIGS. 21A-B depict an example cover and antenna.
Figure 21B:
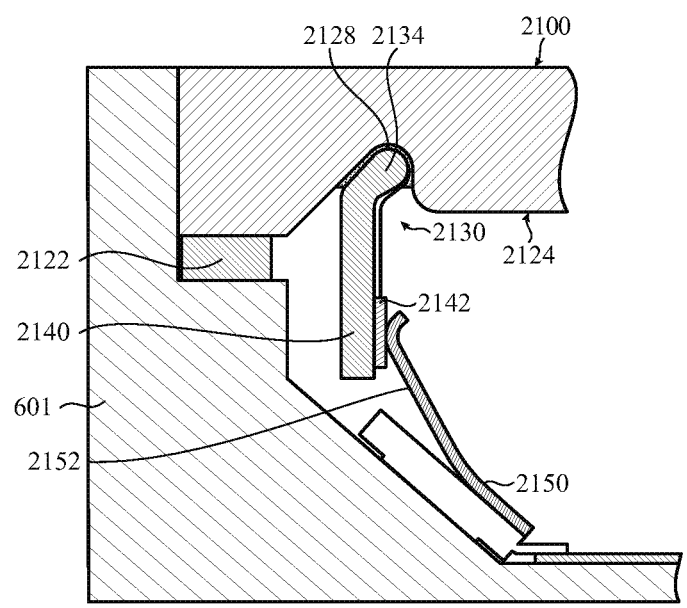

In the current example, the display includes or is integrated with a cover 609 that helps to protect the display from physical impact or scratches. In the field of wearable devices, the cover 609 may also be referred to generically as a crystal or cover glass, regardless of the material that is used to form the cover 609. In some cases, the cover 609 is formed from a sheet or block of sapphire material. Sapphire may provide superior optical and surface hardness properties as compared to other materials. In some cases, the sapphire material has a hardness of approximately 9 on the Mohs scale. In alternative embodiments, the cover 609 is formed from a glass, polycarbonate, or other optically transparent material. The cover 609 may also be coated with one or more optical or mechanical enhancing materials or surface treatments. For example, interior and/or exterior surfaces of the cover 609 may be coated with an anti-reflective (AR), oleophobic or other coating to enhance the visible or functional properties of the display. Additionally, in some cases, the cover 609 may be configured to cooperate with an antenna used to facilitate wireless communication with an external device. FIGS. 21A-B, described in more detail below, provide one example embodiment of a cover configured to cooperate with an antenna.

In the example depicted in FIG. 6, the cover 609 is formed from a transparent material and, when assembled has an external surface and an internal surface. The cover 609 is disposed above the display and encloses a cavity or opening formed in the top portion of the housing 601. In some embodiments, the external surface of the cover 609 cooperates with the external surface of the housing to form a substantially continuous external peripheral surface of the electronic device. As shown in FIG. 6, the external surface of the cover 609 has a flat middle portion at the center of the cover, which extends outwardly. The cover 609 also includes a curved edge portion that emanates from and surrounds the flat middle portion and extends outwardly to an edge at the side of the cover 609. In some embodiments, the cover 609 also includes an opaque mask disposed relative to the internal surface of the transparent cover. The opaque mask may correspond to or otherwise define the viewable area of the display 120. The mask may have an outer boundary that is located proximate the edge of the side of the cover 609 and has an inner boundary located within the curved edge portion of the cover 609.

As shown in FIG. 6, the cover 609 is disposed relative to a top portion of the housing 601. The housing 601 includes a top portion defining an opening, which is surrounded by a curved side portion. In the present example, the curved edge portion of the cover 609 coincides with the curved side portion of the housing 601 to form a continuous external surface of the electronic device 100. In some instances, the cover 609 may have a contour that follows or otherwise corresponds to a similar contour of the housing 601 to form a substantially continuous surface at the interface between the two components. As shown in FIG. 6, the cover 609 protrudes above the housing 601.

Figure 7:
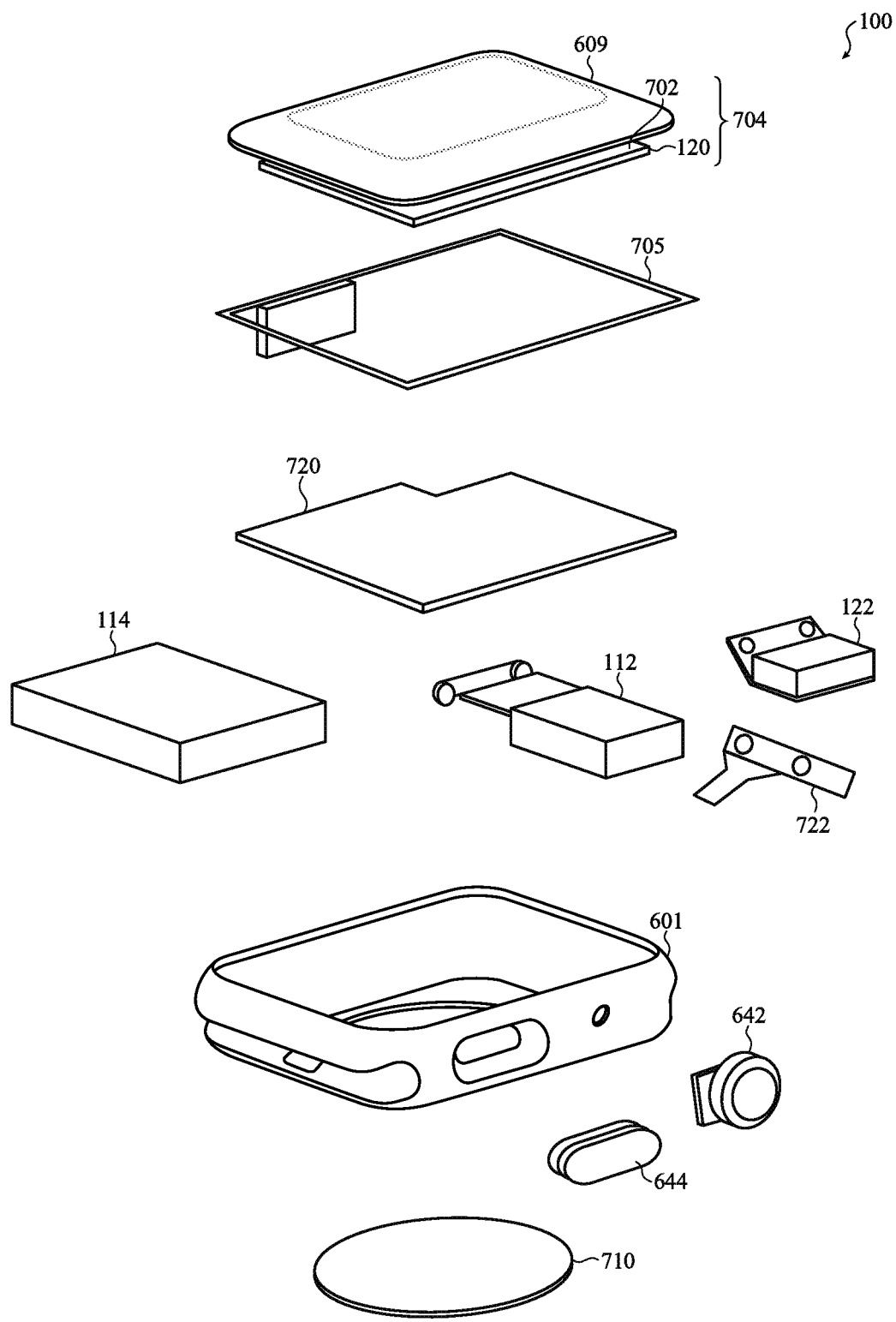
FIG. 7 depicts an exploded view of components of an example wearable electronic device.

In some instances, the cover 609 is disposed relative to a touch sensor (item 702 of FIG. 7). In some embodiments, the touch sensor may be integrated with the display or other element of the device 100. The touch sensor may be formed from one or more capacitive sensor electrodes or nodes that are configured to detect the presence and/or location of an object or the user's finger that is touching or nearly touching the surface of the display. In some cases, the touch sensor includes an array of sensing nodes formed in accordance with a mutual capacitance sensing scheme.

In one example, the touch sensor may include an array of mutual capacitance touch nodes that can be formed by a two-layer electrode structure separated by a dielectric material. One layer of electrodes may comprise a plurality of drive lines and another layer of electrodes may comprise a plurality of sense lines, and where the drive lines and the sense lines cross, mutual capacitive sense nodes are formed (also referred to as coupling capacitance). In some implementations, the drive lines and sense lines may cross over each other in different planes separated from one another by a dielectric. Alternatively, in other embodiments the drive lines and sense lines can be formed substantially on a single layer. An example touch sensor and touch-sensing node are described in more detail below with respect to FIGS. 14A-C and 15A-B.

Alternatively or additionally, the touch sensor may include one or more self-capacitive nodes or electrodes that are configured to detect a discharge of electrical current or charge when an object, such as a user's finger, contacts or nearly contacts a surface of the housing 601 or other surface of the device 100. Other types of electronically sensing nodes, including resistive, inductive, or the like, may also be integrated into a surface of the device 100.

In some embodiments, the device 100 may also include a force sensor (item 705 of FIG. 7). The force sensor may be disposed relative to the display 120 or integrated with other elements of the device 100. In some cases, the force sensor includes one or more force sensing structures or force-sensing nodes for detecting and measuring the magnitude of a force or pressure due to a touch on a surface of the device 100. The force sensor may be formed from or implement one or more types of sensor configurations. For example, capacitive and/or strain based sensor configurations may be used alone or in combination to detect and measure the magnitude of a force or pressure due to a touch. As described in more detail below, a capacitive force sensor may be configured to detect the magnitude of a touch based on the displacement of a surface or element on the device. Additionally or alternatively, a strain-based force sensor may be configured to detect the magnitude of a touch based on the deflection. Example force sensor and force-sensing modules are described in more detail below with respect to FIGS. 9-12.

As shown in FIG. 6, the device 100 also includes device body 610 including a housing 601 that upon which may be mounted or integrated with various components of the device 100. The housing 601 serves to surround at a peripheral region as well as support the internal components of the product in their assembled position. In some embodiments, the housing 601 may enclose and support internally various components (including for example integrated circuit chips and other circuitry) to provide computing and functional operations for the device 100. The housing 601 may also help define the shape or form of the device. That is, the contour of the housing 601 may embody the outward physical appearance of the device. As such, it may include various ornamental and mechanical features that improve the aesthetical appearance and tactile feel of the device. For example, the housing 601 may include a contoured surface that includes rectilinear contours, curvilinear contours, or combinations thereof. The housing 601 may also include various surface features, including textures, patterns, decorative elements, and so on.

In the present example, the housing 601 is formed from a single piece, which may also be referred to as single-body, unitary, or uni-body design or construction. By utilizing a single-body construction, the structural integrity of the device may be improved as compared to a multi-piece construction. For example, a single body may be more easily sealed from contaminants as compared to a multi-piece enclosure. Additionally, a single-body enclosure may be more rigid due, in part, to the absence of joints or seams. The rigidity of the housing 601 may be further enhanced by increasing the material thickness in areas where mechanical stress may be greatest, while also maintaining or thinning other areas where mechanical stress may be lower or reduced. Variations in the thickness of the housing 601 may be possible by machining or casting the housing 601 as a single piece. Additionally, a single-body housing 601 may include one or more features for mounting or integrating the internal components of the device 100, which may facilitate manufacturing and/or assembly of the device 100.

An example housing 601 is described in more detail below with respect to FIG. 8. The housing 601 may be formed from a variety of materials, including, without limitation plastic, glass, ceramics, fiber composites, metal (e.g., stainless steel, aluminum, magnesium), other suitable materials, or a combination of these materials. Further, the housing 601 may include a surface treatment or coating, which may be formed from a variety of materials, including, without limitation aluminum, steel, gold, silver and other metals, metal alloys, ceramics, wood, plastics, glasses, and the like.

As discussed above, the display, the touch sensor, and force sensor may be disposed within the housing 601. In this example, one or more buttons 644 and a crown 642 used to receive user input may also be disposed within or relative to the housing 601. Other types of user input, including for example, one or more dials, slides, or similar user input devices or mechanisms may also be disposed within or relative to the housing 601. As described in more detail with respect to FIGS. 7 and 8, the housing 601 may include various features for attaching and mounting the subassemblies and modules of the device 100. In particular, the housing 601 may have one or more openings for receiving the cover 609, the display, the force sensor, or other components. The housing 601 may also include one or more holes or openings for receiving the button 644 and crown 642 that are located around the perimeter of the device 100. In some embodiments, the housing 601 also includes internal features, such as bosses and threaded portions, that can be used to attach modules or components within the housing 601.

The device 100 may also include an ambient light sensor (ALS) that is configured to detect and measure changes in ambient lighting conditions. The ALS may include a photodiode and one or more optical elements or lenses for collecting light. An ALS may be located on an external facing surface that is less likely to be blocked when the device is worn or in use. The ALS may be used to adjust settings, including screen brightness and other visual output depending on the overall lighting conditions.

The housing 601 may also include one or more motion-sensing elements or devices for detecting motion of the device 100. For example, the device 100 may include one or more accelerometers that are configured to sense acceleration or changes in motion. Additionally or alternatively, the device 100 may include one or more gyroscopic sensors that are configured to detect changes in direction. In some cases, the one or more gyroscopic sensors may include a spinning mass that can be used to detect changes in angular velocity. Multiple motion-sensing elements may be used to detect motion along multiple directions or axes. The motion sensors may also be used to identify motion gestures. For example, the motion sensors can be used to detect an arm raise or the position of a user's body (within a predetermined confidence level of certainty). The one or more motion-sensing elements may be used to determine an orientation of the device relative to a known or fixed datum. For example, the device may include a compass and/or global positioning system (GPS) that can be used to identify an absolute position. The one or more motion sensing elements may then measure deviation or movement with respect to the absolute position to track movement of the device or the user wearing the device. In some implementations, the one or more motion-sensing elements are used to detect gross movement of the device or user. The gross movement may be used as a pedometer or activity meter, which may be tracked over time and used to calculate a health metric or other health-related information.

Figure 8:
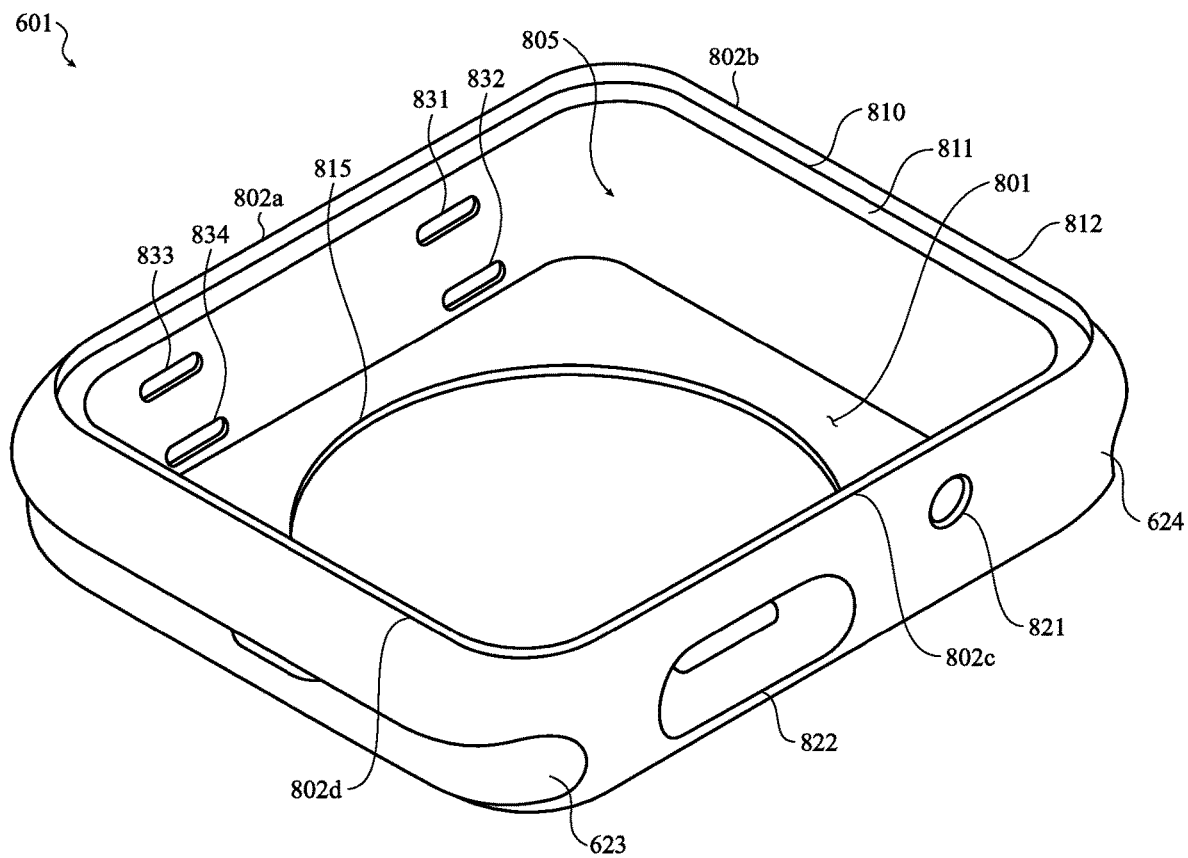
FIG. 8 depicts an example housing for a wearable electronic device.

Described in more detail with respect to FIG. 8, the housing 601 may also include one or more openings or orifices coupled to an acoustic module or speaker 122, which may include a speaker and/or a microphone subassembly. Although the housing 601 may include one or more openings or orifices, the housing 601 may still be substantially waterproof/water resistant and may be substantially impermeable to liquids. For example, the opening or orifice in the housing or enclosure may include a membrane or mesh that is substantially impermeable to liquid ingress. Additionally or alternatively, the geometry of the opening or orifice and other internal features of the housing 601 may be configured to reduce or impede the ingress of liquid or moisture into the device 100. In one example, the opening is formed from one or more orifices that are offset with respect to an internal acoustic chamber or cavity, which may prevent a direct path from the outside of the housing 601 into the acoustic module.

As shown in FIG. 6, the device 100 includes a device body 610 that may be attached to a user's wrist using a band 620. In the present example, the band 620 include a first band strap 621 attached to a first receiving feature 623 and a second band strap 622 attached to a second receiving feature 624. In some embodiments, the first and second band straps 621, 622 include a lug feature that is configured to attach to the first and second receiving features 623, 624, respectively. As shown in FIG. 6, the free ends of the band straps 621, 622 are connected with a clasp 625.

The band straps 621, 622 are formed from a flexible or compliant material that may be specially configured for a particular application. The band straps 621, 622 may be formed from a variety of materials, including, for example, leather, woven textiles, or metallic mesh materials. The material and construction of the band straps 621, 622 may depend on the application. For example, the band straps 621, 622 may be formed from a woven textile material configured for exposure to impact and moisture typically associated with outdoor activities. In another example, the band straps 621, 622 may be formed from a metallic mesh material that may be configured to have a fine finish and construction that may be more appropriate for professional or social activities.

Similarly, the clasp 625 of the band 620 may be configured for a particular application or to work with a particular style of band. For example, if the band straps 621, 622 are formed from a metallic mesh material, the clasp 625 may include a magnetic clasp mechanism. In the present example, the device 100 is configured to be attached to the wrist of a user. However, in alternative embodiments, the device may be configured to be attached to the arm, leg or other body part of the user.

The housing 601 includes one or more features for attaching the band straps 621, 622. In the present example, the housing 601 includes a first receiving feature 623 and a second receiving feature 624 for attaching the first band strap 621 and the second band strap 622, respectively. In this example, the band straps 621, 622 include a lug portion that is adapted to mechanically engage with the receiving features 623, 624. A more detailed description of the receiving features and lugs is provided below with respect to FIGS. 25A-C. As shown in FIG. 6, the first 623 and second receiving features 624 may be integrally formed into the housing 601. In alternative embodiments, the receiving features may be formed from separate parts and may be attached to the housing 601 during manufacturing. In some embodiments, the receiving features 623, 624 may be configured to release the band straps 621, 622 from the device body 610 (e.g., the housing 601). For example, one or both of the receiving features 623, 624 may include a button or slide, which may be actuated by the user to release a corresponding band strap 621 and 622. One advantage of a releasable lug is that the user can swap between a variety of bands that may be specially configured for a particular use scenario. For example, some bands may be specially configured for sport or athletic activities and other bands may be configured for more formal or professional activities.

The device 100 may also include a rear cover 608 located on the rear-facing surface of the housing 601 of the device body 610. The rear cover 608 may improve the strength and/or scratch resistance of the surface of the device 100. For example, in some embodiments, the rear cover 608 may be formed from a sapphire sheet, zirconia, or alumina material having superior scratch resistance and surface finish qualities. In some cases, the sapphire material has a hardness greater than 6 on the Mohs scale. In some cases, the sapphire material has a hardness of approximately 9 on the Mohs scale. Due to the superior strength of the sapphire material, a cover glass formed from a sapphire sheet may be very thin. For example, the thickness of a sapphire cover sheet may be less 300 microns thick. In some cases, the thickness of a sapphire cover sheet may be less than 100 microns thick. In some cases, the thickness of a sapphire cover sheet may be less than 50 microns thick. In some embodiments, the rear cover 608 is contoured in shape. For example, the rear cover 608 may have a convex curved surface.

FIG. 7 depicts an example exploded view of various modules and subassemblies of the device 100. As shown in FIG. 7, multiple components are configured to be disposed within and/or attached to the housing 601. The exploded view provided in FIG. 7 depicts one example arrangement of the components of the device 100. However, in other embodiments, arrangement, placement, and/or grouping of the subassemblies and the components of the subassemblies may vary.

In the present example, a main cavity of the housing 601 houses an electronics subassembly 720 and the battery 114 of the device. The electronics subassembly 720 includes one or more electrical circuit assemblies for coupling the various electrical components of the device 100 to each other and to power supplied by the battery 114. The electronics subassembly 720 may also include structural elements or components that provide structural rigidity for the electronics subassembly 720 and/or structural mounting or support for other components disposed within the housing 601. As shown in FIG. 7, within the cavity of the housing 601, the speaker 122, the crown module 642, and the battery 114 are all disposed above the electronics subassembly 720. In the present embodiment the top surface of the speaker 122, the crown module 642, and the battery 114 have a substantially similar height. In some embodiments, the speaker 122, the crown module 642, and the battery 114, when assembled in the housing 601, define an area for the display 120 within the cavity. Thus, as shown in FIG. 7, the display 120 may overlay the speaker 122, the crown module 642, and the battery 114, which overlay the electronics subassembly 720.

As shown in FIG. 7, the cover 609 is configured to fit within a corresponding recess formed within the housing 601. In particular, the cover 609 includes a vertical portion having a height that corresponds to the depth of the recess formed within the housing 601. In this example, the device 100 includes a force sensor 705 disposed between the housing 601 and a cover subassembly 704. As described in more detail below with respect to FIGS. 9 and 10A-B, the force sensor 705 may be configured to detect a force placed on a surface of the cover 609 by detecting a relative deflection between the cover 609 (or cover subassembly 704) and the housing 601. In the present example, the force sensor 705 also forms a gasket or seal between the cover subassembly 704 and the housing 601. In some implementations, the seal is a water-proof or water-resistant seal that helps to prevent water or liquid ingress into the internal cavity of the housing 601. The force sensor 705 may also be used to join the cover subassembly 704 to the housing 601 using an adhesive or film.

In some embodiments, the cover subassembly 704 includes the cover 609 which is disposed above the touch sensor 702 and display 120. In the present example, the touch sensor 702 and the display 120 are attached to each other by an optically clear adhesive layer (OCA). Similarly, an OCA layer is used to attach the touch sensor 702 to the cover 609. Other adhesives or bonding techniques may be used to attach the display 120 and the touch sensor 702 to the cover 609. In some embodiments, the touch sensor 702 is integrated into the display 120 and the display 120 (and integrated touch sensor 702) are attached to the cover 609.

As shown in FIG. 7, the speaker 122 is also disposed within the cavity of the housing 601. The speaker 122 is adapted to mechanically and acoustically interface with a port formed in the side of the housing 601. In some embodiments, the port is configured to prevent a direct path for water or liquid into an acoustic chamber or cavity of the speaker 122. In some embodiments, the device 100 also includes a microphone that is similarly coupled to another port formed in the side of the housing 601. A more detailed description of the speaker 122 and microphone is provided below with respect to the acoustic module of FIG. 20.

In the present example, the haptic device 112 is also disposed within the cavity of the housing 601 proximate to the speaker 122. In some embodiments, the haptic device 112 is rigidly mounted to a portion of the housing 601. A rigid mounting between the housing 601 and the haptic device 112 may facilitate the transmission of vibrations or other energy produced by the haptic device 112 to the user. In the present example, the haptic device 112 includes a moving mass that is configured to oscillate or translate in a direction that is substantially parallel with a rear face of the housing 601. In some implementations, this orientation facilitates the perception of a haptic output produced by the haptic device 112 by a user wearing the device 100. While this configuration is provided as one example, in other implementations, the haptic device 112 may be placed in a different orientation or may be configured to produce a haptic response using a rotating mass or other type of moving mass.

As shown in FIG. 7, the device also includes an antenna subassembly 722. In this example, a portion of the antenna subassembly 722 is disposed within the housing 601 and a portion of the antenna subassembly 722 is disposed within the cover assembly. In some implementations, a portion of the antenna subassembly 722 is disposed relative to a feature formed within the cover 609. An example embodiment is described in more detail below with respect to FIGS. 21A-B.

In the example depicted in FIG. 7, the device 100 also includes a crown module 642 which is disposed in an aperture or hole in the housing 601. When installed, a portion of the crown module 642 is located outside of the housing 601 and a portion of the crown module 642 is disposed within the housing 601. The crown module 642 may be configured to mechanically and/or electrically cooperate with the electronics subassembly 720. A more detailed description of an example crown module is provided below with respect to FIGS. 23 and 24A-B. The housing 601 also includes a button 644, which is disposed in an opening of the housing 601 and may be configured to mechanically and/or electrically cooperate with the electronics subassembly 720.

In the example depicted in FIG. 7, a biosensor module 710 is disposed in an opening formed in the rear surface of the housing 601. In some embodiments, the biosensor module 710 includes the rear cover 608 and may also include a chassis or plate that facilitates attachment of the biosensor module 710 to the housing 601. The chassis or plate or the cover sheet 608 may also include features or elements that facilitate a watertight seal between the biosensor module 710 and the housing 601. For example, the rear cover 608 may include a shelf or flange that may be used to form a seal between the biosensor module 710 and the housing 601. As described in more detail below with respect to FIG. 16, the biosensor module 710 may include one or more light sources, one or more photodetectors, and one or more electrodes or conductive elements that are configured to detect and measure a physiological condition or property of the user.

In some embodiments, the rear cover 608 has an edge that protrudes outwardly from the back surface of the housing 601. The rear cover 608 may also have a convex curved area located between the edges of the rear cover 608. The convex curved area of the rear cover 608 may include one or more windows or apertures that provide operational access to one or more internal components located within the housing 601. In some embodiments, the windows have a curvature that matches the curvature of the convex curved area of the rear cover.

2. Example Housing

As described above, a wearable electronic device may include a device body that includes a housing or enclosure shell. As previously described, the housing may function as a chassis that physically integrates the various components of the device. The housing may also form a protective shell or housing for the components and function as a barrier against moisture or debris. In the present examples, the housing is formed as a uni-body, unitary, or single body or component. A single-body construction may be advantageous by providing mounting features directly into the housing, which may reduce space, reduce part count, and increase structural rigidity as compared to some alternative configurations. Additionally, a single-body construction may improve the housing's ability to prevent the ingress of moisture or debris by reducing or eliminating seams or joints between external components.

FIG. 8 depicts an example housing 601 in accordance with some embodiments. In the present example, the housing 601 is formed as a single body or component. As shown in FIG. 8, the housing 601 is formed as a single part or body. The housing 601 may be formed, for example, by machining or shaping a solid or cast blank having the approximate shape of the housing 601. In some implementations, the housing 601 may be configured to provide structural integrity for potentially delicate internal components and also withstand a reasonable impact.

In the present embodiment, the housing 601 is formed as a uni-body, unitary, or single-body construction having a flat bottom portion 801 and a top portion including flange 812. The top portion defines an internal cavity 805, which is surrounded by four sides 802a-d that are integrally formed with the bottom portion 801. The internal cavity 805 can also be described as being defined by the top portion, the four sides 802*a-d* and the bottom portion 801. In this example, the internal cavity 805 has a rectangular (square) shape, although the specific shape may vary with different implementations. In the present example, the four sides 802*a-d* define a curved side portion of the housing 601 that extends from the bottom portion 801 to the top portion of the housing 601. Each side 802*a-d* is orthogonal to an adjacent side and each side 802*a-d* is connected to an adjacent side by a rounded corner. For example, side 802*a* is orthogonal to two adjacent sides 802*b* and 802*d* and is connected to those sides by respective rounded corners. The shape or contour of the rounded corners may correspond to the curvature of the curved portion of the housing 601. Specifically, the curvature of the rounded corners may match or correspond to the curvature of the continuous external surface formed by the housing 601 and the cover 609, as described above with respect to FIG. 6.

The sides 802*a-d* may vary in thickness in order to provide the structural rigidity for the device. In general, areas of high stress may have an increased material thickness as compared to areas of low stress, which may have a reduced material thickness. In particular, portions of the sides 802*a-d* near the bottom portion 801 may have an increased thickness as compared to portions of the sides 802*a-d* located further away from the bottom portion 801. This configuration may improve the structural rigidity and overall stiffness of the housing 601.

As shown in FIG. 8, one or more mounting features may be formed directly into the housing 601, which may reduce the number of parts and also enhance the structural integrity of the device. As shown in FIG. 8, receiving features 623, 624 may be formed as channels or openings that are configured to receive an end of a band (e.g., a lug) having a mating feature. As described above with respect to FIG. 5, the receiving features 623, 624 may be standardized and configured to work with a system of interchangeable components. Forming the receiving features 623, 624 directly into the housing 601 may reduce parts and also facilitate structural rigidity of the device.

In the example depicted in FIG. 8, the housing 601 can be described as having two ends (a first end and a second end opposite the first end), and a first side and a second side opposite the first side, the sides being continuous with the ends. In this example, the first and second ends and the first and second sides having an outwardly curved three-dimensional shape. In this example, the receiving feature 623 is formed from a first groove situated in the first end. Similarly, the receiving feature 624 is formed from a second groove situated in the second end. In the present example the grooves have openings at the interface of the first and second sides and first and second ends. As shown in FIG. 8 the groove also has an inwardly curved concave three-dimensional shape with an undercut feature. For example, the middle portion of the groove of receiving features 623, 624 may have a width that is greater than the opening of the receiving features 623, 624. In some embodiments, the upper portion of the housing overhangs the lower portion of the housing at the groove opening. In the example depicted in FIG. 8, the groove is cut into a solid portion of the housing such that the groove forms a continuous interior shape.

The geometry of the receiving features may be located with respect to other features or components of the device. In the example depicted in FIG. 8, at least a portion of the groove of the receiving features 623, 624 may be disposed underneath the cover (item 609 of FIGS. 6-7). With respect to FIG. 6, the groove of the receiving features 623, 624 is located underneath the opening for the cover, which is defined by the sealing ledge 810 and flange 812 formed in the upper portion of the housing 601. In some embodiments, the length of the groove extends further than the width of the opening configured to receive the cover (and thus the cover, when assembled). In some embodiments, the grooves are formed at an angle relative to the centerline of the housing. In some cases, the angle is approximately 5 degrees. In some embodiments, the groove is located underneath the centerline of the housing 601. In some embodiments, the groove is angled upward toward the top of the housing 601 and inward toward the center of the housing 601. The groove may angle upward and cross the centerline of the housing. In some cases, the groove crosses the vertical centerline of the housing 601.

In the present embodiment, the housing 601 also includes an aperture 821 formed into the side 802*c* of the housing 601 for attaching a crown or crown module (item 642 of FIGS. 6-7). In some embodiments, the aperture 821 for the crown is offset upwardly from the centerline of the housing 601. In some embodiments, the aperture 821 for the crown is positioned such that an upper portion of a crown (when installed) is higher than the interface of cover 609 and housing 601. With respect to FIG. 6, the interface may correspond to the upper edge of the flange 812.

The housing 601 also includes an opening 822 formed into the side 802*c* of the housing 601 for attaching the button (item 644 of FIGS. 6-7). In some embodiments, the aperture 821 for the crown and the opening 822 for the button are disposed with the length defined by a flat part of the cover. In some embodiments, the aperture 821 for the crown is disposed above the centerline of the housing 601 and the opening 822 for the button is disposed below the centerline of the housing 601. In some embodiments, the aperture 821 for the crown and the opening 822 for the button are disposed on a curved surface of the housing 601. The housing 601 may also include various other internal features, including threaded features and bosses, for attaching other internal components of the device.

In some cases, the housing 601 may be formed as a single-piece or integral enclosure shell to enhance the structural rigidity and/or liquid-sealing properties of the device. As described above with respect to FIGS. 6 and 7, the housing 601 may be integrated with a cover (e.g., crystal) and other external components to provide a substantially sealed housing. In the present embodiment, the housing 601, includes a sealing ledge 810 formed around the perimeter of the main cavity 805 formed within the housing 601. In some embodiments, the sealing ledge 810 (and thus the cover when installed) is located in the center of the housing 601. The sealing ledge 810 may be defined by a substantially flat portion 811 that is adapted to form a seal between the housing 601 and another component (e.g., the force sensor 705 or cover 609 of FIGS. 6-7). The sealing ledge 810 may be formed at a depth that is substantially similar or corresponds to the thickness of the mating cover.

As shown in FIG. 8, the sealing ledge 810 may also include flange 812 that protrudes from the flat portion and forms a continuous surface with the side walls 802*a-d*. In some cases, the flange 812 is configured to cooperate with the cover (item 609 of FIGS. 6-7) to form a substantially continuous surface. In some implementations, the sides 802*a-d* and the cover or crystal are configured to cooperate or mechanically interface to improve the strength and the water sealing properties of the device.

As also shown in FIG. 8, an opening or aperture 815 may be formed in the bottom portion 801 of the housing 601. In some embodiments, the opening or aperture 815 is located at the center of the housing 601. As described above with respect to FIG. 7, the aperture 815 may be used to integrate a sensor array or other module used to collect measurements that may be used to compute a health metric or other health-related information. The present embodiment may be advantageous by integrating multiple components in a single opening 815, which may facilitate a water-proof or water-resistant property of the device. Additionally, by integrating a sensor array into a module that attaches via the opening 815, same housing 601 may be used with a variety of sensing configurations or arrays. For example, the number or sensors or components may be increased or decreased without modifying the housing 601. This may allow for flexibility in the product development and may facilitate upgrades as new sensing configurations are available.

As previously discussed above with respect to FIGS. 6-7, the housing 601 may also be configured to serve as a protective housing for one or more acoustic elements, such as a microphone or speaker. Additionally, in some embodiments, the housing 601 may also be configured to inhibit the ingress of foreign particulate or moisture. In particular, the housing 601 may include a speaker port having orifices 831, 832 that are configured to transmit acoustic signals but also prevent the ingress of liquid or other foreign particulate. In the present example, the speaker port includes orifices 831, 832 that are offset with respect to an acoustic chamber or cavity to prevent the direct ingress of liquid into the speaker subassembly or acoustic module. In the present example, a shielding or umbrella portion of the housing, which is substantially free of openings, is formed between the orifices 831, 832, which helps to prevent the direct ingress of liquid. Similarly, the housing 601 includes a microphone port having orifices 833, 834 that are offset from a corresponding acoustic chamber or cavity to prevent the direct ingress of liquid into the microphone subassembly or acoustic module.

In the example depicted in FIG. 8, the orifices 831, 832 of the speaker port are located on one side of the aperture 821 for the crown and the orifices 833, 834 for the microphone are located on the other side of the aperture 821. Both the orifices 831, 832 of the speaker port and the orifices 833, 834 for the microphone are located on a curved portion of the housing 601.

3. Example Force Sensor and Touch Sensor

As discussed previously, a wearable electronic device may include one or more sensors for detecting the location and force of a touch. For the purposes of the following description of the force sensor and touch sensor, the described device 100 is one example of that shown and discussed above with respect to FIGS. 2-7. However, certain features of the device 100 including the external surface geometry, may be simplified or vary with respect to aspects of the device 100 discussed above.

In some embodiments, a force sensor and a touch sensor may be disposed relative to the display of a wearable electronic device for to form a touch-sensitive surface. The following description is provided with respect to individual force and touch sensors that may be used to determine the force and location of a touch, respectively. However, in some embodiments, a single integrated sensor may be used to detect both the force and location of a touch on the device.

In one embodiment, an output from a force sensor may be combined with a touch sensor to provide both location and force of a single touch or of multiple touches on the surface of a device. In an alternative embodiment, a hybrid or integrated force and touch sensor may be used to sense both touch force and location of a single touch or of multiple touches. In either embodiment, by sensing both the force and location of a touch, multiple types of user input may be generated and interpreted. In one example, a first touch may be correlated with a first force and a first touch location or gesture. Based on the magnitude of the force, the first touch may be interpreted as a first type of input or command. A second touch may be sensed as having a second, different force and a similar location or gesture as the first touch. Based in part on the magnitude of the second force, the second touch may be interpreted as a second type of input or command. Thus, a force sensor (alone or in combination with another touch sensor) may be used to produce different responses or outputs depending on the force of the touch.

The one or more force sensors may be formed from or may be implemented as one or more types of sensor configurations. For example, capacitive and/or strain based sensor configurations may be used alone or in combination to detect and measure the magnitude of a touch. As described in more detail below, a capacitive force sensor may be configured to detect the magnitude of a touch based on the displacement of a surface or element on the device. Additionally or alternatively, a strain-based force sensor may be configured to detect the magnitude of a touch based on a deflection of the surface, such as the cover glass.

By way of example, the force sensor may include a capacitive force sensor, which may be formed from one or more capacitive plates or conductive electrodes that are separated by a compressible element or other compliant member. As a force is applied to a surface of the device, the compressible element may deflect resulting in a predictable change in the capacitance between the plates or electrodes. In some implementations, a capacitive force sensor may be formed from transparent materials and disposed over the display. In other implementations, a capacitive force sensor may be formed from non-transparent materials and disposed beneath or around the perimeter of a display.

Figure 9:
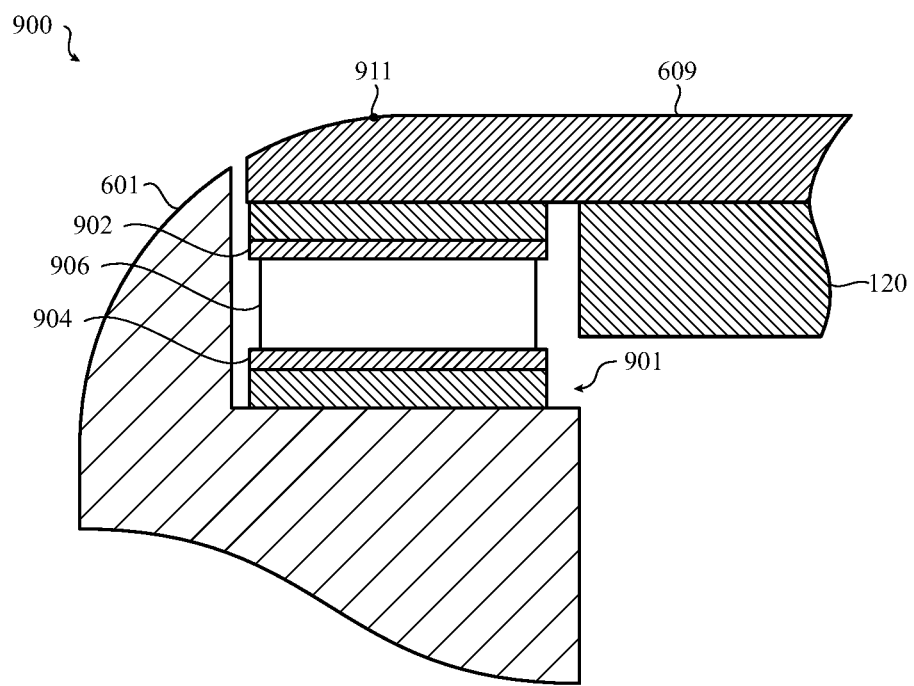
FIG. 9 depicts an example force sensor configured to use a capacitive measurement.

FIG. 9 depicts a detail cross-sectional view of a portion of a force sensor 900 that may be arranged around the perimeter of a display 120. As shown in FIG. 9, a force-sensing structure 901 of the force sensor 900 may be disposed beneath the cover 609 and along the side of an edge or the perimeter of the display 120. In this example, the force sensor 900 is configured to detect and measure the force of a touch on the surface 911 of the cover 609. In the present embodiment, a first capacitive plate 902 is fixed with respect to the cover 609. A second, lower capacitive plate 904 is fixed with respect to the housing 601 and may be disposed on a shelf or mounting surface located along the perimeter of the device. The first capacitive plate 902 and the second capacitive plate 904 are separated by a compressible element 906.

In the configuration depicted in FIG. 9, a touch on the surface 911 of the device may cause a force to be transmitted through the cover 609 of the device and to the force sensor 900. In some cases, the force causes the compressible element 906 to compress, thereby bringing the first capacitive plate 902 and the second capacitive plate 904 closer together. The change in distance between the first and second capacitive plates 902, 904 may result in a change of capacitance, which may be detected and measured. For example, in some cases, a force-sensing circuit may measure this change in capacitance and output a signal that corresponds to the measurement. A processor, integrated circuit or other electronic element may correlate the circuit output to an estimate of the force of the touch. Although the term "plate" may be used to describe certain elements, such as the capacitive plates or conductive electrodes, it should be appreciated that the elements need not be rigid but may instead be flexible (as in the case of a trace or flex).

Figure 10A:
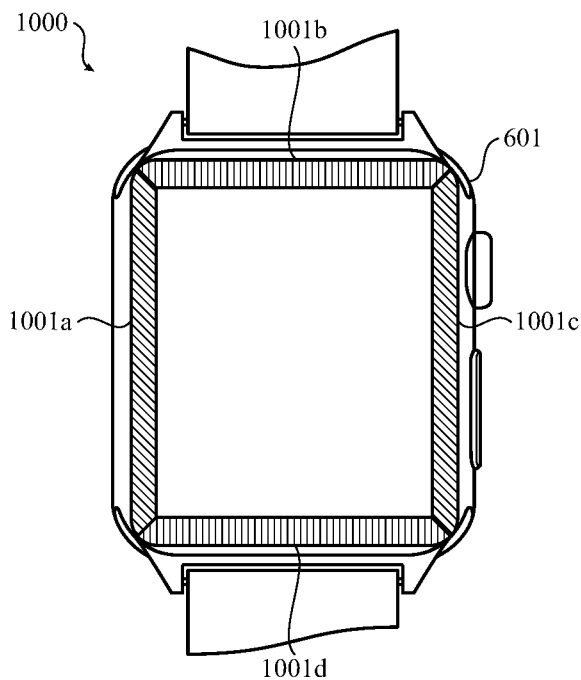
FIGS. 10A-B depict plan views of example force sensors.

FIG. 10A depicts an example configuration of the force sensor 1000 having four individual force-sensing structures 1001a-d arranged around the perimeter of a display in a device. For the sake of clarity, the crystal, display, and other elements of the device are omitted from the depiction of FIG. 10A. Each of the force-sensing structures 1001a-d may be formed from a pair of capacitive plates separated by a compressible element. Additionally, each force-sensing structure 1001a-d may be separated by a small gap at or near the corners of the opening in the housing 601. In the example depicted in FIG. 10A, the four individual force-sensing structures 1001a-d may each be operatively coupled to force-sensing circuitry that is configured to detect a change in the capacitance of each force-sensing structure 1001a-d. Using the example arrangement depicted in FIG. 10A, the approximate location of the touch may be determined by comparing the relative change in capacitance of each force-sensing structure 1001a-d. For example, a change in capacitance of structure 1001b that is larger as compared to a change in capacitance of structure 1001d may indicate that the touch is closer to structure 1001b. In some embodiments, the degree of the difference in the change in capacitance may be used to provide a more accurate location estimate.

Figure 10B:
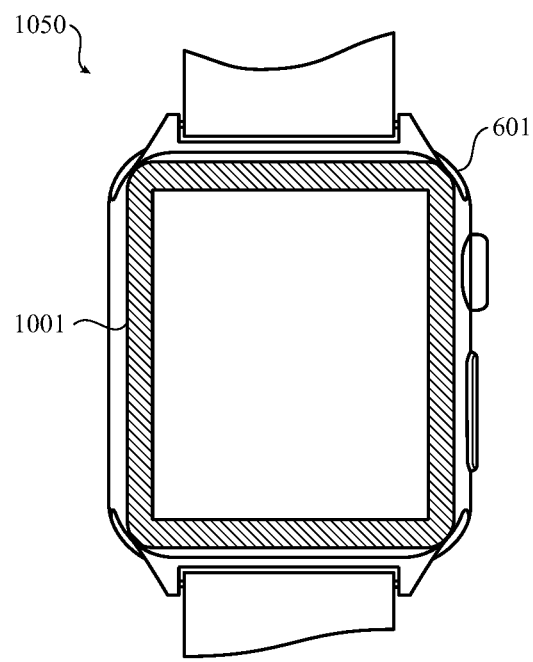

While the configuration shown in FIG. 10A depicts the force-sensing structures as individual elements separated by a small gap, in some embodiments, the force-sensing structure may be formed as a single continuous piece. FIG. 10B depicts a force sensor 1050 formed as a single force-sensing structure 1051 formed as a continuous part along the perimeter of the display. Similar to the example described above, the force-sensing structure 1051 may be operatively coupled to force sensing circuitry that is configured to detect a change in the capacitance of one or more capacitive elements of the force-sensing structure 1051. While the force-sensing structure 1051 is formed as a continuous structure, there may be multiple sensing elements (e.g., capacitive plates) that are disposed within the structure at different locations, and which may be configured to detect deflection or compression of the structure over a portion of entire area of the force-sensing structure 1051. In some embodiments, the force-sensing structure 1051 may also function as a seal or gasket to prevent ingress of moisture or other foreign contaminants into the main cavity of the housing. Additionally, the force-sensing structure 1051 may be integrated with one or more sealing or adhesive layers that also function as a barrier for foreign contaminants.

Figure 11:
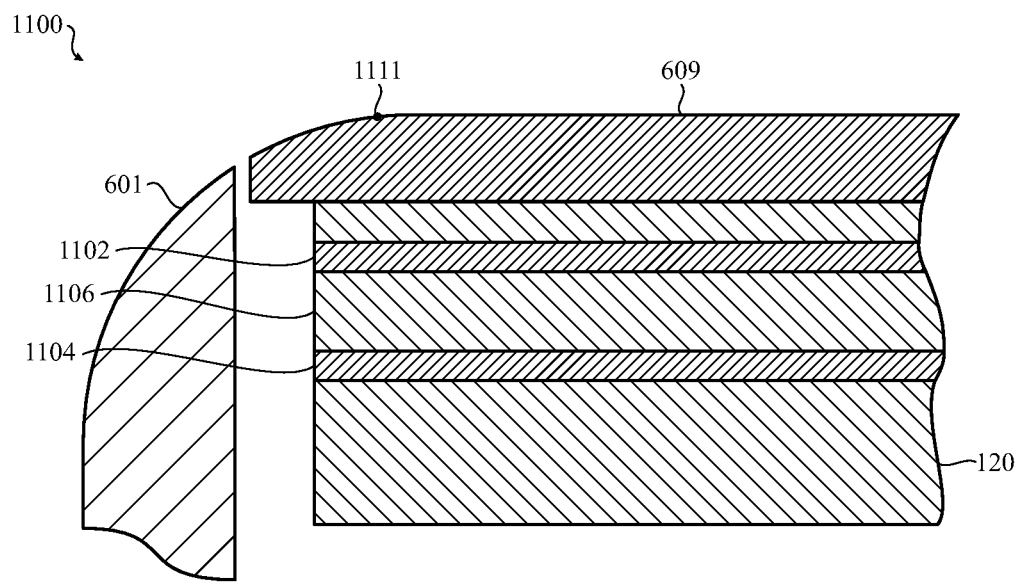
FIG. 11 depicts an example force sensor configured to use a resistive measurement.

As mentioned previously, the force sensor may additionally or alternatively include a strain-based sensing configuration. The strain-based sensing configuration may include, for example, a charge-based or resistive sensor configuration. FIG. 11 depicts a cross-sectional view of a device having an example force sensor 1100 that uses one or more force-sensitive films to detect and measure the force of a touch on a surface 1111 of the cover 609. In this example, the force sensitive film 1102 and 1104 are formed from a transparent material and are disposed relative to a viewable portion of the display 120. As shown in FIG. 11, the force sensor 1100 includes a first force-sensitive film 1102 and a second force-sensitive film 1104 that are separated by one or more intermediate layers 1106. The force-sensitive films 1102, 1104 may be configured to produce different electrical outputs in response to a strain or deflection of the cover 609. In some cases, the intermediate layer 1106 is compressible to allow the first force-sensitive film 1102 to deflect with respect to the second force-sensitive film 1104. In other cases, the intermediate layer 1106 may not be compressible and the first force-sensitive film 1102 deflects in a predictable manner with respect to the second force-sensitive film 1104. While FIG. 11 depicts an example force sensor 1100 having two force-sensitive films, alternative embodiments may include only a single force-sensitive film or, alternatively, include more than two force-sensitive films.

In general, a transparent force-sensitive film may include a compliant material that exhibits an electrical property that is variable in response to deformation or deflection of the film. The transparent force-sensitive film may be formed from a piezoelectric, piezo-resistive, resistive, or other strain-sensitive materials. Transparent resistive films can be formed by coating a substrate with a transparent conductive material. Potential transparent conductive materials include, for example, polyethyleneioxythiophene (PEDOT), indium tin oxide (ITO), carbon nanotubes, graphene, silver nanowire, other metallic nanowires, and the like. Potential substrate materials include, for example, glass or transparent polymers like polyethylene terephthalate (PET) or cyclo-olefin polymer (COP). Typically, when a piezo-resistive or resistive film is strained, the resistance of the film changes as a function of the strain. The resistance can be measured with an electrical circuit. In this way, a transparent piezo-resistive or resistive film can be used in a similar fashion as a strain gauge.

If transparency is not required, then other film materials may be used, including, for example, Constantan and Karma alloys for the conductive film and a polyimide may be used as a substrate. Nontransparent applications include force sensing on track pads or the back of display elements. In general, transparent and non-transparent force-sensitive films may be referred to herein as "force-sensitive films" or simply "films."

Figure 12:
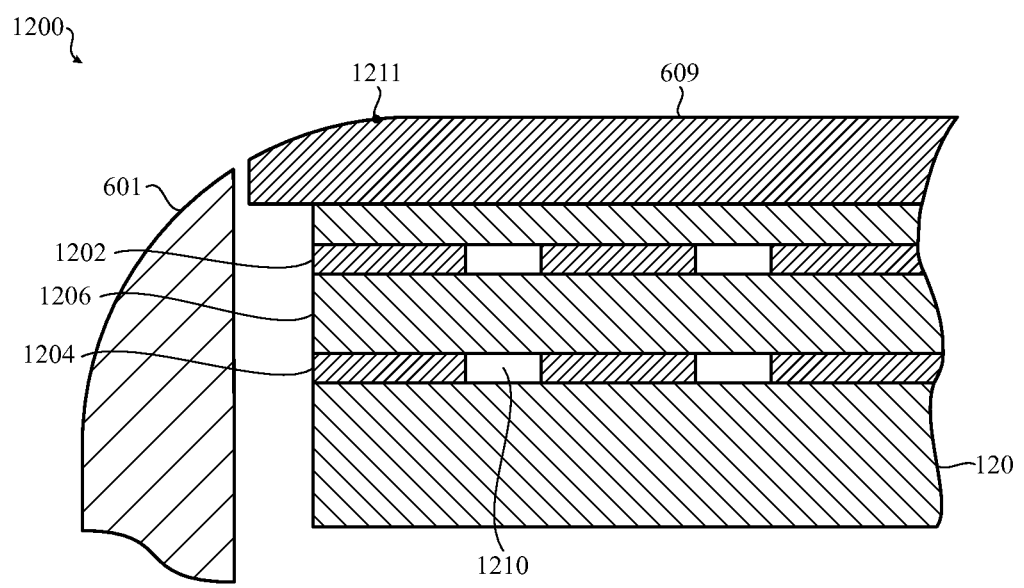
FIG. 12 depicts an example pixelated force sensor configured to use a resistive measurement.

In some embodiments, the force-sensitive film is patterned into an array of lines, pixels, or other geometric elements herein referred to as film elements. The regions of the force-sensitive film or the film elements may also be connected to sense circuitry using electrically conductive traces or electrodes. FIG. 12 depicts a cross-sectional view a device having a strain-based force sensor 1200 formed from one or more strain pixel elements 1202 and 1204 separated by intermediate layer 1206. Each of the pixel elements 1202, 1204 may be separated by a gap 1210. In the present example, each pixel element 1202, 1204 may exhibit a measurable change in an electrical property in response to a force being applied to the device. By way of example, as a force is applied to a surface 1211 on the cover 609, one or more of the pixel elements 1202, 1204 is deflected or deformed. Sense circuitry, which is in electrical communication with the one or more pixel elements 1202, 1204, may be configured to detect and measure the change in the electrical property of the film due to the deflection. Based on the measured electrical property of the pixel elements 1202, 1204, an estimated amount of force can be computed. In some cases, the estimated force may represent the magnitude of a touch on the surface 1211 of the device, and be used as an input to a graphical user interface or other element of the device. Additionally, in some embodiments, the relative strain of the individual pixel elements may be compared to estimate a location of the touch. While FIG. 12 depicts an example force sensor 1200 having two layers of pixel elements, alternative embodiments may include only a single layer of pixel elements or, alternatively, include more than two layers of pixel elements.

The pixel elements 1202, 1204 may be specifically configured to detect strain along one or more directions. In some cases, each pixel element 1202, 1204 includes an array of traces generally oriented along one direction. This configuration may be referred to as a piezo-resistive or resistive strain gauge configuration. In general, in this configuration the force-sensitive-film is a material whose resistance changes in response to strain. The change in resistance may be due to a change in the geometry resulting from the applied strain. For example, an increase in length combined with decrease in cross-sectional area may occur in accordance with Poisson's effect. The change in resistance may also be due to a change in the inherent resistivity of the material due to the applied strain. For example, the applied strain may make it easier or harder for electrons to transition through the material. The overall effect is for the total resistance to change with strain due to the applied force.

Figure 13A:
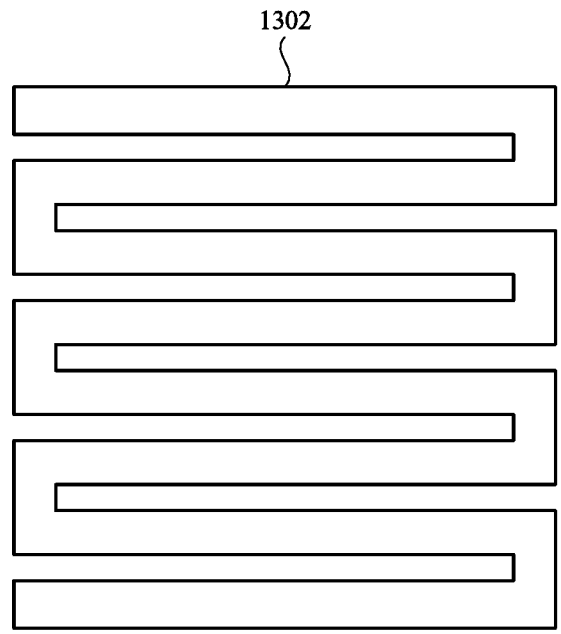
FIGS. 13A-B depict example force sensor structures.
Figure 13B:
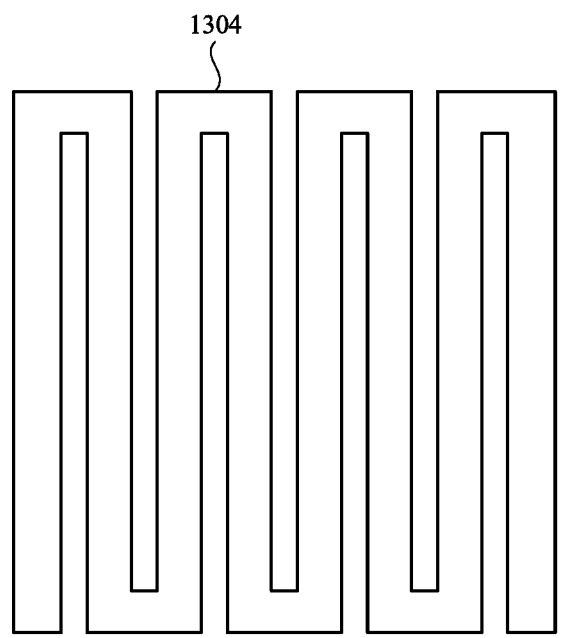

Further, in a piezo-resistive or resistive strain gauge configuration, each pixel may be formed from a pattern of the force-sensitive-film, aligned to respond to strain along a particular axis. For example, if strain along an x-axis is to be measured, the pixel should have a majority of its trace length aligned with the x-axis. By way of example, FIG. 13A depicts a pixel element 1302 having traces that are generally oriented along the x-axis and may be configured to produce a strain response that is substantially isolated to strain in the x-direction. Similarly, FIG. 13B depicts a pixel element 1304 having traces that are generally oriented along the y-axis and may be configured to produce a strain response that is substantially isolated to strain in the y-direction.

In some embodiments, the force-sensitive film may be formed from a solid sheet of material and is in electrical communication with a pattern of electrodes disposed on one or more surfaces of the force-sensitive film. The electrodes may be used, for example, to electrically connect a region of the solid sheet of material to sense circuitry. This configuration may be referred to as a piezo-strain configuration. In this configuration, the force-sensitive film may generate a charge when strained. The force-sensitive film may also generate different amounts of charge depending on the degree of the strain. In some cases, the overall total charge is a superposition of the charge generated due to strain along various axes.

Figure 14A:
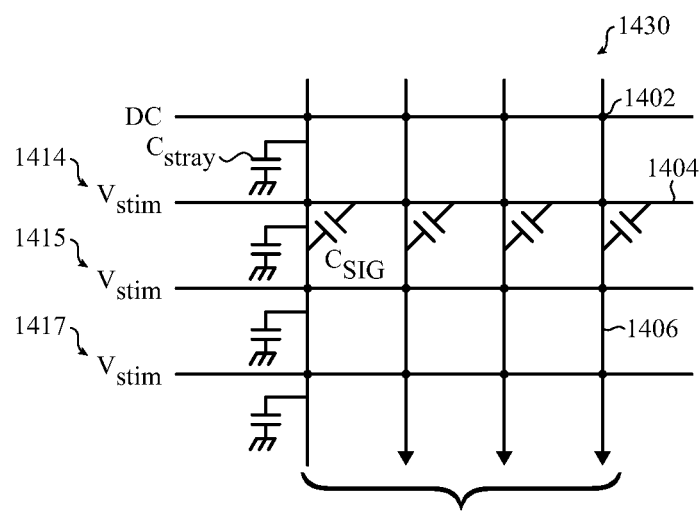
FIGS. 14A-C depict an example touch sensor based on mutual capacitance.

As mentioned previously, a force sensor may be combined with a touch sensor that is configured to detect and measure the location of a touch on the surface of the device. FIG. 14A depicts a simplified schematic representation of an example mutual capacitance touch sensor. As shown in FIG. 14A, a touch sensor 1430 may be formed by an array of nodes 1402 formed at the intersection of an array of drive lines 1404 and sense lines 1406. In this example, stray capacitance $C_{stray}$ may be present at each node 1402 (although FIG. 14A depicts only one $C_{stray}$ for one column for purposes of simplifying the figure). In the example of FIG. 14A, AC stimuli $V_{stim}$ 1414, $V_{stim}$ 1415 and $V_{stim}$ 1417 can be at different frequencies and phases. Each stimulation signal on a row can cause a charge $Q_{sig}=C_{sig} \times V_{stim}$ to be injected into the columns through the mutual capacitance present at the affected nodes 1402. A change in the injected charge ($Q_{sig\_sense}$) can be detected when a finger, palm or other object is present at one or more of the affected nodes 1402. $V_{stim}$ signals 1414, 1415 and 1417 can include one or more bursts of sine waves. Note that although FIG. 14A illustrates rows 1404 and columns 1406 as being substantially perpendicular, they need not be aligned, as described above. Each column 1406 may be operatively coupled to a receive channel of a charge-monitoring circuit.

Figure 14B:
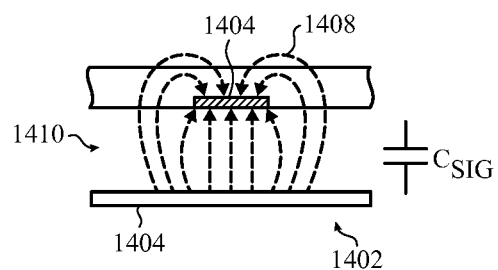

FIG. 14B depicts a side view of an exemplary node in a steady-state (no touch) condition according to examples of the disclosure. In FIG. 14B, electric field lines 1408 between a column 1406 and a row 1404 separated by dielectric 1410 is shown at node 1402.

Figure 14C:
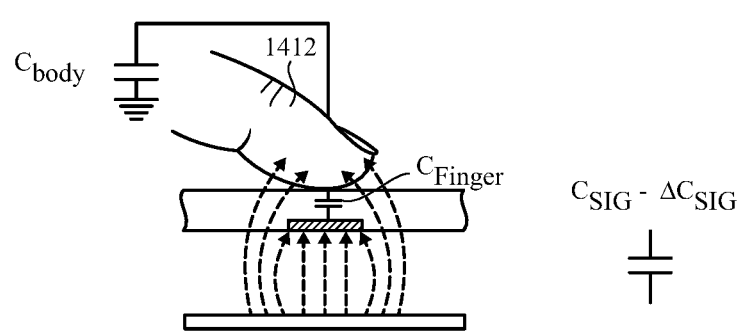

FIG. 14C depicts a side view of an exemplary pixel in a dynamic (touch) condition. An object such as finger 1412 can be placed near node 1402. Finger 1412 can be a low-impedance object at signal frequencies, and can have an AC capacitance $C_{finger}$ from the column trace 1406 to the body. The body can have a self-capacitance to ground $C_{body}$ of about 200 pF, where $C_{body}$ can be much larger than $C_{finger}$. If finger 1412 blocks some electric field lines 1408 between row and column electrodes (those fringing fields that exit the dielectric 1410 and pass through the air above the row electrode), those electric field lines can be shunted to ground through the capacitance path inherent in the finger and the body, and as a result, the steady state signal capacitance $C_{sig}$ can be reduced by $DC_{sig}$. In other words, the combined body and finger capacitance can act to reduce $C_{sig}$ by an amount $DC_{sig}$ (which can also be referred to herein as $C_{sig\_sense}$), and can act as a shunt or dynamic return path to ground, blocking some of the electric field lines as resulting in a reduced net signal capacitance. The signal capacitance at the pixel becomes $C_{sig}-DC_{sig}$, where $DC_{sig}$ represents the dynamic (touch) component. Note that $C_{sig}-DC_{sig}$ may always be nonzero due to the inability of a finger, palm or other object to block all electric fields, especially those electric fields that remain entirely within the dielectric material. In addition, it should be understood that as finger 1412 is pushed harder or more completely onto the touch sensor, finger 1412 can tend to flatten, blocking more and more of the electric fields lines 1408, and thus $DC_{sig}$ may be variable and representative of how completely finger 1412 is pushing down on the panel (i.e., a range from "no-touch" to "full-touch").

Figure 15A:
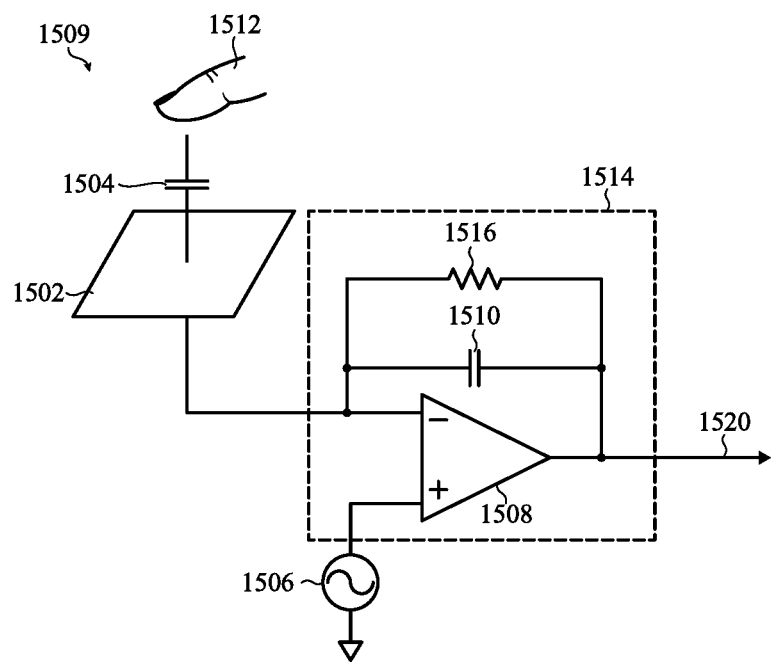
FIGS. 15A-B depict an example touch sensor based on self capacitance.

Additionally or alternatively, the touch sensor may be formed from an array of self-capacitive pixels or electrodes. FIG. 15A depicts an example touch sensor circuit corresponding to a self-capacitance touch pixel electrode and sensing circuit. Touch sensor circuit 1509 can have a touch pixel electrode 1502 with an inherent self-capacitance to ground associated with it, and also an additional self-capacitance to ground that can be formed when an object, such as finger 1512, is in proximity to or touching the touch pixel electrode 1502. The total self-capacitance to ground of touch pixel electrode 1502 can be illustrated as capacitance 1504. Touch pixel electrode 1502 can be coupled to sensing circuit 1514. Sensing circuit 1514 can include an operational amplifier 1508, feedback resistor 1516, feedback capacitor 1510 and an input voltage source 1506, although other configurations can be employed. For example, feedback resistor 1516 can be replaced by a switch capacitor resistor. Touch pixel electrode 1502 can be coupled to the inverting input of operational amplifier 1508. An AC input voltage source 1506 can be coupled to the non-inverting input of operational amplifier 1508. Touch sensor circuit 1509 can be configured to sense changes in the total self-capacitance 1504 of touch pixel electrode 1502 induced by finger 1512 either touching or in proximity to the touch sensor panel. Output 1520 can be used by a processor to determine a presence of a proximity or touch event, or the output can be inputted into a discreet logic network to determine the presence of a touch or proximity event.

Figure 15B:
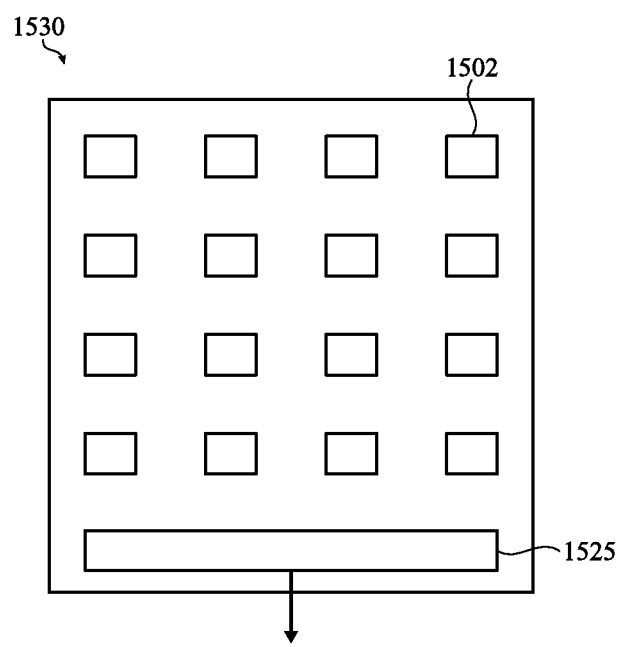

FIG. 15B depicts an example self-capacitance touch sensor 1530. Touch sensor 1530 can include a plurality of touch pixel electrodes 1502 disposed on a surface and coupled to sense channels in a touch controller, can be driven by stimulation signals from the sense channels through drive/sense interface 1525, and can be sensed by the sense channels through the drive/sense interface 1525 as well. After touch controller has determined an amount of touch detected at each touch pixel electrode 1502, the pattern of touch pixels in the touch screen panel at which touch occurred can be thought of as an "image" of touch (e.g., a pattern of fingers touching the touch screen). The arrangement of the touch pixel electrodes 1502 in FIG. 15B is provided as one example; however, the arrangement and/or the geometry of the touch pixel electrodes may vary depending on the embodiment.

As previously mentioned, a force sensor may be implemented alone or in combination with another type of touch sensor to sense both touch force and touch location, which may enable more sophisticated user touch input than using touch location alone. For example, a user may manipulate a computer-generated object on a display using a first type of interaction using a relatively light touch force at a given touch location. The user may also interact with the object using a second type of interaction by using a relatively heavy or sharper touch force at the given location. As one specific example, a user may manipulate or move a computer-generated object, such as a window, using a relatively light touch force. Additionally or alternatively, the user may also select or invoke a command associated with the window using a relatively heavy or sharper touch force. In some cases, multiple types of interactions may be associated with multiple amounts of touch force.

Additionally, it may be advantageous for the user to be able to provide an analog input using a varying amount of force. A variable, non-binary input may be useful for selecting within a range of input values. The amount of force may, in some cases, be used to accelerate a scrolling operation, a zooming operation, or other graphical user interface operation. It may also be advantageous to use the touch force in a multi-touch sensing environment. In one example, the force of a touch may be used to interpret a complex user input performed using multiple touches, each touch having a different magnitude or degree of force. As a specific but non-limiting example, touch and force may be used in a multi-touch application that allows the user to play a varying tone or simple musical instrument using the surface of the device. In such a housing, the force of each touch may be used to interpret a user's interaction with the buttons or keys of a virtual instrument. Similarly, the force of multiple touches can be used to interpret a user's multiple touches in a game application that may accept multiple non-binary inputs at different locations.

4. Sensor or Biosensor Module

As described above with respect to FIG. 2, a wearable electronic device may include one or more sensors that can be used to calculate a health metric or other health-related information. For the purposes of the following description of the biosensor module, the described device 100 is one example of that shown and discussed above with respect to FIGS. 2-7. However, certain features of the device 100 including the external surface geometry, may be simplified or vary with respect to aspects of the device 100 discussed above.

In some embodiments, a wearable electronic device may function as a wearable health assistant that provides health-related information (whether real-time or not) to the user, authorized third parties, and/or an associated monitoring device. The wearable health assistant may be configured to provide health-related information or data such as, but not limited to, heart rate data, blood pressure data, temperature data, blood oxygen saturation level data, diet/nutrition information, medical reminders, health-related tips or information, or other health-related data. The associated monitoring device may be, for example, a tablet computing device, phone, personal digital assistant, computer, and the like.

In accordance with some embodiments, the electronic device can be configured in the form of a wearable electronic device that is configured or configurable to provide a wide range of functionality. As described above with respect to FIG. 2, the wearable electronic device 100 may include a processing units 102 coupled with or in communication with a memory 104, one or more communications channels 108, output devices such as a display 120 and speaker 122, one or more input components 106, and other modules or components. An example wearable electronic device 100 may be configured to provide or calculate information regarding time, health information, biostatistics, and/or status to externally connected or communicating devices and/or software executing on such devices. The device 100 may also be configured to send and receive messages, video, operating commands, and other communications.

Figure 16:
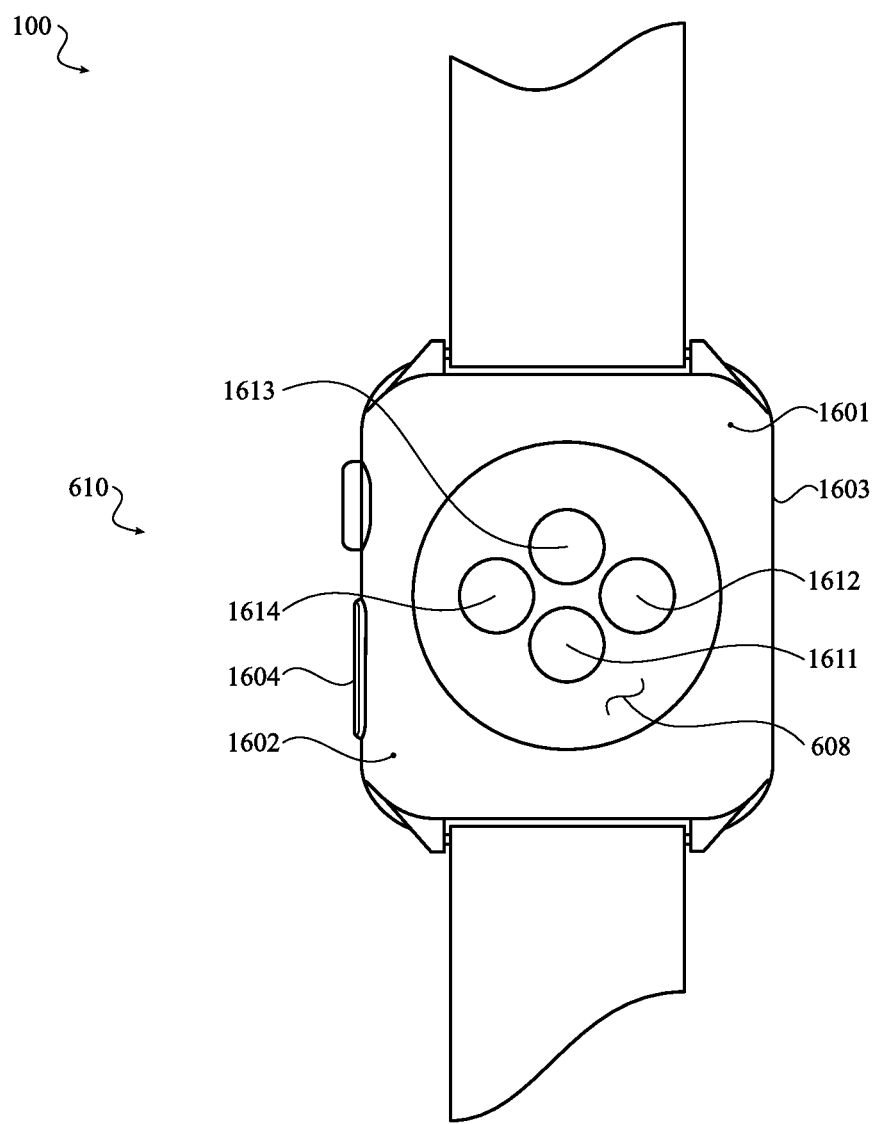
FIG. 16 depicts an example device having biosensors.

With reference to FIG. 16, an example device 100 may include various sensors for measuring and collecting data that may be used to calculate a health metric or other health-related information. As one example, the wearable communication device can include an array of light sources 1611-1613 and a detector 1614 that are configured to function as an optical sensor or sensors. In one example, an optical sensor or sensors may implemented as a pairing of one or more light sources 1611-1613 and the detector 1614. In one example implementation, the detector 1614 is configured to collect light and convert the collected light into an electrical sensor signal that corresponds to the amount of light incident on a surface of the detector 1614. In one embodiment, the detector may be a photodetector, such as a photodiode. In other embodiments, the detector 1614 may include a phototube, photosensor, or other light-sensitive device.

In some cases, the one or more optical sensors may operate as a photoplethysmography (PPG) sensor or sensors. In some instances, a PPG sensor is configured to measure light and produce a sensor signal that can be used to estimate changes in the volume of a part of a user's body. In general, as light from the one or more light sources passes through the user's skin and into the underlying tissue, some light is reflected, some is scattered, and some light is absorbed, depending on what the light encounters. The light that is received by the detector 1614 may be used to generate a sensor signal, which may be used to estimate or compute a health metric or other physiological phenomena.

The light sources may operate at the same light wavelength range, or the light sources can operate at different light wavelength ranges. As one example, with two light sources, one light source may transmit light in the visible wavelength range while the other light source can emit light in the infrared wavelength range. In some cases, a modulation pattern or sequence may be used to turn the light sources on and off and sample or sense the reflected light. With reference to FIG. 16, the first light source 1611 may include, for example, a green LED, which may be adapted for detecting blood perfusion in the body of the wearer. The second light source 1612 may include, for example, an infrared LED, which may be adapted to detect changes in water content or other properties of the body. The third 1613 light source may be a similar type or different types of LED element, depending on the sensing configuration.

The optical (e.g., PPG) sensor or sensors may be used to compute various health metrics, including, without limitation, a heart rate, a respiration rate, blood oxygenation level, a blood volume estimate, blood pressure, or a combination thereof. In some instances, blood may absorb light more than surrounding tissue, so less reflected light will be sensed by the detector of the PPG sensor when more blood is present. The user's blood volume increases and decreases with each heartbeat. Thus, in some cases, a PPG sensor may be configured to detect changes in blood volume based on the reflected light, and one or more physiological parameters of the user may be determined by analyzing the reflected light. Example physiological parameters include, but are not limited to, heart rate, respiration rate, blood hydration, oxygen saturation, blood pressure, perfusion, and others.

While FIG. 16 depicts one example embodiment, the number of light sources and/or detectors may vary in different embodiments. For example, another embodiment may use more than one detector. Another embodiment may also use fewer or more light sources than are depicted in the example of FIG. 16. In particular, in the example depicted in FIG. 16, the detector 1614 is shared between multiple light sources 1611-1613. In one alternative embodiment, two detectors may be paired with two corresponding light sources to form two optical sensors. The two sensors (light source/detector pairs) may be operated in tandem and used to improve the reliability of the sensing operation. For example, output of the two detectors may be used to detect a pulse wave of fluid (e.g., blood) as it passes beneath the respective detectors. Having two sensor readings taken at different locations along the pulse wave may allow the device to compensate for noise created by, for example, movement of the user, stray light, and other effects.

In some implementation, one or more of the light sources 1611-1613 and the detector 1614 may also be used for optical data transfer with a base or other device. For example, the detector 1614 may be configured to detect light produced by an external mating device, which may be interpreted or translated into a digital signal. Similarly, one or more of the light sources 1611-1613 may be configured to transmit light that may be interpreted or translated into a digital signal by an external device.

Returning to FIG. 16, the device 100 may also include one or more electrodes to measure electrical properties of the user's body. In this example, a first electrode 1601 and second electrode 1602 are disposed on the rear face of the device 100. The first 1601 and second 1602 electrodes may be configured to make contact with the skin of the user's wrist when the device is being worn. As shown in FIG. 16, a third electrode 1603 and fourth electrode 1604 may be disposed along a periphery of the device body 610. In the configuration of FIG. 16, the third 1603 and fourth 1604 electrodes are configured to come into contact with the skin of the user's other hand (that is not wearing the device 100). For example, the third 1603 and fourth 1604 electrodes may be contacted when the user pinches the device 100 between two digits (e.g., a forefinger and thumb).

FIG. 16 depicts one example arrangement of electrodes. However, in other embodiments, one or more of the electrodes may be placed in locations that are different than the configuration of FIG. 16. For example, one or more electrodes may be placed on a top surface or other surface of the device 100. Additionally, fewer electrodes or more electrodes may be used to contact the user's skin, depending on the configuration.

Using the electrodes of the device, various electrical measurements may be taken, which may be used to compute a health metric or other health-related information. By way of example, the electrodes may be used to detect electrical activity of the user's body. In some cases, the electrodes may be configured to detect electrical activity produced by the heart of the user to measure heart function or produce an electrocardiograph (ECG). As another example, the electrodes of the device may be used to detect and measure conductance of the body. In some cases, the measured conductance may be used to compute a galvanic skin response (GSR), which may be indicative of the user's emotional state or other physiological condition. By way of further example, the electrodes may also be configured to measure other health characteristics, including, for example, a body fat estimate, body or blood hydration, and blood pressure.

In some embodiments, the optical sensors and electrodes discussed above with respect to FIG. 16 may be operatively coupled to sensing circuitry and the processing units 102 to define a health monitoring system. In this capacity, the processing units 102 may be any suitable type of processing device. In one embodiment, the processing units 102 include a digital signal processor. The processing units 102 may receive signals from the optical sensor(s) and/or electrodes and process the signals to correlate the signal values with a physiological parameter of the user. As one example, the processing units 102 can apply one or more demodulation operations to the signals received from the optical sensor. Additionally, the processing units 102 may control the modulation (i.e., turning on and off) of the light sources according to a given modulation pattern or sequence. The processing units 102 may also be used to calculate one or more biometrics or other heath related information.

In some implementations, the wearable electronic device may also receive sensor data or output from an external device. For example, an external mobile device having a global positioning system (GPS) may relay location information to the wearable device, which may be used to calibrate an activity metric, such as a pedometer or distance calculator. Similarly, sensor output of the wearable electronic device may be transmitted to an external device to compute health-related information. For example, output from an accelerometer in the wearable electronic device may be used determine a body position or gesture, which may be relayed to an external device and used to compute health-related information, such as activity level.

In some embodiments, some or all of the biosensors may be integrated into a module that is separate from and attached to the housing 601 of the device 100. As described above with respect to FIG. 6, in some embodiments, the biosensors are disposed relative to or attached to a rear cover 608 that is formed from an optically transparent material and is configured to be positioned with the opening of the housing 601. In some embodiments, the rear cover 608 is disposed completely within the area of the cover so that the two components completely overlap when viewed from above. In some embodiments, the rear cover 608 has an edge that protrudes outwardly from the back surface of the housing 601. In some embodiments, an edge of the rear cover 608 extends past a flat portion of the back surface of the housing 601. The rear cover 608 may also have a convex, curved outer contour. The rear cover 608 may have a convex shape that is located within the center and surrounded by the edges of the rear cover 608. The convex curved area of the rear cover 608 may include one or more windows or apertures that provide operational access to one or more internal components located within the housing. For example, the rear cover 608 may include an array of windows, each window including an aperture or opening for a respective light source 1611-1613 and/or the detector 1614. In some embodiments, the windows have a curvature that matches the curvature of the convex curved area of the rear cover 608. In some embodiments, rear cover 608 includes a chamfered edge and a curved bottom surface, the windows being disposed within the curved surface. In some embodiments, two openings of the rear cover 608 are located along a first axis (e.g., an x-axis) and two openings are located along a second axis (e.g., a y-axis) that is transverse to the first axis.

5. Example Wireless Communications with External Devices

A wearable electronic device may include a functionality for performing wireless communications with an external device. For the purposes of the following description, the described device 100 is one example of that shown and discussed above with respect to FIGS. 2-7. However, certain features of the device 100, including the external surface geometry, may be simplified or vary with respect to aspects of the device 100 discussed above.

In some embodiments, the wireless communications are performed in accordance with a Near Field Communications (NFC) protocol. The communication may include an identification protocol and a secured data connection that can be used to identify the user, authorize activity, perform transactions, or conduct other aspects of electronic commerce.

Figure 17:
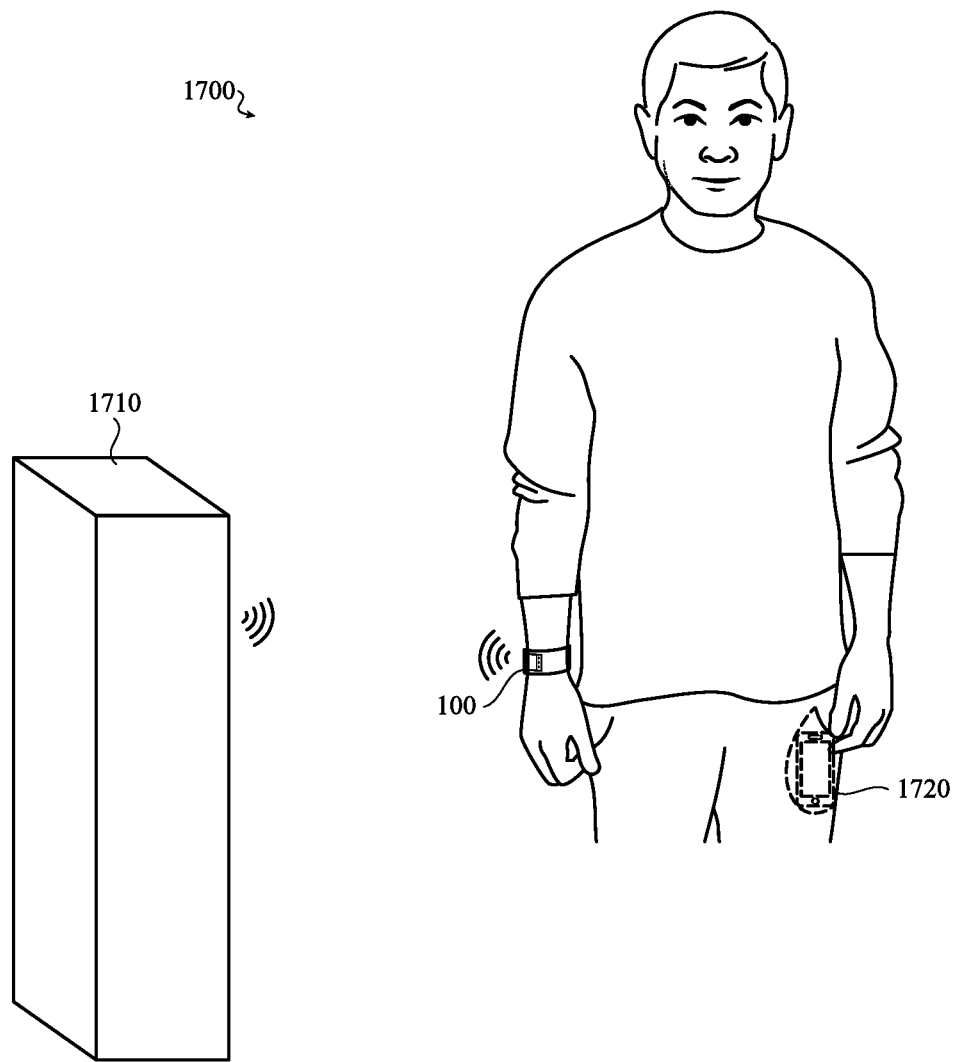
FIG. 17 depicts an example device having wireless communications with an external device.

FIG. 17 depicts an example system 1700 including a device 100 that is located proximate to a station 1710. The station 1710 may include a variety of devices, including, without limitation, a payment kiosk, a vending machine, a security access point, a terminal device, or other similar device. In some cases, the station 1710 is incorporated into a larger system or device. For example, the station 1710 may be incorporated into a security gate of a building or a payment center for a vending system.

As shown in FIG. 17, the device 100 is a wearable electronic device that may be placed proximate to the station 1710. In this example, a second device 1720 is carried by a user, and may also be placed proximate to the station 1710. In some embodiments, the device 100 and/or the second device 1720 includes a radio-frequency identification (RFID) system that is configured to enable one-way or two-way radio-frequency (RF) communications with the station 1710. The one- or two-way communication may include an identification of the device 100 and the station 1710 to initiate a secured data connection between the two devices. The secured data connection may be used to authorize a transaction between the user and an entity that is associated with the station 1710.

In some embodiments, the user may initiate a communication with the station 1710 by placing the device 100 near an active region on the station 1710. In some implementations, the station 1710 is configured to automatically detect the presence of the device 100 and initiate an identification process or routine. The RFID system of the device may include a unique identifier or signature that may be used to authenticate the identity of the user. As previously mentioned, the identification process or routine may be used to establish a secure data connection between the device 100 and the station 1710. The secure data connection may be used to authorize a purchase or download of data to or from the device 100. In some cases, the secure data connection may be used to authorize the transfer of funds from a credit card or financial institution in exchange for a product that is associated with the station 1710. Other transactions or forms of electronic commerce may also be performed using the wireless communication between the device 100 and the station 1710.

6. Example Wireless Power System

As discussed above, a wearable electronic device may include an internal battery that is rechargeable using an external power source. For the purposes of the following description, the described device 100 is one example of that shown and discussed above with respect to FIGS. 2-7. However, certain features of the device 100, including the external surface geometry, may be simplified or vary with respect to aspects of the device 100 discussed above.

One challenge associated with small devices is that it may be difficult to incorporate an electrical port for coupling the device to an external power source. Because wearable electronic devices have limited space for an external connector, it may be advantageous to electrically couple to a device without a cable or external connector. In at least some embodiments, the wearable electronic device described herein may be configured to operate as a receiver in a wireless power transfer system.

A wireless power transfer system, one example of which is an inductive power transfer system, typically includes a power-transmitting structure to transmit power and a power-receiving structure to receive power. In some examples, a power-receiving electronic device includes or otherwise incorporates an inductive power-receiving element configured to receive wireless power and/or charge one or more internal batteries. Similarly, a charging device may include or otherwise incorporate an indicative power-transmitting element configured to wirelessly transmit power to the power-receiving electronic device. The charging device may be configured as a base or dock on which the power-receiving electronic device rests or to which it physically connects in some embodiments. In other embodiments, the charging device may be proximate the electronic device but not necessarily touching or physically coupled.

In many examples, the battery-powered electronic device may be positioned on an external surface of the power-transmitting device, otherwise referred to as a dock. In these systems, an electromagnetic coil within the dock (e.g., transmit coil) may produce a time-varying electromagnetic flux to induce a current within an electromagnetic coil within the electronic device (e.g., receive coil). In many examples, the transmit coil may transmit power at a selected frequency or band of frequencies. In one example the transmit frequency is substantially fixed, although this is not required. For example, the transmit frequency may be adjusted to improve inductive power transfer efficiency for particular operational conditions. More particularly, a high transmit frequency may be selected if more power is required by the electronic device and a low transmit frequency may be selected if less power is required by the electronic device. In other examples, a transmit coil may produce a static electromagnetic field and may physically move, shift, or otherwise change its position to produce a spatially-varying electromagnetic flux to induce a current within the receive coil.

The electronic device may use the received current to replenish the charge of a rechargeable battery or to provide power to operating components associated with the electronic device. Thus, when the electronic device is positioned on the dock, the dock may wirelessly transmit power at a particular frequency via the transmit coil to the receive coil of the electronic device.

A transmit coil and receive coil may be disposed respectively within housings of the dock and electronic device so as to align along a mutual axis when the electronic device is placed on the dock. If misaligned, the power transfer efficiency between the transmit coil and the receive coil may decrease as misalignment increases. Accordingly, in many examples, the wireless power transfer system may include one or more alignment assistance features to effect alignment of the transmit and receive coils along the mutual axis.

Figure 18:
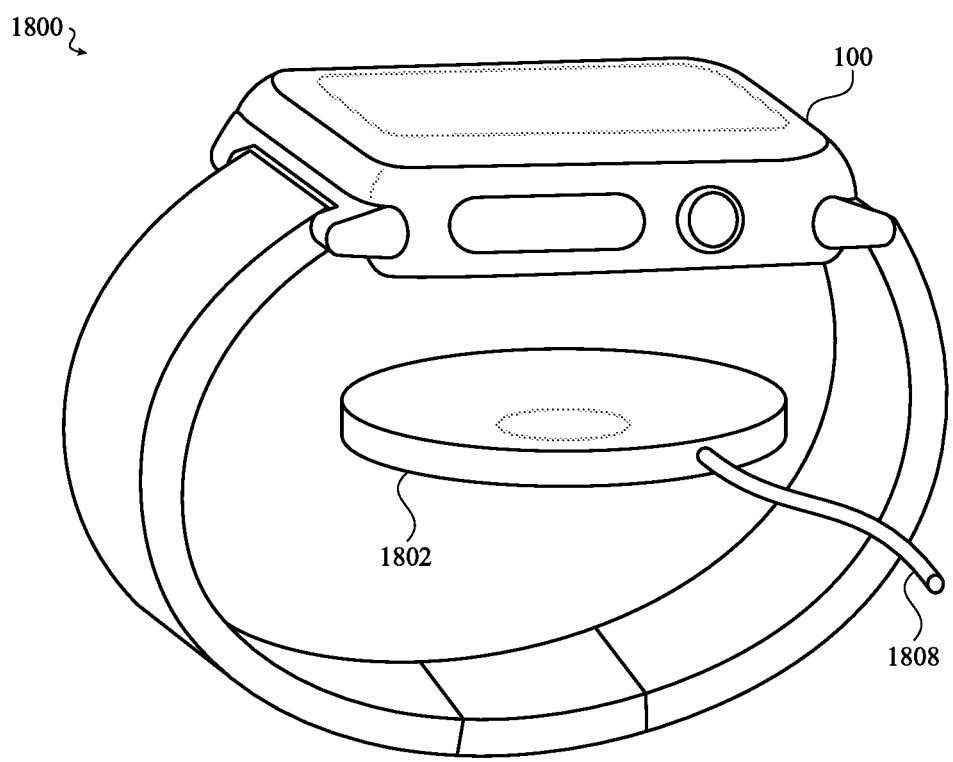
FIG. 18 depicts an example electronic device and example dock of an inductive charging system.

FIG. 18 depicts a front perspective view of an example wireless power transfer system 1800 in an unmated configuration. The illustrated embodiment shows an inductive power transmitter dock 1802 that is configured to couple to and wirelessly transmit power to an inductive power receiver accessory, in this case device 100. The wireless power transfer system 1800 may include one or more alignment assistance features to effect alignment of the device 100 with the dock 1802 along a mutual axis. For example, the housings of the dock 1802 and the device 100 may assist with alignment. In one implementation, a portion of the housing of the device 100 may engage and/or interlock with a portion of the housing of the dock 1802 in order to effect the desired alignment. In some embodiments, a bottom portion of the device 100 may be substantially convex and a top surface of the dock 1802 may be substantially concave. In other examples, the interfacing surfaces of the dock 1802 and the device 100 may be substantially flat, or may include one or more additional housing features to assist with effecting mutual alignment.

In some embodiments, one or more actuators in the dock 1802 and/or device 100 can be used to align the transmitter and receiver devices. In yet another example, alignment assistance features, such as protrusions and corresponding indentations in the housings of the transmitter and receiver devices, may be used to align the transmitter and receiver devices. The design or configuration of the interface surfaces, one or more alignment assistance mechanisms, and one or more alignment features can be used individually or in various combinations thereof.

Alignment assistance can also be provided with one or more magnetic field sources. For example, a permanent magnet within the dock 1802 may attract a permanent magnet within the device 100. In another example, a permanent magnet within the device 100 may be attracted by a magnetic field produced by the dock 1802. In further examples, multiple alignment assistance features may cooperate to effect alignment of the transmit and receive coils. Power transfer efficiency may also decrease if the power consumption of the electronic device changes (e.g., the electronic device transitions from a trickle charge mode to constant current charge mode) during wireless power transfer.

As discussed previously with respect to FIG. 2, the device 100 may include a processor coupled with or in communication with a memory, one or more communication interfaces, output devices such as displays and speakers, and one or more input devices such as buttons, dials, microphones, or touch-based interfaces. The communication interface(s) can provide electronic communications between the communications device and any external communication network, device or platform, such as, but not limited to, wireless interfaces, Bluetooth interfaces, Near Field Communication interfaces, infrared interfaces, USB interfaces, Wi-Fi interfaces, TCP/IP interfaces, network communications interfaces, or any conventional communication interfaces. The device 100 may provide information regarding time, health, statuses or externally connected or communicating devices and/or software executing on such devices, messages, video, operating commands, and so forth (and may receive any of the foregoing from an external device), in addition to communications.

In the example depicted in FIG. 18, the dock 1802 may be connected to an external power source, such as an alternating current power outlet, by power cord 1808. In other embodiments, the dock 1802 may be battery operated. In still further examples, the dock 1802 may include a power cord 1808 in addition to an internal or external battery. Similarly, although the embodiment is shown with the power cord 1808 coupled to the housing of the dock 1802, the power cord 1808 may be connected by any suitable means. For example, the power cord 1808 may be removable and may include a connector that is sized to fit within an aperture or receptacle opened within the housing of the dock 1802.

Although the device 100 is shown in FIG. 18 as larger than the dock 1802, the depicted scale may not be representative of all embodiments. For example, in some embodiments the dock 1802 may be larger than the device 100. In still further embodiments the two may be substantially the same size and shape. In other embodiments, the dock 1802 and device 100 may take separate shapes.

Figure 19:
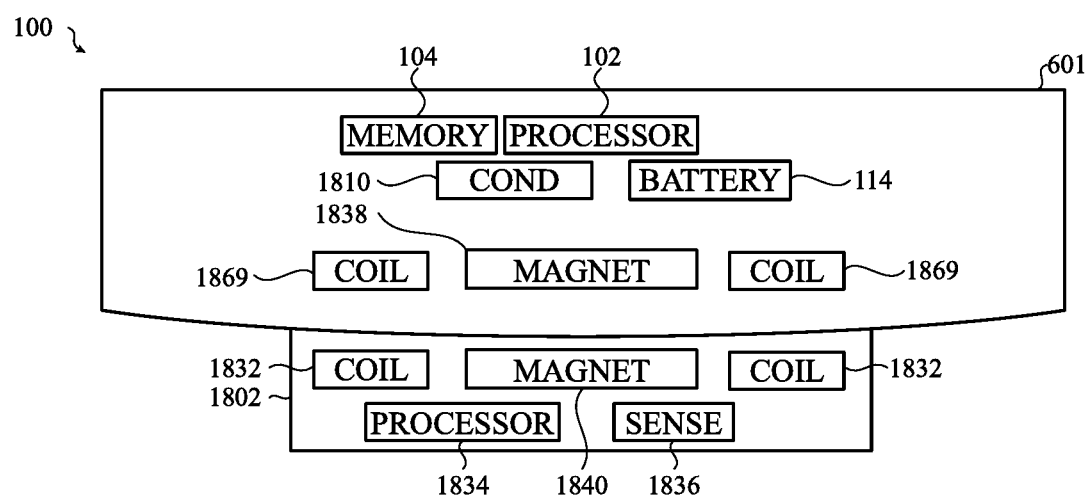
FIG. 19 depicts a block diagram of an example inductive charging system.

FIG. 19 depicts a simplified block diagram of relevant aspects of the device 100 and dock 1802. It may be appreciated that certain components of both the dock 1802 and device 100 are omitted from the figure for clarity. Likewise, the positions of the elements that are shown are meant to be illustrative rather than necessarily portraying a particular size, shape, scale, position, orientation, or relation to one another, although some embodiments may have elements with one or more of such factors as illustrated.

As described previously with respect to FIG. 2, the device 100 may include one or more electronic components located within the housing 601. For clarity, some of the components and modules described or depicted in various embodiments are omitted from the depiction of FIG. 19. As shown in FIG. 19, the device 100 may include an internal battery 114 that may be used to provide power to the various internal components of the device 100. As described previously, the internal battery 114 may be rechargeable by an external power supply. In the present example, the internal battery 114 is operably connected to a receive coil 1869 via power conditioning circuit 1810.

In the present example, the device 100 includes a receive coil 1869 having one or more windings for inductively coupling with a transmit coil 1832 of the dock 1802. The receive coil 1869 may receive power wirelessly from the dock 1802 and may pass the received power to a battery 114 within the device 100 via power conditioning circuit 1810. The power conditioning circuit 1810 may be configured to convert the alternating current received by the receive coil 1869 into direct current power for use by other components of the device. In one example, the processing units 102 may direct the power, via one or more routing circuits, to perform or coordinate one or more functions of the device 100 typically powered by the battery 114.

As shown in FIG. 19, the dock 1802 includes a transmit coil 1832 having one or more windings. The transmit coil 1832 may transmit power to the device 100 via electromagnetic induction or magnetic resonance. In many embodiments, the transmit coil 1832 may be shielded with a shield element that may be disposed or formed around portions of the transmit coil 1832. Similarly, the receive coil 1869 may also include a shield element that may be disposed or formed around a portion of the receive coil 1869.

As shown in FIG. 19, the dock 1802 also includes a processor 1834 that may be used to control the operation of or coordinate one or more functions of the dock 1802. In some embodiments, the dock 1802 may also include one or more sensors 1836 to determine whether the device 100 is present and ready to receive transmitted power from the dock 1802. For example, the dock 1802 may include an optical sensor, such as an infrared proximity sensor. When the device 100 is placed on the dock 1802, the infrared proximity sensor may produce a signal that the processor 1834 uses to determine the presence of the device 100. The processor 1834 may, optionally, use another method or structure to verify the presence of the electronic device via sensor 1836. Examples of different sensors that may be suitable to detect or verify the presence of device 100 may include a mass sensor, a mechanical interlock, switch, button or the like, a Hall effect sensor, or other electronic sensor. Continuing the example, after the optical sensor reports that the device 100 may be present, the processor 1834 may activate a communication channel to attempt to communicate with the device 100.

As illustrated in FIG. 19, a bottom surface of the housing of the device 100 may partially contact a top surface of the dock housing. In some implementations, the interfacing surfaces of the device 100 and the dock 1802 may be formed with complementary geometries. For example, as depicted in FIG. 19, the bottom surface of the device 100 is convex and the top surface of the dock 1802 is concave, following the same curvature as the bottom surface of the device 100. In this manner, the complementary geometries may facilitate alignment of the electronic device and dock for efficient wireless power transfer.

In some embodiments, the dock 1802 and device 100 may include other alignment assistance features. For example the device 100 may include an alignment magnet 1838 which is positioned and oriented to attract a corresponding alignment magnet 1840 within the dock 1802. In some cases, when the device 100 is positioned proximate the dock 1802, the alignment magnets 1838, 1840 may be mutually attracted, thereby affecting alignment of the portable electronic device 100 and the dock 1802 along a mutual axis. In other examples, the dock 1802 may include a ferromagnetic material in place of the alignment magnet 1840. In these examples, the alignment magnet 1838 may be attracted to the ferromagnetic material. In still further cases, the receive coil 1869 or transmit coil 1832 may produce a static magnetic field that either attracts or repels either or both of the alignment magnets 1838, 1840.

As shown in FIG. 19, the alignment magnets 1838, 1840 may be positioned within a respective coil 1869, 1832. When the alignment magnets 1838, 1840 are drawn together, the coils 1869, 1832 may be placed into alignment. Additionally, the complementary geometries of the device 100 and the dock 1802 may further facilitate alignment when the alignment magnets 1838, 1840 are drawn together.

7. Example Acoustic Module

As described above, the device may include one or more devices for transmitting and receiving acoustic energy. For the purposes of the following description of the acoustic module, the described device 100 is one example of that shown and discussed above with respect to FIGS. 2-7. However, certain features of the device 100, including the external surface geometry, may be simplified or vary with respect to aspects of the device 100 discussed above. As previously discussed, in some embodiments, the device may include a speaker for transmitting acoustic energy and/or a microphone for receiving acoustic energy. For the purposes of the following description, a speaker device and a microphone are referred to generically as an acoustic module, which may be configured to transmit and/or receive acoustic energy depending on the particular implementation.

Figure 20:
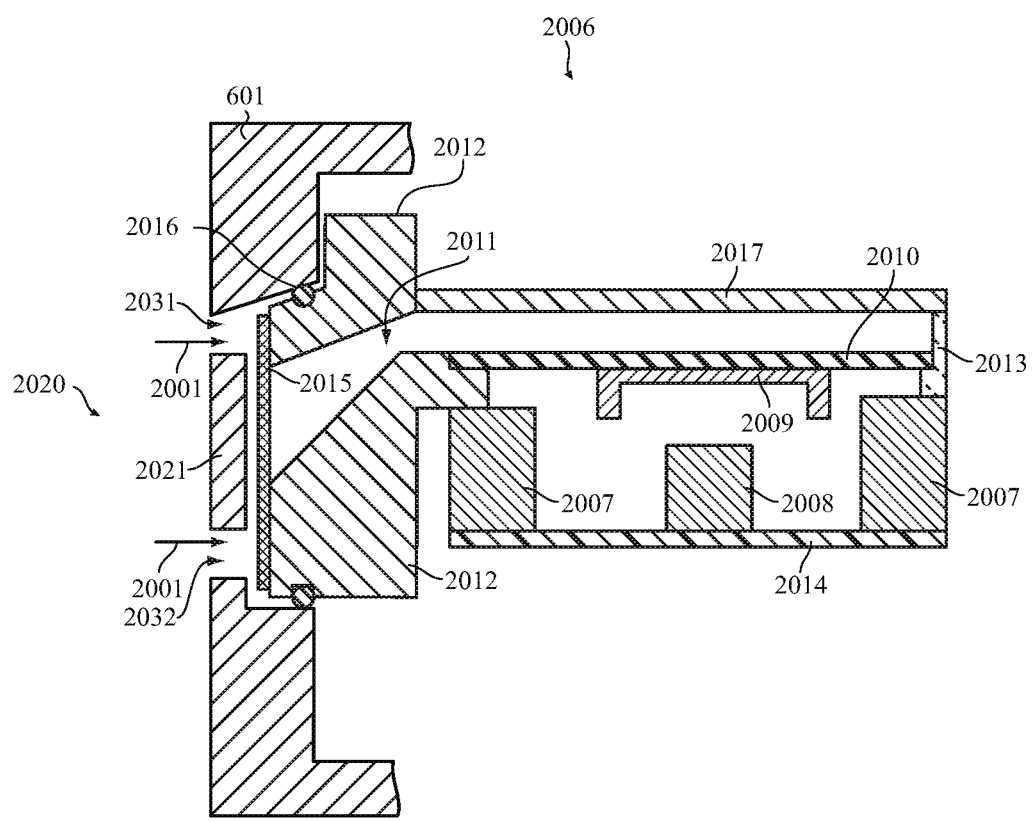
FIG. 20 depicts an example acoustic module.

FIG. 20 depicts a simplified schematic cross-sectional view of a first embodiment of a device having an acoustic module 2006. The representation depicted in FIG. 20 is not drawn to scale and may omit some elements for clarity. The acoustic module 2006 may represent either a portion of a speaker and/or microphone device described above with respect to the electronic device 100 of FIG. 2.

As shown in FIG. 20, an acoustic port 2020 may be formed in the housing 601 of the electronic device. In the present example, the acoustic port 2020 includes first and second orifices 2031, 2032 that are formed in the housing 601 and acoustically couple the acoustic cavity 2011 of the acoustic module 2006 to the external environment (external to the electronic device). In the present embodiment, the first and second orifices 2031, 2032 are offset with respect to the opening of the acoustic cavity 2011. This configuration may help reduce the direct ingress of liquid 2001 into acoustic cavity 2011 of the acoustic module 2006 Also, as shown in FIG. 20 a shield 2021 or umbrella structure that is formed between the orifices 2031, 2032 blocks the direct ingress of liquid 2001 into the acoustic cavity 2011. As shown in FIG. 20, the acoustic module 2006 also includes a screen element 2015 disposed at one end of the acoustic cavity 2011, which may also prevent the ingress of liquid or other foreign debris into the acoustic cavity 2011. The acoustic module 2006 also includes a seal 2016 disposed between the housing 601 and the connector element 2012 of the module, which may also be configured to prevent the ingress of water into the device and/or module.

In the present example depicted in FIG. 20, the acoustic module 2006 may correspond to the speaker 122 described with respect to some embodiments. As shown in FIG. 20, the acoustic module 2006 includes various components for producing and transmitting sound, including a diaphragm 2010, a voice coil 2009, a center magnet 2008, and side magnets/coils 2007. These components may cooperate to form a speaker acoustic element. In one implementation, the diaphragm 2010 is configured to produce sound waves or an acoustic signal in response to a stimulus signal in the center magnet 2008. For example, a modulated stimulus signal in the center magnet 2008 causes movement of the voice coil 2009, which is coupled to the diaphragm 2010. Movement of the diaphragm 2010 creates the sound waves, which propagate through the acoustic cavity 2011 of acoustic module 2006 and eventually out the acoustic port 2020 to a region external to the device. In some cases, the acoustic cavity 2011 functions as an acoustical resonator having a shape and size that is configured to amplify and/or dampen sound waves produced by movement of the diaphragm 2010.

As shown in FIG. 20, the acoustic module 2006 also includes a yoke 2014, support 2013, connector element 2012, and a cavity wall 2017. These elements provide the physical support of the speaker elements. Additionally, the connector element 2012 and the cavity wall 2017 together form at least part of the acoustic cavity 2011. The specific structural configuration of FIG. 20 is not intended to be limiting. For example, in alternative embodiments, the acoustic cavity may be formed from additional components or may be formed from a single component.

The acoustic module 2006 depicted in FIG. 20 is provided as one example of a type of speaker acoustic module. In other alternative implementations, the acoustic module may include different acoustic elements for producing and transmitting sound, including, for example, a vibrating membrane, piezoelectric transducer, vibrating ribbon, or the like. Additionally, in other alternative implementations, the acoustic module may be a microphone acoustic module having one or more elements for converting acoustic energy into an electrical impulse. For example, the acoustic module may alternatively include a piezoelectric microphone acoustic element for producing a charge in response to acoustic energy or sound.

As previously mentioned, because the acoustic port 2020 connects the acoustic module 2006 to the external environment, there is a possibility that liquid may accumulate or infiltrate the interior of the module. In some cases, the screen element 2015 or other protective features may not prevent all liquid from entering the acoustic cavity 2011 of the module. For example, if the device is subjected to a liquid under pressure or a directed stream of liquid, some liquid ingress may occur. Additionally, naturally occurring moisture in the air may condense and accumulate over time resulting in the presence of liquid within the module. Thus, in some implementations, the acoustic module 2006 may include one or more elements configured to expel water or liquid that accumulates in, for example, the acoustic cavity 2011 of the module. The liquid expulsion process may include modifying the charge on a portion of the wall of the acoustic cavity 2011 to change the surface energy of the wall and/or producing an acoustic pulse using the diaphragm 2010 to help expel liquid from the acoustic cavity 2011. In some embodiments, the screen 2015 may also have hydrophilic or hydrophobic properties that may facilitate removal of liquid held within the acoustic cavity 2011.

8. Example Antenna and Cover

As previously described, a wearable electronic device may be configured to communicate wirelessly with various external devices and communication networks. For the purposes of the following description, the described device 100 is one example of that shown and discussed above with respect to FIGS. 2-7. However, certain features of the device 100, including the external surface geometry, may be simplified or vary with respect to aspects of the device 100 discussed above.

In some embodiments, as previously discussed with respect to FIG. 2, the device may include one or more communication channels that are configured to transmit and receive data and/or signals over a wireless communications network or interface. Example wireless interfaces include radio frequency cellular interfaces, Bluetooth interfaces, Wi-Fi interfaces, or any other known communication interface.

In some implementations an antenna may be disposed with respect to the cover (e.g., crystal) of a device to facilitate wireless communications with an external device or communication network. In some cases, it may be advantageous to integrate an antenna into the cover to improve the transmission and reception of wireless signals from the device. In particular, the cover of the device may have dielectric properties that facilitate the transmission of radio frequency signals while also protecting the antenna from physical damage or interference. Additionally, if the antenna is integrated into a perimeter portion of the cover, the visual appearance or clarity of the cover may be minimized. Furthermore, the embodiments described below with respect to FIGS. 21A-B may be used to integrate an antenna external to the housing, without increasing the thickness of the device body.

FIG. 21A depicts a perspective exploded view of a cover 2100 and an antenna assembly 2130. The cover 2100 depicted in FIG. 21A is viewed from an inner surface 2124 that is configured to attach to or interface with the opening of the housing (described above with respect to FIG. 1). As shown in FIG. 21A, a groove 2128 may be formed within the inner surface 2124. In this example, the groove 2128 is formed around the periphery of the cover 2100. As mentioned previously, this may be advantageous in minimizing the visual impact of having the antenna assembly 2130 located within the cover 2100.

As shown in FIG. 21A the antenna assembly 2130 includes an antenna ring 2134 and a terminal 2140 which may interface with an electrical connector 2150. In the present embodiment, the groove 2128 formed in the surface of the cover 2100 may be configured to accept the antenna ring 2134. In particular, the groove 2128 may receive the entire antenna ring 2134 without a portion of the antenna ring 2134 protruding past the inner surface 2124, when the antenna ring 2134 is installed. In some cases, the groove 2128 is formed to be a clearance or near clearance fit with the diameter of the antenna ring 2134. Thus, in some cases, the antenna ring 2134 may substantially fill the groove 2128 when the ring is installed. In some cases, the groove 2128 may be configured to retain the antenna ring 2134 due to a slight interference fit or due to a feature formed within either the cover 2100 and/or the antenna assembly 2130. In the present embodiment, the antenna assembly 2130 may be installed in the cover 2100 and then connected to other electronics via the terminal 2140 and the connector 2150, which may protrude into an opening in the case or housing.

FIG. 21B depicts a cross-sectional view of the cover and antenna at the connection point. In particular, FIG. 21B depicts a detail cross-sectional view of the cover 2100 installed within the housing 601 at a region near the terminal 2140. In this example, the cover 2100 is attached to a shelf of the housing 601 via a compressible element 2122. The compressible element 2122 may provide a seal against water or other contaminates and also provide compliance between the cover 2100 and the housing 601. The compressible element 2122 may be formed from a nitrile or silicone rubber and may also include an adhesive or other bonding agent.

As shown in FIG. 21B, the antenna ring 2134 is disposed entirely within the groove 2128. In this case, the antenna ring 2134 does not protrude past the inner surface 2124. The antenna ring 2134 is electrically connected to the terminal 2140, which protrudes into an opening in the housing 601. As shown in FIG. 21B, the terminal 2140 includes conductive pads 2142 for electrically connecting to the antenna ring 2134. In this example, spring clips 2152 are configured to mechanically and electrically connect to the conductive pads 2142 on the terminal 2140. One advantage to the configuration depicted in FIG. 21B is that the antenna assembly 2130 may be installed in the cover 2100 before the cover 2100 is installed in the housing 601. The terminal 2140 and connector 2150 facilitate a blind connection that may assist electrical connection as the cover 2100 is installed. Additionally, the configuration depicted in FIG. 21B may allow for some movement between the cover 2100 and the housing 601 without disturbing the electrical connection with the antenna ring 2134.

9. Example Haptic Module

As described above, the device may include one or more haptic modules for providing haptic feedback to the user. The embodiments described herein may relate to or take the form of durable and thin haptic feedback elements suitable to provide a perceivable single pulse haptic feedback. In general, a haptic device may be configured to produce a mechanical movement or vibration that may be transmitted through the housing and/or other component of the device. In some cases, the movement or vibration may be transmitted to the skin of the user and perceived as a stimulus or haptic feedback by the user. In some implementations, the haptic feedback may be coupled to one or more device outputs to alert the user of an event or activity. For example, a haptic output may be produced in combination with an audio output produced by the speaker, and/or a visual output produced using the display.

The space constraints associated with a small wrist-worn device may present unique challenges to integrating a haptic mechanism into wearable electronics. In particular, a haptic mechanism may use a moving mass used to create the movement or vibration of the haptic output. The larger the mass that is moved, the easier it may be to create a perceivable stimulus using the haptic mechanism. However, a large moving mass and the supporting mechanism may be difficult to integrate into the compact space of, for example, the housing of a wearable electronic wristwatch.

Figure 22A:
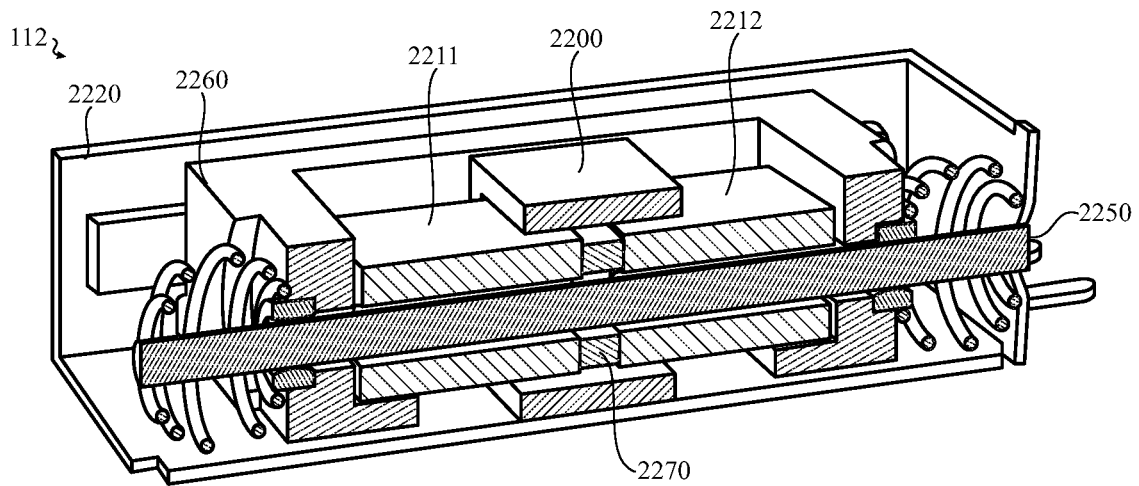
FIGS. 22A-B depict an example haptic module.
Figure 22B:
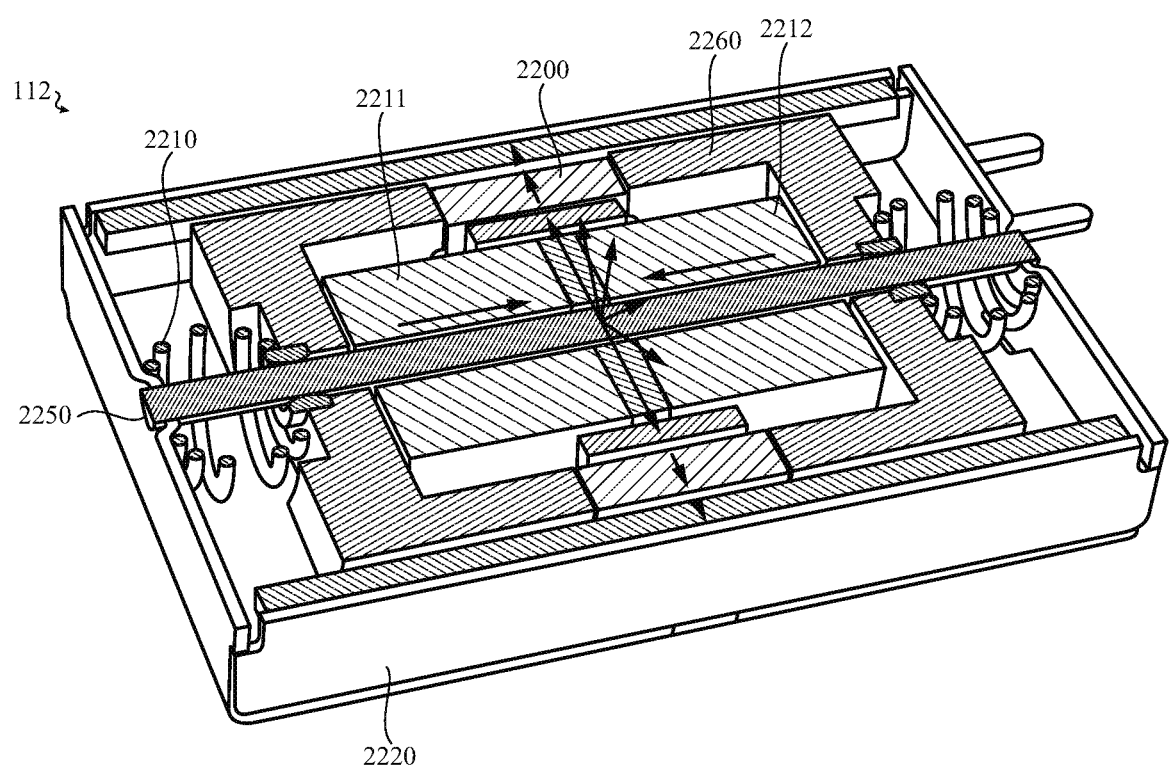

Thus, the haptic module implemented in some embodiments may be configured to maximize the mechanical energy that is produced in a very compact form factor. FIGS. 22A-B depict one example haptic mechanism that may be particularly well suited for use in a wearable electronic device. While the embodiment described with respect to FIGS. 22A-B is provided as one example, the haptic module is not limited to this particular configuration.

FIG. 22A depicts a three-quarters perspective view of a haptic device 112, with a top, front and left sidewall of the housing 2220 removed to expose internal components. FIG. 22B depicts a cross-sectional perspective view of the haptic device 112 cut in half to expose the internal components. In this example, a coil 2200 is used to induce movement of a frame 2260, which houses a central magnet array 2210. As shown in FIGS. 22A-B, the movement of the frame 2260 is guided by a shaft 2250 that is fixed with respect to a housing 2220.

In the present example, the coil 2200 may be energized by transmitting a current (e.g., from the battery) along a length of a wire that forms the coil 2200. A direction of the current along the wire of the coil 2200 determines a direction of a magnetic field that emanates from the coil 2200. In turn, the direction of the magnetic field determines a direction of movement of the frame 2260 housing the central magnet array 2210. One or more springs may bias the frame 2260 towards the middle region of the travel. In this example, the frame 2260 and central magnet array 2210, through operation of the coil 2200, function as a moving mass, which generates a tap or vibration. The output of the haptic device 112, created by the moving mass of the frame 2260 and central magnet array 2210, may be perceived as a haptic feedback or stimulus to the user wearing the device.

For example, when the coil 2200 is energized, the coil 2200 may generate a magnetic field. The opposing polarities of the magnets in the magnet array 2210 generates a radial magnetic field that interacts with the magnetic field of the coil 2200. The Lorentz force resulting from the interaction of the magnetic fields causes the frame 2260 to move along the shaft 2250 in a first direction. Reversing current flow through the coil 2200 reverses the Lorentz force. As a result, the magnetic field or force on the central magnet array 2210 is also reversed and the frame 2260 may move in a second direction. Thus, frame 2260 may move in both directions along the shaft 2250, depending on the direction of current flow through the coil 2200.

As shown in FIG. 22A, the coil 2200 encircles the central magnet array 2210, which is disposed near the center of the frame 2260. As previously described, the coil 2200 may be energized by transmitting a current along the length of the wire forming the coil 2200, and the direction of the current flow determines the direction of the magnetic flux emanating from the coil 2200 in response to the current. Passing an alternating current through the coil 2200 may cause the central magnet array 2210 (and frame 2260) to move back and forth along a shaft 2250. In order to prevent the central magnet array 2210 from being attracted to the shaft 2250, which could increase friction between the two and thereby increase the force necessary to move the central magnet array 2210 and frame 2260, the shaft 2250 may be formed from a non-ferrous material such as tungsten, titanium, stainless steel, or the like.

As depicted in FIGS. 22A-B, the coil 2200 is positioned within a frame 2260 that holds the central magnet array 2210, but is not affixed to the coil 2200. Rather, an air gap separates the coil 2200 from the central magnet array 2210 and the frame 2260 is free to move with respect to the coil 2200, which is generally stationary. Further, the frame 2260 generally moves with the central magnet array 2210. As illustrated in FIGS. 22A-B, the frame 2260 may have an aperture formed therein of sufficient size to contain the coil 2200. Even when the frame and central magnet array are maximally displaced within the housing 2220 (e.g., to one end or the other of the shaft 2250), the coil 2200 does not contact any portion of the frame 2260. It should be appreciated that the coil 2200 remains stationary in the housing 2220 while the frame 2260 and central magnet array 2210 move, although in other embodiments the coil 2200 may move instead of, or in addition to, the frame and/or central magnet array. However, by keeping the coil 2200 stationary, it may be easier to provide interconnections for the coil, such as between the coil and the flex, and therefore reduce the complexity of manufacture.

As shown in FIGS. 22A-B, the central magnet array 2210 may be formed from at least two magnets 2211, 2212 of opposing polarities. A center interface 2270 may be formed from a ferrous or non-ferrous material, depending on the embodiment. A ferrous material for the center interface 2270 may enhance the overall magnetic field generated by the central magnet array 2210, while a non-ferrous material may provide at least a portion of a return path for magnetic flux and thus assist in localizing the flux within the housing 2220. In some embodiments, the magnets 2211, 2212 are formed from neodymium while the frame is tungsten. This combination may provide a strong magnetic field and a dense mass, thereby yielding a high weight per volume structure that may be used as the moving part of the haptic device 112.

10. Example Crown Module

As described above, the device may include a crown that may be used to accept user input to the device. For the purposes of the following description, the described device 100 is one example of that shown and discussed above with respect to FIGS. 2-7. However, certain features of the device 100, including the external surface geometry, may be simplified or vary with respect to aspects of the device 100 discussed above.

In some embodiments, a crown may be used to accept rotary input from the user, which may be used to control aspects of the device. The crown may be knurled or otherwise textured to improve grip with the user's finger and/or thumb. In some embodiments, a crown may be turned by the user to scroll a display or select from a range of values. In other embodiments, the crown may be rotated to move a cursor or other type of selection mechanism from a first displayed location to a second displayed location in order to select an icon or move the selection mechanism between various icons that are output on the display. In a time keeping application, the crown may also be used to adjust the position of watch hands or index digits displayed on the display of the device. The crown may also be used to control the volume of a speaker, the brightness of the display screen, or control other hardware settings.

In some embodiments, the crown may also be configured to accept linear, as well as rotary, input. For example, the crown may be configured to translate along an axis when pressed or pulled by the user. In some cases, the linear actuation may be used as additional user input. The actuation may provide a binary output (actuated/not actuated) or may also provide a non-binary output that corresponds to the amount of translation along the axis of motion. In some instances, the linear input to the crown may be combined with the rotary input to control an aspect of the device.

The embodiments described herein may be used for at least a portion of the crown module integrated into a wearable electronic device. The embodiments are provided as examples and may not include all of the components or elements used in a particular implementation. Additionally, the crown module is not intended to be limited to the specific examples described below and may vary in some aspects depending on the implementation.

In some embodiments, an optical encoder may be used to detect the rotational motion of the crown. More specifically, the example provided below with respect to FIG. 23 may use an optical encoder to detect rotational movement, rotational direction and/or rotational speed of a component of the electronic device. Once the rotational movement, rotational direction and/or rotational speed have been determined, this information may be used to output or change information and images that are presented on a display or user interface of the electronic device.

Integrating an optical encoder into the space constraints of a typical wearable electronic device may be particularly challenging. Specifically, some traditional encoder configurations may be too large or delicate for use in a portable electronic device. The optical encoder described below may provide certain advantages over some traditional encoder configurations and may be particularly well suited for use with a crown module of a wearable electronic device.

Figure 23:
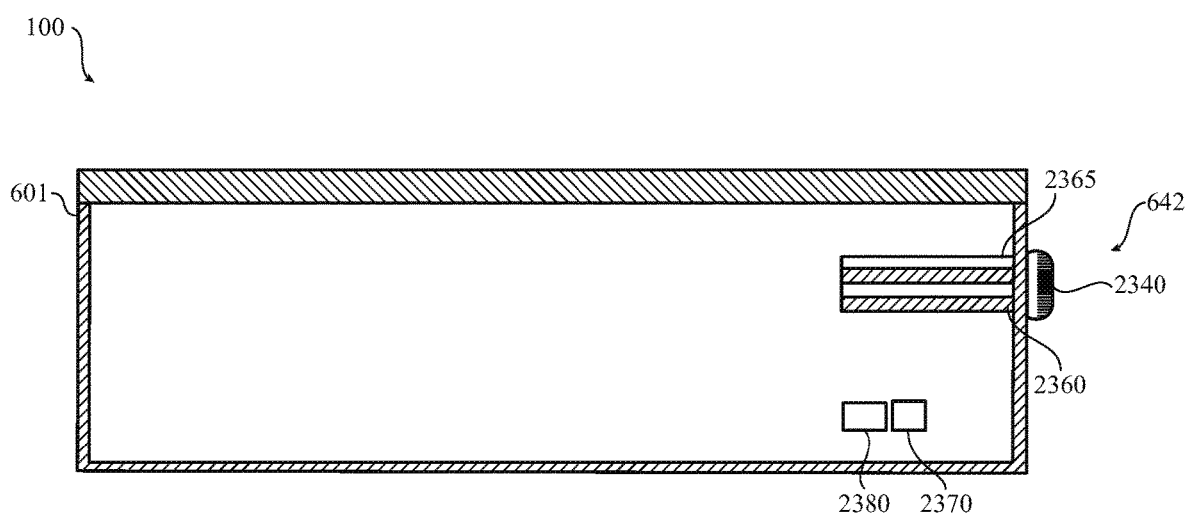
FIG. 23 depicts an example device having a crown module with an encoder.

As shown in the example embodiment of FIG. 23, the optical encoder of the present disclosure includes a light source 2370, a photodiode array 2380, and a shaft 2360. However, unlike typical optical encoders, the optical encoder of the present disclosure utilizes an encoding pattern disposed directly on the shaft 2360. For example, the encoding pattern includes a number of light and dark markings or stripes that are axially disposed along the shaft 2360. Each stripe or combination of stripes on the shaft 2360 may be used to identify a position of the shaft 2360. For example, as light is emitted from the light source 2370 and reflected off of the shaft 2360 into the photodiode array 2380, a position, rotation, rotation direction and rotation speed of the shaft 2360 may be determined. Once the rotation direction and speed are determined, this information may be used to output or change information or images that are presented on the display or user interface of the electronic device.

In other embodiments, the shape or form of the shaft of the encoder may be used to determine a position, rotation, rotation direction and rotation speed of the shaft. For example, the shaft may be fluted or have a number of channels that cause the light to be reflected in a number of different directions. Accordingly, a diffractive pattern may be used to determine the rotation, rotation direction and rotation speed of the shaft.

FIG. 23 illustrates a simplified depiction of the device 100 and crown module 642 in accordance with some embodiments. As shown in FIG. 23, the crown module 642 may be integrated with the housing 601 of the device 100 and may be formed from a dial 2340 disposed at the end of a shaft 2360. In the present embodiment, the crown module 642 also forms part of the optical encoder. As discussed above, the crown module 642 includes an optical encoder that includes a shaft 2360, a light source 2370, and a photodiode array 2380. Although a photodiode array is specifically mentioned, embodiments disclosed herein may use various types of sensors that are arranged in various configurations for detecting the movement described herein. For example, the movement of the shaft 2360 may be detected by an image sensor, a light sensor such as a CMOS light sensor or imager, a photovoltaic cell or system, photo resistive component, a laser scanner and the like.

The optical encoder may produce an encoder output that is used to determine positional data of the crown module 642. In particular, the optical encoder may produce an output that is used to detect that movement of the dial 2340 including the direction of the movement, speed of the movement and so on. The movement may be rotational movement, translational movement, angular movement, and so on. The optical encoder may also be used to detect the degree of the change of rotation of the dial 2340 and/or the angle of rotation of the dial 2340 as well as the speed and the direction of the rotation of the dial 2340.

The signals or output of the optical encoder may be used to control various aspects of other components or modules of the device. For example, continuing with the time keeping application example discussed above, the dial 2340 may be rotated in a clockwise manner in order to advance the displayed time forward. In one implementation, the optical encoder may be used to detect the rotational movement of the dial 2340, the direction of the movement, and the speed at which the dial 2340 is being rotated. Using the output from the optical encoder, the displayed hands of a time keeping application may rotate or otherwise move in accordance with the user-provided rotational input.

Referring back to FIG. 23, the crown module 642 may be formed from dial 2340 that is coupled to the shaft 2360. In some cases, the shaft 2360 and dial 2340 may be formed as a single piece. As the shaft 2360 is coupled to, or is otherwise a part of the dial 2340, as the dial 2340 rotates or moves in a particular direction and at a particular speed, the shaft 2360 also rotates or moves in the same direction and with the same speed.

As shown in FIG. 23, the shaft 2360 of the optical encoder includes an encoding pattern 2365. As discussed above, the encoding pattern 2365 may be used to determine positional information about the shaft 2360 including rotational movement, angular displacement and movement speed. As shown in FIG. 23, the encoding pattern 2365 may include a plurality of light and dark stripes.

Although light stripes and dark stripes are specifically mentioned and shown, the encoding pattern 2365 may consist of various types of stripes having various shades or colors that provide surface contrasts. For example, the encoding pattern 2365 may include a stripe or marking that has a high reflective surface and another stripe that has a low reflective surface regardless of the color or shading of the stripes or markings. In another embodiment, a first stripe of the encoding pattern 2365 may cause specular reflection while a second stripe of the encoding pattern 2365 may cause diffuse reflection. When the reflected light is received by the photodiode array 2380, a determination may be made as to the position and movement of the shaft such as described below. In embodiments where a holographic or diffractive pattern is used, the light from the light source 2370 may diffract from the shaft 2360. Based on the diffracted light, the photodiode array 2380 may determine the position, movement and direction of movement of the shaft 2360.

In some embodiments, the stripes of the encoding pattern 2365 extend axially along the shaft 2360. The stripes may extend along the entire length of the shaft 2360 or partially along a length of the shaft 2360. In addition, the encoding pattern 2365 may also be disposed around the entire circumference of the shaft 2360. In other embodiments, the encoding pattern 2365 may include a radial component. In yet other embodiments, the encoding pattern 2365 may have both a radial component and an axial component.

Figure 24A:
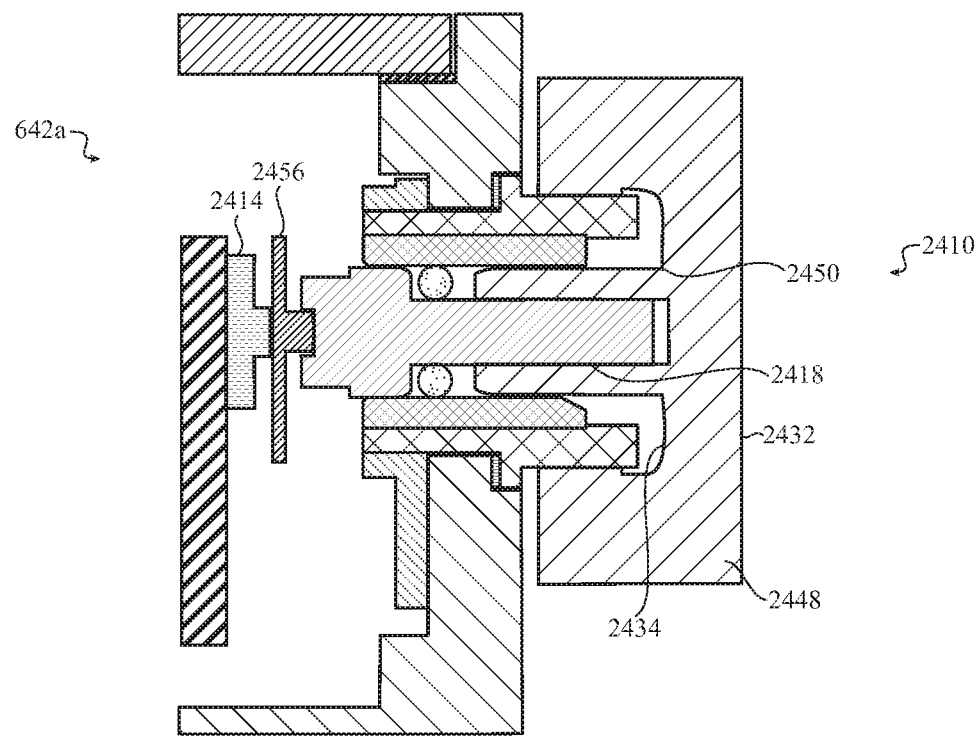
FIGS. 24A-B depict an example device having a crown module with a tactile switch.
Figure 24B:
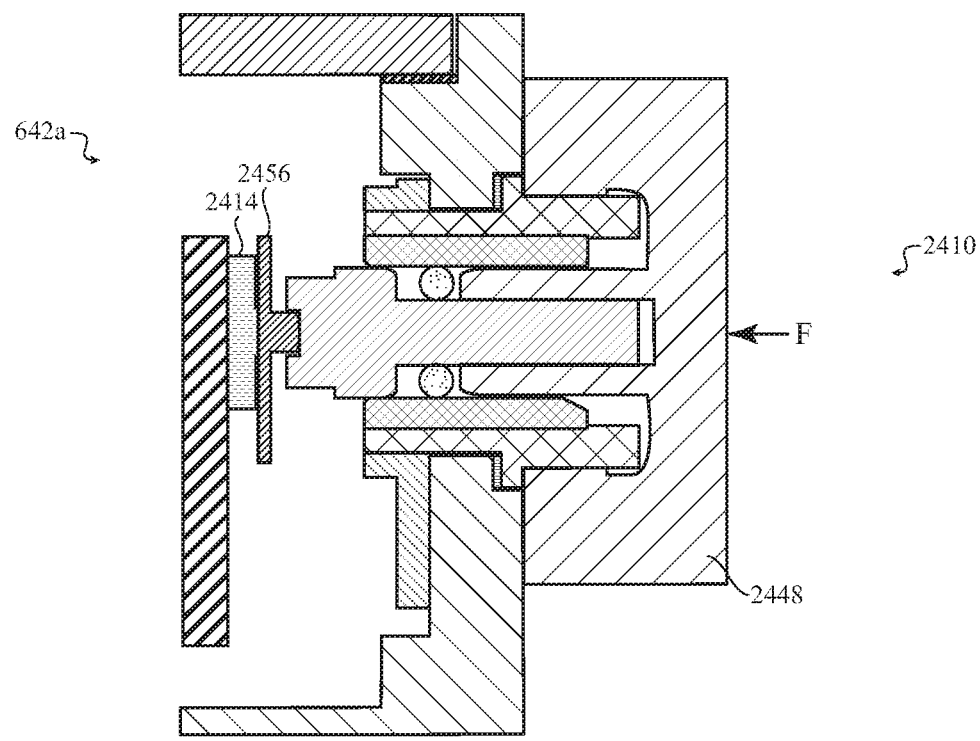

In some embodiments, the crown module may also include a tactile switch for accepting translational input from the user. FIGS. 24A-B depict another example of a crown module 642a having a tactile switch assembly 2410. As shown in FIG. 24A, the tactile switch assembly 2410 may include a dial 2448 (or button), a coupling 2418, a shear plate 2456, and a tactile switch 2414.

In the embodiment depicted in FIGS. 24A-B, the dial 2448 is translatable and/or rotatable relative to the housing. The ability of the dial 2448 to translate and rotate relative to the housing allows a user to provide a rotational force and/or translating force to the tactile switch assembly. In particular, the dial 2448 of the present example may be operably coupled to or form part of an optical encoder, in accordance with the example described above with respect to FIG. 23.

In the present example, the dial 2448 includes an outer surface 2432 that is configured to receive a rotary or rotational user input and a stem 2450 that extends from an interior surface 2434 of the dial 2448. The stem 2450 may define a coupling aperture that extends longitudinally along a length or a portion of a length of the stem 2450. In the depicted example, the stem 2450 may be hollow or partially hollow.

In the example depicted in FIGS. 24A-B, the coupling 2418 may be a linkage, such as a shaft, that couples the dial 2448 to the tactile switch 2414. The coupling 2418 may be integrally formed with the dial 2448 or may be a separate component operably connected thereto. For example, the stem 2450 of the dial 2448 may form the coupling member that is integrally formed with the dial 2448. The coupling 2418 may be made of a conductive material, such as one or more metals or metal alloys. Due to the conductive characteristics, the coupling 2418 may further act to electrically couple the dial 2448 to the tactile switch 2414 and shear plate 2456. In the example depicted in FIGS. 24A-B, the shear plate 2456 is positioned between the coupling 2418 and the tactile switch 2414. In some embodiments, the shear plate 2456 may prevent or reduce shearing forces from the coupling from being transmitted to the tactile switch. The shear plate 2456 also allows transfer of linear force input from the dial 2448 to the switch 2414.

The configuration depicted in FIGS. 24A-B may be used to accept both rotational and translational input from the user. For example, if a user provides a rotational force to the dial 2448, the coupling 2418 and dial 2448 may rotate in the direction of the force. The coupling 2418 may be attached to or integrated with one or more sensors that are configured to detect rotational movement. For example the coupling 2418 may be integrated with an optical encoder, similar to the example described above with respect to FIG. 23. Additionally, if a user provides a translational force to the dial 2448, the force may be transmitted through the dial 2448 and coupling 2418 to actuate the switch 2414. In some cases, the switch 2414 includes a metal dome switch that is configured to provide a tactile feedback when actuated. In some cases, the actuation of a dome switch may be perceived by the user as a click or release as the switch 2414 is actuated. Once the force has been removed from the dial 2448, the dome switch resiliently returns to its original position, providing a biasing force against the coupling 2418 to return both the dial 2448 and the coupling 2418 to their original positions. In some embodiments, the tactile switch 2414 may include a separate biasing element, such as a spring, that exerts a force (either directly or indirectly via the shear plate) against the coupling. FIG. 24A depicts the tactile switch assembly 2410 when there is no force applied (un-actuated). FIG. 24B depicts the tactile switch assembly 2410 when there is a translational force applied to the dial 2448 (actuated).

11. Example Band Attachment Mechanism

For the purposes of the following description, the described device 100 is one example of that shown and discussed above with respect to FIGS. 2-7. However, certain features of the device 100, including the external surface geometry, may be simplified or vary with respect to aspects of the device 100 discussed above.

As described above, a wearable electronic device may include a band that is attached to a device body having one or more receiving features. In particular, the housing may include or form a receiving feature that facilitates an interchange or replacement of different bands that are used to secure the device to the wrist of the user. By replacing or interchanging bands the device may be adapted for multiple uses ranging from sporting activities to professional or social activities.

In some embodiments, the receiving features are configured to be operated without the use of special tools or fixtures. For example, the bands may be interchanged by hand or with the help of a simple tool, such as a pointed object. Additionally or alternatively, a tool or other component, such as a component of the device to which the attachment system is coupled, may be configured to actuate a button or other component of the attachment system to secure and/or release the band from the device. In one embodiment, the lug portion of a band may be configured to be inserted into an opening or channel portion of the receiving feature. Once the lug of the band has been inserted into the opening, the lug may slide within the opening of the device until the band is secured or otherwise coupled to the device. The coupling between the band and the receiving feature may provide a secure attachment of the band to the housing or device body. Just as the band is configured to slide into the channel of the receiving feature, the lug may also slide out of the channel of the receiving feature allowing the band to be detached from the device body.

In one embodiment, the receiving feature includes a locking mechanism, which may be integrated with portions of either the band or the receiving feature. In one example, as the band is inserted into a receiving feature of the device, the locking mechanism interfaces with a portion of the receiving feature to lock or otherwise secure the band within the receiving feature. The locking mechanism may also be configured to interface with a releasing mechanism associated with the receiving feature. For example, a releasing mechanism may be configured to disengage or release the locking mechanism. In some implementations. actuation of the releasing mechanism causes the locking mechanism to be released and allows the band to be removed by sliding within the receiving feature.

Figure 25A:
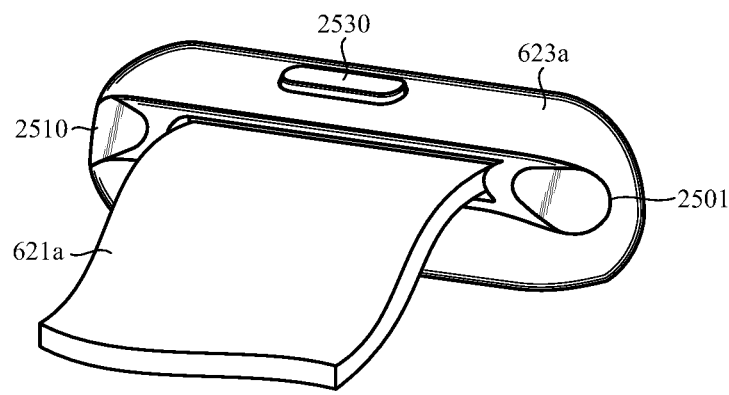
FIGS. 25A-C depict an example receiving feature for a band.

FIG. 25A depicts a receiving feature and band assembly as viewed from the bottom of the device body. As shown in FIG. 25A, a receiving feature 623a includes an opening or channel 2501 that is formed into the body or housing of the device. The channel 2501 is configured to receive the lug 2510 attached to an end of the band strap 621a. The receiving feature 623a may also include a locking mechanism 2530 that is configured to maintain the band strap 621a within the channel 2501 once it has been installed. As discussed above, the locking mechanism 2530 may be releasable by the user, which may facilitate band replacement. In this example, the locking mechanism 2530 includes a spring-loaded retaining mechanism that engages the lug 2510 to retain the lug 2510 in the channel 2501 and maintain the attachment of the band strap 621a to the device. As shown in FIG. 25A, the locking mechanism 2530 also includes a button located on the bottom of the housing that may be depressed by the user to release the locking mechanism and allow the lug 2510 and the band strap 621a to be removed from the channel 2501. In the present example, the button of the locking mechanism 2530 is located on a curved portion of the case or housing. In some embodiments, the button of the locking mechanism 2530 is located along the centerline of the case or housing.

In some embodiments, the opening or channel 2501 of the receiving feature 623a includes a port or connector for receiving a mating electrical component. In some embodiments, the connector or port is covered by a label or sticker so that the inside surface of the opening or channel 2501 appears continuous. The connector or port may be located along the vertical centerline of the case or housing.

Figure 25B:
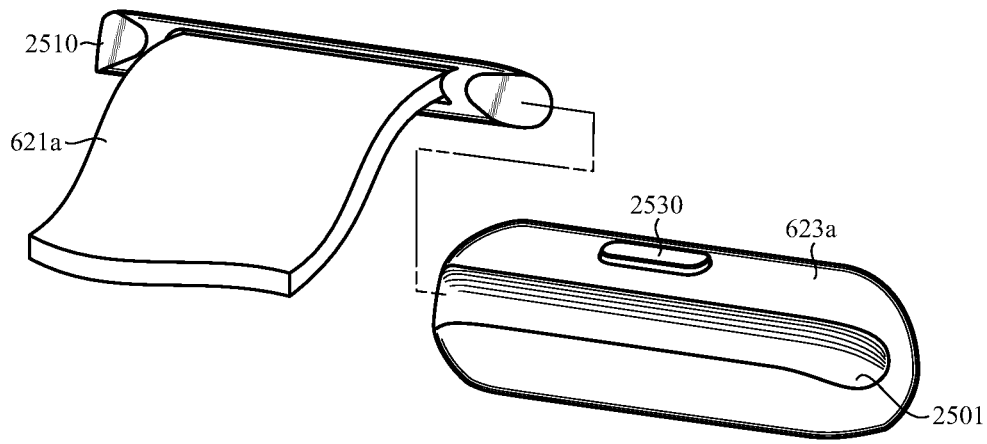

FIG. 25B depicts an example exploded view of the receiving feature 623a and the lug 2510 of the band strap 621a. As shown in FIG. 25B, the band strap 621a may be formed from a separate part and attached to lug 2510 via a pivot or other type of joint. In other embodiments, the band strap 621a may have an end feature that is integrally formed as part of the band strap 621a. As also shown in FIG. 25B, the lug 2510 may be attached to the receiving feature 623a by aligning the axis of the lug 2510 with the axis of the channel 2501 and then sliding the lug 2510 into the channel 2501.

Figure 25C:
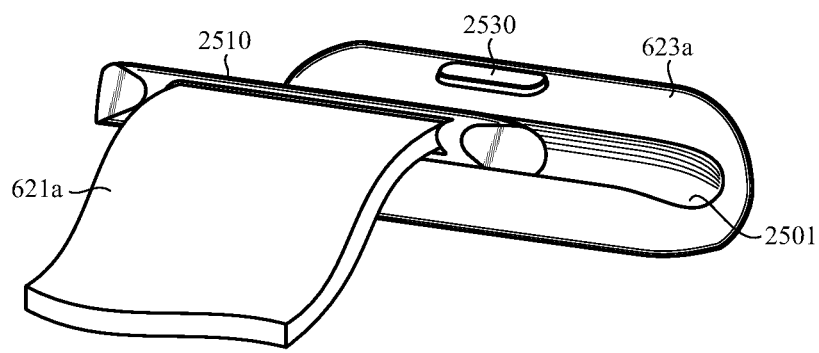

FIG. 25C depicts an example assembly sequence of the lug 2510 being inserted into the channel 2501 of the receiving feature 623a. As shown in FIG. 25C, the lug 2510 may be positioned along the side of the receiving feature 623a having the lug 2510 approximately aligned with the channel 2501 of the receiving feature 623a. The lug 2510 (and band strap 621a) may then be inserted into the channel 2501 of the receiving feature 623a by sliding the lug 2510 along the length of the channel 2501. Once the lug 2510 is approximately centered in the channel 2501 of the receiving feature 623a, the locking mechanism 2530 or other securing feature may engage, thereby retaining the lug 2510 (and band strap 621a) within the channel 2501. As previously discussed, the lug 2510 (and band strap 621a) may be removed from the receiving feature 623a by depressing the button of the locking mechanism 2530, which may disengage the lock and allow movement of the lug 2510 within the channel 2501.

The example described above is provided with respect to one example embodiment. The geometry of the end of the band strap and/or the geometry of the channel may vary depending on the implementation. Additionally, the engagement mechanism may vary depending on the design of the band strap and the device body. The geometry or layout of the features may vary and remain within the scope of the present disclosure. Additionally, while the examples provided above are described with respect to attaching a band strap to a device body, the receiving feature (623a) may be used to attach a variety of other parts to the device body. For example a lanyard, cable, or other accessory may be attached to the device body using the receiving feature and other similar features.

12. Example Bands

As described above, a wearable electronic device may include a band that is used to secure the device to the wrist of a user. In some embodiments, the band may be formed from two band straps that are attached to the housing of the device body. The band straps may be secured around the wrist of a user by a clasp or latching mechanism. As also described above, the device may be configured to facilitate replacement of the band. This feature may allow the use of a variety of types of bands, which may adapt the device for multiple uses ranging from sporting activities to professional or social activities.

In some cases, the band may be formed from a woven textile material. In one example, the band is formed from a woven material that includes one or more strands or threads formed from a natural or synthetic material. The woven material may be formed, for example, from a plurality of warp threads that are woven around one or more weft threads. More specifically, the woven material may include a plurality of warp threads disposed along the length of the band, and at least one weft thread positioned perpendicular to, and coupled to, woven or interlaced between the plurality of warp threads. In some cases, the plurality of warp threads may run the entire length of the woven portion of the band strap. Additionally, in some cases, the at least one weft thread may include a single thread that may be continuously woven between the plurality of warp threads or, alternatively, may include a plurality of threads that may be woven between the plurality of warp threads. A weft thread that is woven between a plurality of warp threads may form consecutive cross-layers with respect to the plurality warp threads in order to form the band.

In some cases, one or more of the strands or threads may be a metallic or conductive material. This may improve the strength of the band and may also facilitate coupling with magnetic elements, such as a metallic clasp. In some cases, other elements may be woven into the band, including, for example, product identifying elements, decorative elements, or functional components.

In other embodiments, the band may be formed from a metallic mesh material. In one example, the metallic mesh is formed from an array of links that are interlocked to form a sheet of fabric. Some or all of the links in the mesh may be formed from a ferromagnetic material, which may facilitate magnetic engagement with a magnetic clasp. In some cases, each link of the mesh is formed from a section of metallic filament that is bent or formed into a closed shape. Each closed shape may be interlocked with one or more adjacent links to form a portion of the sheet or fabric. In some cases, a metallic filament is formed around a series of rods or pins that are disposed at a regular spacing within the mesh. In some cases, one or more strands or filaments that may be formed from a ferromagnetic material are woven or integrated with the links of the mesh.

In other examples, the band may be formed from a sheet of material. For example, the band may be formed from a synthetic leather, leather, or other animal hide. Additionally or alternatively, the band may be formed from a polymer material, an elastomer material, or other type of plastic or synthetic. In some cases, the band is formed from a silicone sheet material.

The clasp that is used to attach the free ends of the band straps may vary depending on the material that is used and the construction of the band. For example, as mentioned above, a metallic mesh material may use a metallic clasp to join the ends of the band. Additionally, a leather band may be integrated with magnetic and/or ferromagnetic components and may include a magnetic clasp. In some embodiments, the free ends of the band straps are secured using a buckle or tang on a first band strap that is configured to interface with a hole or aperture in a second band strap. A variety of other clasp configurations may also be used.

13. Example Display

For the purposes of the following description, the described device 100 is one example of that shown and discussed above with respect to FIGS. 2-7. However, certain features of the device 100, including the external surface geometry, may be simplified or vary with respect to aspects of the device 100 discussed above. As described above, the device includes a display disposed within the housing or enclosure. The device may be formed from a liquid crystal display (LCD), organic light emitting diode (OLED) display, organic electroluminescence (OEL) display, or other type of display device. The display may be used to present visual information to the user, including, for example, a graphical user interface, notifications, health statistics, and the like. In some cases, the display may be configured to present the current time and date similar to a traditional watch or timepiece.

Figure 26:
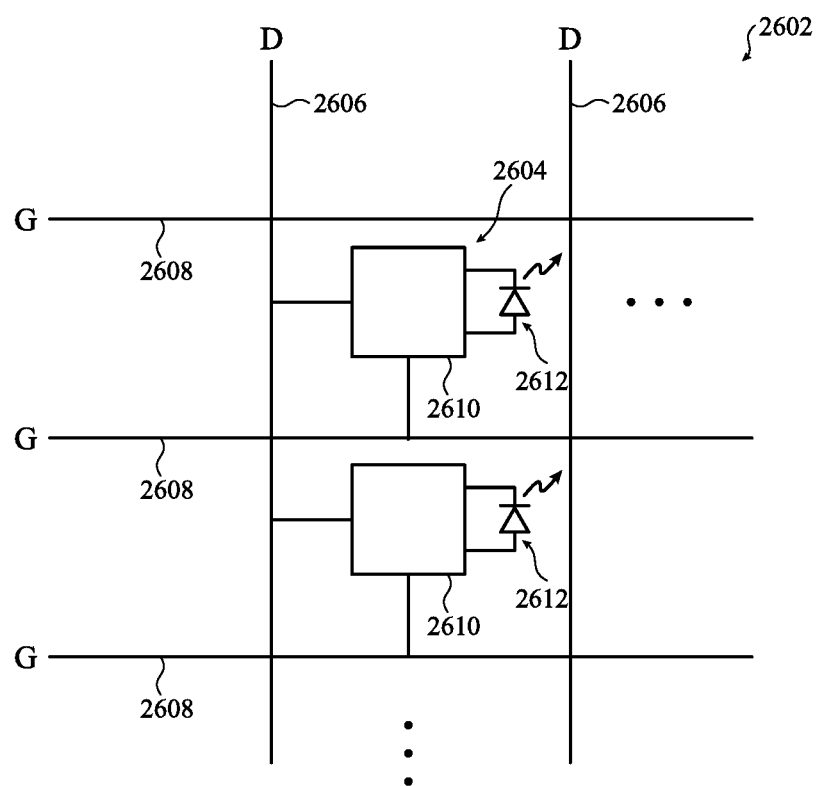
FIG. 26 depicts example elements of a display.

In some embodiments, the display is formed from an organic light emitting diode (OLED) display element. An active region of the display may include an array of light-emitting display pixels 2604 such as array 2602, shown in FIG. 26. Pixels 2604 may be arranged in rows and columns in array 2602 and may be controlled using a pattern of control lines. Each pixel may include a light-emitting element such as organic light-emitting diode 2612 and associated control circuitry 2610. Control circuitry 2610 may be coupled to the data lines 2606 and gate lines 2608 so that control signals may be received from driver circuitry, which may be implemented as an integrated circuit. Although described as an OLED display, certain embodiments may implement other display technology, such as LCD displays and the like.

To the extent that multiple functionalities, operations, and structures are disclosed as being part of, incorporated into, or performed by device 100, it should be understood that various embodiments may omit any or all such described functionalities, operations, and structures. Thus, different embodiments of the device 100 may have some, none, or all of the various capabilities, apparatuses, physical features, modes, and operating parameters discussed herein Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments but instead defined by the claims herein presented.

We claim:

1. An electronic watch comprising:
   a housing formed from a metal material and defining a rear opening along a rear portion of the housing;
   a touch-sensitive display positioned at least partially within the housing;
   a band coupled to the housing and configured to couple the electronic watch to a user;
   a cover formed from a dielectric material and forming a seal along the rear opening of the housing;
   an optical sensor positioned within the housing and configured to transmit an optical signal through the dielectric material of the cover;
   a charging coil positioned within the housing and configured to receive wireless power through the dielectric material of the cover;
   a first electrode positioned along a rear surface of the electronic watch; and
   a second electrode positioned along the rear surface of the electronic watch, wherein:
      the electronic watch is configured to measure a heart rate using the optical sensor, and
      the electronic watch is configured to measure an electrocardiogram using the first electrode and the second electrode.

2. The electronic watch of claim 1, wherein:
   the cover defines at least one window for the optical sensor; and
   the cover protrudes outward from a rear housing surface of the housing.

3. The electronic watch of claim 1, wherein:
   the cover is formed from a transparent substrate; and
   the transparent substrate comprises one or more of a glass or a sapphire material.

4. The electronic watch of claim 1, wherein:
   the electronic watch further comprises a first magnet positioned within the housing;
   the first magnet is configured to couple to a second magnet positioned within a charging dock; and
   the first and second magnets are configured to maintain alignment of the electronic watch with respect to the charging dock.

5. The electronic watch of claim 1, wherein:
   the electronic watch further comprises a near-field communication system; and
   the near-field communication system is configured to transmit signals through one or more of the housing or the cover.

6. The electronic watch of claim 1, wherein:
   the cover defines a convex exterior profile; and
   the convex exterior profile facilitates alignment between the cover and a mating surface of an external wireless charging device.

7. A wearable electronic device comprising:
   a housing formed from a conductive material and defining a first opening opposite to a second opening;
   a band attached to the housing and configured to secure the wearable electronic device to a user;
   a display positioned in the first opening;
   a cover comprising a non-conductive material and positioned over the second opening, the cover forming a portion of an exterior surface of the wearable electronic device;
   a biosensor module positioned below the cover configured to pass an optical signal through a window defined within the non-conductive material of the cover; and
   a wireless charging receive coil aligned with the second opening and below the cover, the wireless charging receive coil configured to inductively couple to an external wireless charging device through the non-conductive material of the cover.

8. The wearable electronic device of claim 7, wherein:
the window is a first window;
the cover defines a second window; and
the biosensor module comprises:
  a light source configured to emit light toward a region of skin of the user through the first window: and
  a detector configured to receive light reflected from the region of the skin through the second window.

9. The wearable electronic device of claim 7, wherein:
the biosensor module comprises:
  at least one light source; and
  a set of detectors; and
the at least one light source and the set of detectors are configured to operate as a photoplethysmogram (PPG) sensor.

10. The wearable electronic device of claim 7, wherein:
the cover protrudes outward from a rear surface of the housing;
the cover defines a convex exterior profile; and
the convex exterior profile facilitates alignment between the cover and a mating surface of the external wireless charging device.

11. The wearable electronic device of claim 10, wherein:
the cover forms a waterproof seal with the housing along a perimeter of the cover.

12. The wearable electronic device of claim 7, wherein:
the wearable electronic device further comprises a first magnet positioned within the housing and below the cover;
the external wireless charging device comprises a second magnet; and
the first and second magnets are configured to maintain alignment between the wearable electronic device and the external wireless charging device during a charging operation.

13. The wearable electronic device of claim 7, wherein:
the wearable electronic device further comprises:
  a first electrode positioned along a rear surface of the wearable electronic device; and
  a second electrode positioned along the rear surface of the wearable electronic device; and
the wearable electronic device is configured to measure an electrocardiographic characteristic using the first and second electrodes.

14. An electronic device comprising:
a housing defining a first opening and a second opening;
a display positioned at least partially within the first opening;
a biosensor module aligned with the second opening;
a wireless charging receive coil positioned within the housing and aligned with the second opening;
a battery operably coupled to the wireless charging receive coil; and
a cover formed from an optically transparent material and disposed over the biosensor module and the wireless charging receive coil, wherein:
  the electronic device is configured to receive wireless power through the optically transparent material of the cover using the wireless charging receive coil; and
  the electronic device is configured to measure a heart rate of a user through the optically transparent material of the cover using the biosensor module.

15. The electronic device of claim 14, wherein:
the biosensor module includes an array of optical components; and
the cover defines an array of windows, each window of the array of windows aligned with a respective optical component of the array of optical components.

16. The electronic device of claim 14, wherein:
the biosensor module comprises:
  a light source; and
  a detector;
the light source and the detector are configured to measure changes in light absorption by a region of skin of the user;
the electronic device is configured to compute the heart rate using the measured changes in light absorption; and
the display is configured to display information associated with the heart rate.

17. The electronic device of claim 14, wherein:
the electronic device further comprises:
  a first electrode disposed along an exterior of the electronic device; and
  a second electrode disposed along the exterior of the electronic device; and
the first and second electrodes are configured to measure an electrocardiographic characteristic of the user.

18. The electronic device of claim 14, wherein:
the electronic device further comprises a magnet that is configured to magnetically couple the electronic device to an external inductive power transmitter dock through the cover.

19. The electronic device of claim 14, wherein the cover protrudes outward from a rear surface of the housing to facilitate alignment between the cover and a mating surface of an external wireless charging device.

* * * * *

(12) INTER PARTES REVIEW CERTIFICATE (4023rd)
United States Patent (10) Number: US 10,942,491 K1
Rothkopf et al. (45) Certificate Issued: Jul. 14, 2025

(54) WEARABLE ELECTRONIC DEVICE

(71) Applicant: Apple Inc.

(72) Inventors: Fletcher R. Rothkopf; Jonathan Ive; Julian Hoenig; Rico Zorkendorfer

(73) Assignee: APPLE INC.

Trial Number:

IPR2023-00734 filed Mar. 20, 2023

Inter Partes Review Certificate for:

Patent No.: 10,942,491
Issued: Mar. 9, 2021
Appl. No.: 16/826,130
Filed: Mar. 20, 2020

The results of IPR2023-00734 are reflected in this inter partes review certificate under 35 U.S.C. 318(b).

INTER PARTES REVIEW CERTIFICATE
U.S. Patent 10,942,491 K1
Trial No. IPR2023-00734
Certificate Issued Jul. 14, 2025

AS A RESULT OF THE INTER PARTES REVIEW PROCEEDING, IT HAS BEEN DETERMINED THAT:

Claims 1-19 are cancelled.

\* \* \* \* \*